(12) United States Patent
Roth et al.

(10) Patent No.: US 7,067,259 B2
(45) Date of Patent: Jun. 27, 2006

(54) **MULTIDRUG RESISTANCE PROTEINS IN *DROSOPHILA* AND *ANOPHELES***

(75) Inventors: Charles W. Roth, Rueil Malaison (FR); Paul T. Brey, Paris (FR); Inge Holm, Clamart (FR); Marine Grailles, Orcement (FR); Andrey Rzhetsky, New York, NY (US)

(73) Assignee: Institut Pasteur, Paris (FR)

( * ) Notice: Subject to any disclaimer, the term of this patent is extended or adjusted under 35 U.S.C. 154(b) by 57 days.

(21) Appl. No.: 10/667,891

(22) Filed: Sep. 23, 2003

(65) Prior Publication Data

US 2004/0171024 A1   Sep. 2, 2004

Related U.S. Application Data

(60) Provisional application No. 60/413,469, filed on Sep. 26, 2002.

(51) Int. Cl.
*C12Q 1/68* (2006.01)
*C07K 14/435* (2006.01)
*C07H 21/04* (2006.01)
*C12N 5/06* (2006.01)

(52) U.S. Cl. .................. 435/6; 435/69.1; 435/320.1; 435/348; 530/395; 536/23.5

(58) Field of Classification Search ................ 435/6, 435/69.1, 320.1, 348; 530/395; 536/23.5
See application file for complete search history.

(56) References Cited

U.S. PATENT DOCUMENTS 5,489,519 A * 2/1996 Deeley et al. ............. 435/69.1

FOREIGN PATENT DOCUMENTS

WO   WO 200171042 A2 * 9/2001

OTHER PUBLICATIONS

Wu, C.T., Budding, M., Griffin, M.S., and J.M. Croop. 1991. Isolation and Characterization of *Drosophila* Multidrug Resistance Gene Homologs. Mol. & Cell. Biol. 11(8):3940-3948.*

Zhang, D.W., et al. 2001 Identification of a Nonconserved Amino Acid Residue in Multidrug Resistance Protein 1 Important for Determining Substrate Specificity. J. Biol. Chem. 276(37): 34966-34974.*

Borst et al.; A Family of Drug Transporters: the Multidrug Resistance-Associated Proteins; J. Nat'l Cancer Inst., vol. 92(16) (Aug. 2000), pp. 1295-1302.

Dean et al.; The Human ATP-Binding Cassette (ABC) Transporter Superfamily; Cold Spring Harbor Laboratory Press; vol. 11 (2002) pp. 1156-1166.

Lu et al.; AtMRP1 Gene of *Arabidopsis* Encodes a Glutathione S-Conjugate Pump: Isolation and Functional Definition of a Plant ATP-binding Cassette Transporter Gene; PNAS vol. 94 (Jul. 1997) pp. 8243-8248.

Morrow et al.; Combined Expression of Multidrug Resistance Protein (MRP) and Glutathione S-Transferase P1-1 (GSTP1-1) in MCF7 Cells and High Level Resistance to the Cytotoxicities of Ethacrynic Acid but Not Oxazaphosphorines or Cisplatin; Biochemical Pharmacology, vol. 56 (1998) pp. 1013-1022.

Morrow et al.; Coordinated Action of Glutathione S-Transferases (GSTs) and Multidrug Resistance Protein 1 (MRP1) in Antineoplastic Drug Detoxification; J. Biol. Chem.; vol. 273(32) (Aug. 1998) pp. 20114-20120.

Ito et al.; Mutation of a Single Conserved Tryptophan in Multidrug Resistance Protein 1 (MRP1/ABCC1) Results in Loss of Drug Resistance and Selective Loss of Organic Anion Transport, J. Biol. Chem., vol. 276(19) (May 2001) pp. 15616-15624.

Zhang et al.; Identification of a Nonconserved Amino Acid Residue in Multidrug Resistance Protein 1 Important for Determining Substrate Specificity, J. Biol. Chem., vol. 276(37) (Sep. 2001) pp. 34966-34974.

Roth et al.; Identification of the *Anopheles gambiae* ATP-binding Cassette Transporter Superfamily Genes; Mol. Cells, vol. 15(2) (Apr. 2003) pp. 150-158.

Grailles et al.; The *Drosophila melanogaster* Multidrug-Resistance Protein 1 (MRP1) Homolog has a Novel Gene Structure Containing Two Variable Internal Exons; Gene 307 (2002) pp. 41-50.

PCT Notification of Transmittal of the International Search Report and International Search Report mailed Dec. 11, 2004.

PCT Invitation to Pay Additional Fees and Annex to Form PCT/ISA/206 Communication Relating to the Results of the Partial International Search (6 pages), mailed Jul. 23, 2004.

Adams, M.D. et al., "*Drosophila melanogaster* protein CG6214", XP002283693, retrieved from Database accession No. Q9I7N0 abstract, Mar. 1, 2001.

Gerrard, Bernard et al., Analysis of Mdr50: A *Drosophila* P-Glycoprotein/Multidrug Resistance Gene Homolog, Genomics 17, 83-88 (1993).

* cited by examiner

*Primary Examiner*—Robert A. Wax
*Assistant Examiner*—Marsha Tsay
(74) *Attorney, Agent, or Firm*—Finnegan, Henderson, Farabow, Garrett & Dunner, L.L.P.

(57) ABSTRACT

The invention provides, inter alia, isolated nucleic acid molecules that comprise nucleic acids encoding multiple drug resistance proteins from *Drosophila melanogaster* or *Anopheles gambiae*, herein referred to as dMRP or gMRP, respectively, vectors encoding dMRP or gMRP, and host cells transformed with vectors containing these nucleic acids.

8 Claims, 9 Drawing Sheets

MULTIDRUG RESISTANCE PROTEINS IN *DROSOPHILA* AND *ANOPHELES*

CROSS-REFERENCE TO RELATED APPLICATIONS

This application is based on and claims the benefit of U.S. Provisional Application Ser. No. 60/413,469, filed Sep. 26, 2002. The entire disclosure of this Provisional application is relied upon and incorporated by reference herein.

BACKGROUND OF THE INVENTION

This invention relates to recombinant DNA technology. In particular, this invention concerns the cloning of nucleic acids encoding multiple drug resistance proteins of *Drosophila melanogaster* and *Anopheles gambiae*. More particularly, this invention provides isolated nucleic acid compounds encoding multiple drug resistance proteins of *Anopheles gambiae* and *Drosophila melanogaster*. Vectors and transformed host cells comprising the multiple drug resistance-encoding DNA of *Anopheles gambiae* and *Drosophila melanogaster* are also provided. The invention further provides assays, which utilize these transformed host cells.

The multidrug-resistance associated protein, MRP1, a large (190 kDa) membrane glycoprotein, was identified in 1992 in a human small-cell lung cancer cell line where its overexpression conferred resistance to a large spectrum of drugs (Cole et al., 1992). MRP joined the P-glycoprotein MRP1, the original protein associated with broad resistance, discovered in 1976 (Juliano & Ling, 1976). The description of MRP1 was followed by the characterization of several other structurally related human proteins: MRPs 2 to 8; followed by MRP9 (Bera et al., 2001; Büchler et al., 1996; Dean et al., 2001; Hopper et al., 2001). These proteins, like MRP1, are members of the ATP-binding cassette (ABC) superfamily, present from bacteria to man, and involved in the energy-dependent transmembrane transport of a variety of molecules, ranging from inorganic ions to large polypeptides. Like other ABC-transporters, MRP homologs are well conserved in evolution and have been described in several mammals (Büchler et al., 1996; Kool et al., 1997; van Aubel et al., 1998), in the nematode *Caenorhabditis elegans* (Broeks et al., 1996), in the protozoan parasite Leishmania (Essodaigui et al., 1999), in yeast (Szczypka et al., 1994), and in plants (Lu et al., 1997).

ABC transporters are typically composed of two membrane spanning domains (MSDs), containing several transmembrane α-helices, and two cytosolic nucleotide binding domains (NBDs), responsible for the hydrolysis of ATP, thus providing the necessary energy for substrate transport. MRP1 is one of several members of the MRP subfamily characterized by a third MSD of unknown function at the N-terminus of the protein (Borst et al., 2000). The NBDs are highly conserved and share two sequence motifs, designated "Walker A" and "Walker B", with other nucleotide binding proteins. These sequences are separated by a stretch of about 120–170 amino acids, including a short (12–13 amino acid) peptide motif called the ABC transporter "signature" region. In contrast, the MSDs are highly divergent and are probably involved with the protein's substrate specificity.

Notwithstanding these advances in the art, there continues to be a need in the art to identify MRPs in other species. For example, the identification of MRPs in insects could aid in the development of more effective insecticides.

SUMMARY OF THE INVENTION

This invention describes the identification and characterization of a Drosophila MRP encoding a protein whose deduced amino acid sequence is closely related to that of human MRP1. (See FIG. 6.) Of particular interest is the identification of multiple copies of two exons (4 and 8), suggesting alternative splicing at the mRNA level. This hypothesis is supported by a RT-PCR strategy presented here.

The dMRP of *Drosophila melanogaster* was the first description of a MRP homologue in an insect. Its deduced amino acid sequence is close (48% identity and 64.5% similarity) to that of the human MRP1 discovered in 1992 (Cole et al., 1992), and involved in the drug resistance of several tumors. These proteins belong to the ABCC1 subfamily of ATP-binding cassette (ABC) transporters, known to transfer a large variety of compounds across the cell membrane. Despite their close relatedness with other subgroups of ABC transporters, such as P-glycoproteins, CFTR, and sulfonylurea receptors, MRP proteins clearly form a separate cluster within this group, thus constituting an independent family (Borst et al., 1999).

Extending these earlier findings, this invention also involves the discovery of the arrangement as a cluster of genes of the four copies of MRP homologues in *Anopheles gambiae*, located on the chromosome 3R arm, and that all read on the same sense. This invention shows by RT-PCR that these potential genes are all transcribed in the adult mosquito, and seem ubiquitous in the different tissues. But their respective expressions are not always equivalent. The newly described genes are called gMRP1a, gMRP1b, gMRP1c, and gMRP1d. (See FIG. 6.) The three last have a close exon-intron structure (especially gMRP1c and gMRP1d), and share a strong homology and similarity, at the level of their amino acid sequences. In contrast, gMRP1a is much more different from the others regarding its sequence as well as structure, with only three introns in place of five in gMRP1b, and 6 in gMRP1c and gMRP1d.

The invention provides, inter alia, isolated nucleic acid molecules that comprise nucleic acids encoding multiple drug resistance proteins from *Drosophila melanogaster* or *Anopheles gambiae*, herein referred to as dMRP or gMRP, respectively, vectors encoding dMRP or gMRP, and host cells transformed with vectors containing these nucleic acids.

In another embodiment, the invention provides a method for determining the insecticidal MRP inhibition activity of a compound which comprises:

a) placing a culture of insect cells, transformed with a vector capable of expressing dMRP or gMRP, in the presence of:
  (i) an insecticidal agent to which said insect cell is resistant, but to which said insect cell is sensitive in its untransformed state;
  (ii) a compound suspected of possessing insecticidal MRP inhibition activity; and
b) determining the insecticidal MRP inhibition activity of said compound by measuring the ability of the insecticidal agent to inhibit the growth of said insect cell.

In still another embodiment, the present invention relates to strains of *Drosophila melanogaster* or *Anopheles gambiae* in which the dMRP or gMRP gene is disrupted or otherwise mutated such that the dMRP or gMRP protein is not produced in said strains.

In yet another embodiment, the present invention relates to a method for identifying new insecticidal compounds.

This invention further provides isolated polynucleotides that comprise an isolated DNA sequence encoding SEQ ID NOS: 1, 2, 3, 4, or 5, or a vector containing the isolated polynucleotide.

The isolated polynucleotide of the invention, or a portion thereof, can be labeled with a detectable moiety.

A host cell containing the vector of the invention is also provided.

A method for constructing a transformed host cell capable of expressing SEQ ID NOS: 1, 2, 3 4, or 5 comprises transforming a host cell with a recombinant DNA vector that comprises an isolated DNA sequence of the invention.

A method for expressing SEQ ID NOS: 1, 2, 3, 4 or 5 in a transformed host cell comprises culturing the transformed host cell of the invention under conditions suitable for gene expression.

BRIEF DESCRIPTION OF THE DRAWINGS

This invention will be described in greater detail in the drawings in which:

FIG. 1. Comparison of deduced D. melanogaster cDNA SD07655 (SEQ ID NO: 1) and human MRP1 (SEQ ID NO: 6) amino acid sequences. The two amino acid sequences were aligned using ClustalW. Identical residues are marked with shading. The transmembrane regions are noted by a fine underline and the ATP-binding domains are noted by a bold underline. The amino acids derived from exons 4 and 8 of the dMRP gene are presented in bold characters. The small vertical lines above and below the amino acids denote the exon junctions with the type of splice junction marked by a number noting the class: 0, 1 or 2. The dMRP amino acid sequence differs from that of sequence AY069827 at the following positions: L/V pos. 124, M/L pos. 318 and I/T pos. 448.

FIG. 6. Comparison of deduced A. gambiae gMRP1a–d (SEQ ID NOS 2–5), Drosophila melanogaster dMRP (SEQ ID NO: 1), and human MRP1 (SEQ ID NO: 6) amino acid sequences. The alignment was produced using ClustalW. Identical residues in at least half of the sequences are marked with shading. The different topological regions are indicated in bold and italic above the sequences, and are delimited by vertical bars. MSD1–3, Membrane Spanning Domains 1 to 3; $L_0$, cytoplasmic loop; NBD1–2, Nucleotide Binding Domain, Linker, region linking the two halves of the protein. Walker A and Walker B are indicated as A and B, and their sequences are marked in bold, as well as the signature (C) of ABC transporters. The vertical lines in bold inside the amino acid sequences denote the exon junctions. Where several genes shared the same site, this one was emphasized by a delimitating box.

DETAILED DESCRIPTION OF THE INVENTION

Figure 2:
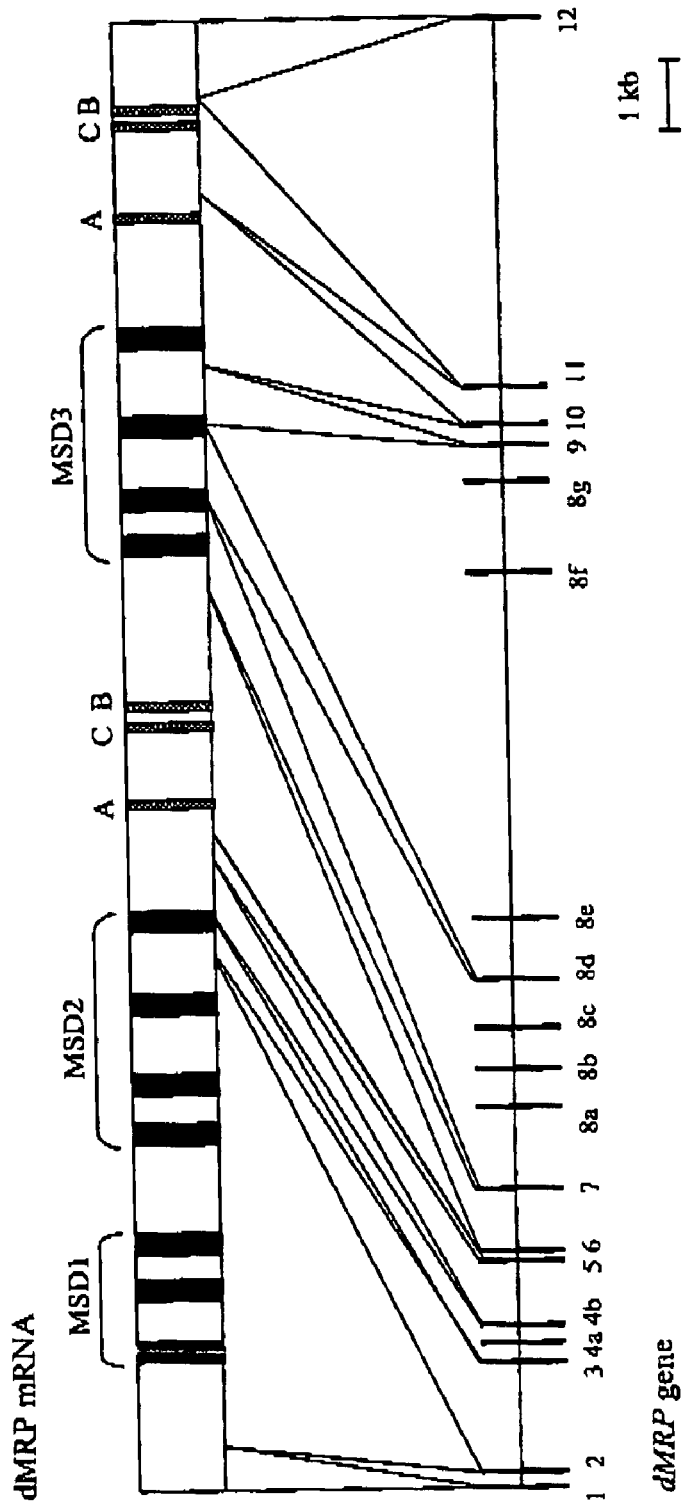
FIG. 2. Genomic organization of dMRP and alignment of the splice junctions with dMRP cDNA SD07655. The intron-exon organization of dMRP is illustrated at the bottom with the exons indicated by the vertical bars and introns by the thin horizontal lines. The regions of the dMRP mRNA encoded by each exon are shown at the top. Superimposed on the mRNA is a schematic of the protein with membrane spanning domains (MSDs), and nucleotide binding domains (NBDs). Within each MSD, the transmembrane helices are shown as black bars. Walker A and Walker B are designated as A and B, respectively, and C indicates the ABC family signature.

At the beginning of 2001, an international consortium organized the A. gambiae genome project, which now comes in line with the sequencing of the Plasmodium and the human genomes. Before the release of the whole sequence on (a web site) preliminary work on a BAC clone library was generated by Frank H. Collins, Univ. of Notre Dame, USA. The BAC library inserts ends were sequenced by the Genoscope (Evry, France) and representing the anopheline genome, allowed the finding of four copies of homologues of the Drosophila and human MRPs, which were further characterized. The study of the Drosophila gene had put in light a new splicing process in comparison to previously examined MRPs in several animals. Two exons are present as multiple copies, which potentially allows the insect to express as many as 14 different variants of the protein. This peculiar process was not retrieved in A. gambiae.

Figure 6:
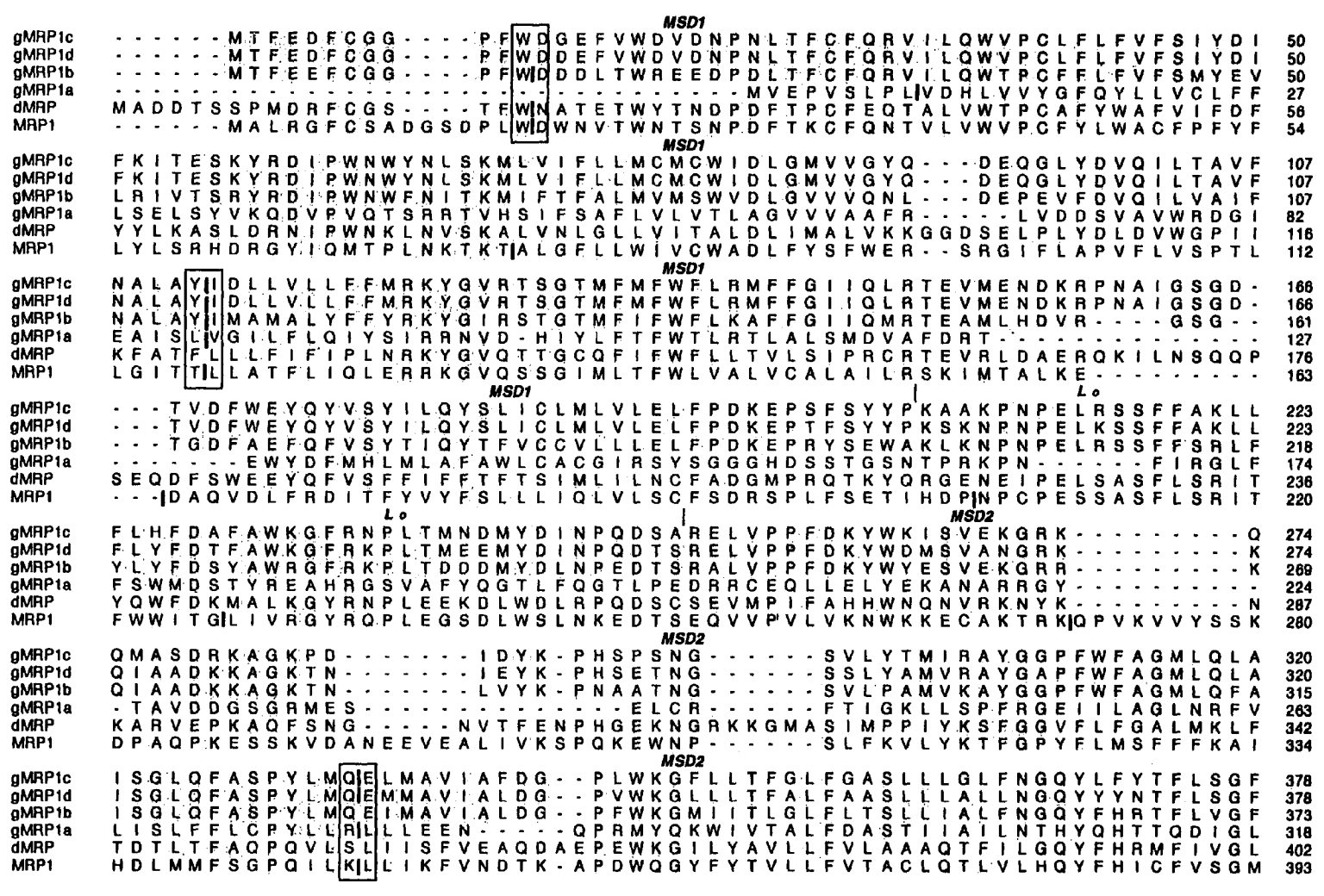
Figure 6:
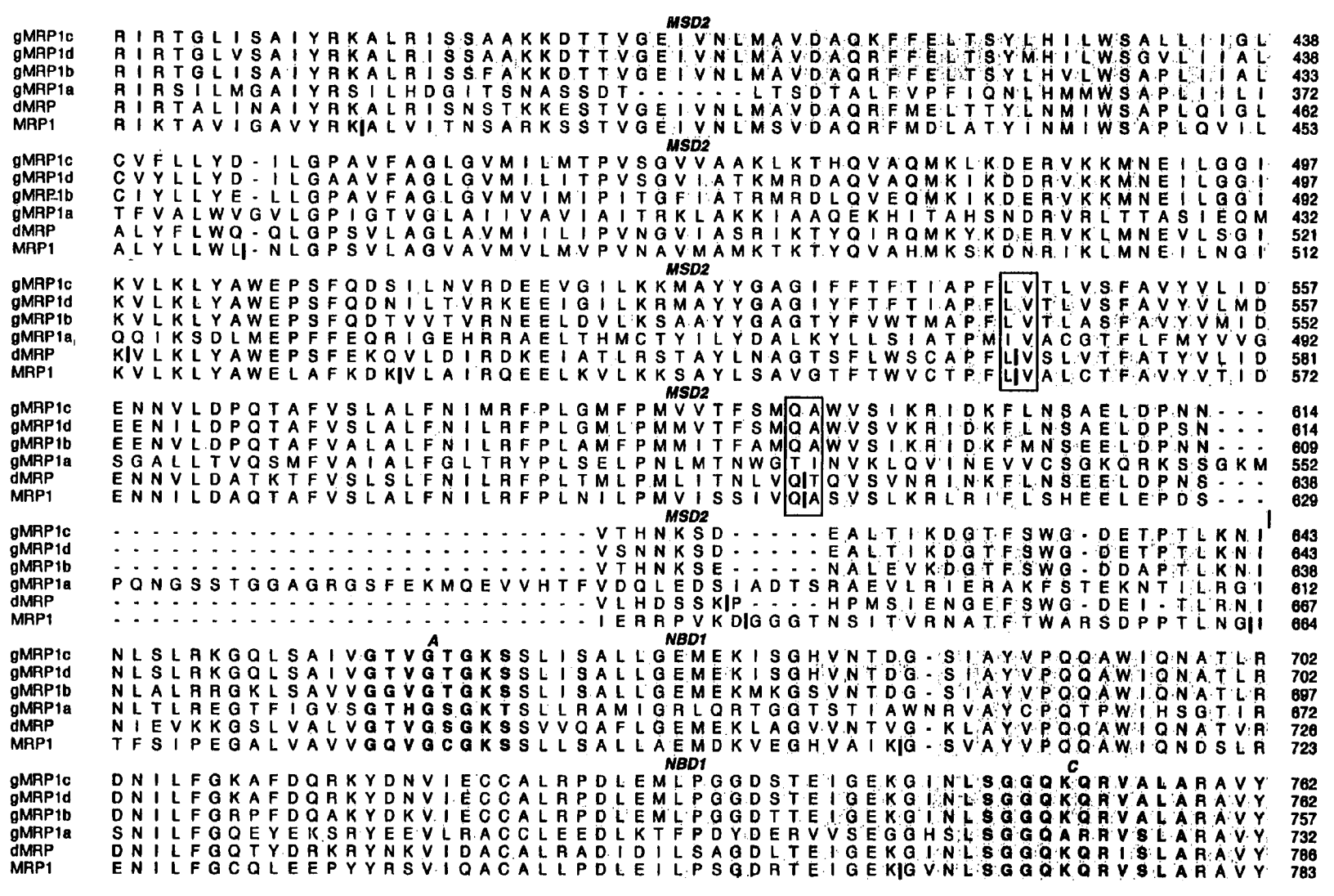
Figure 6:
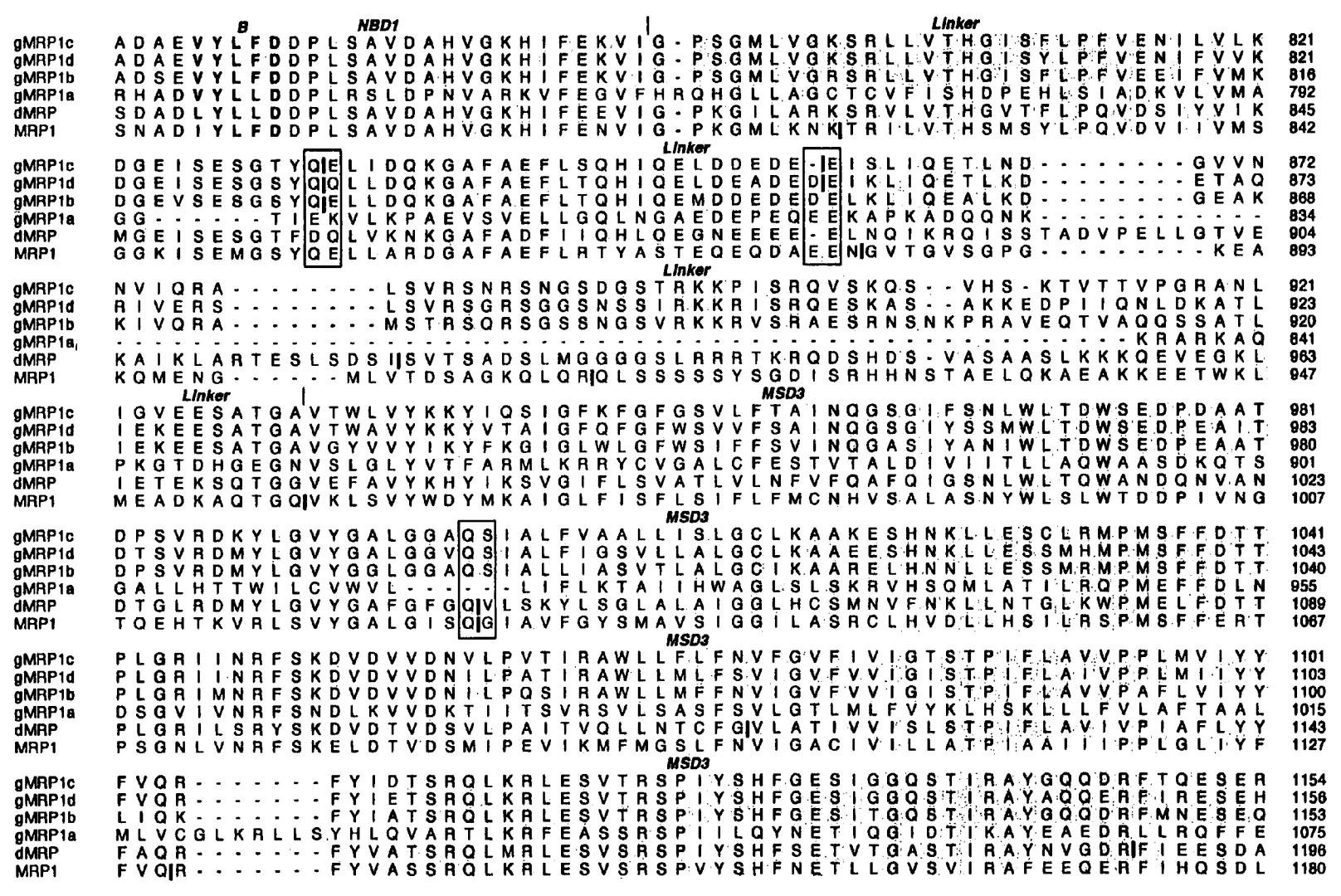
Figure 6:
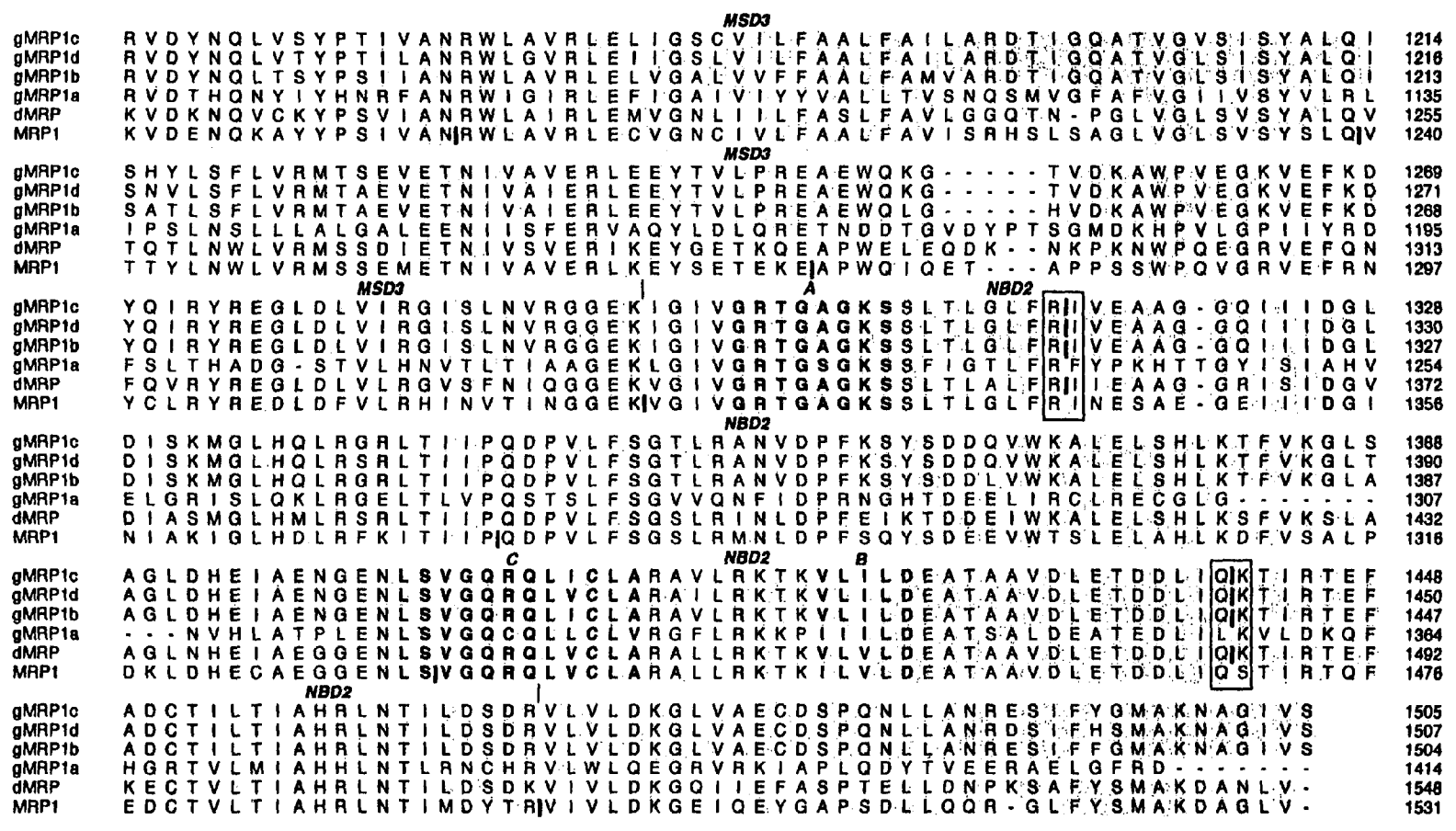

The present invention provides isolated nucleic acid molecules that comprise a nucleic acid sequence encoding dMRP or gMRP. The amino acid sequence of the protein encoded by dMRP or gMRP is provided in the Sequence Listing as SEQ ID NO: 1 and SEQ ID NOs: 2–5, respectively. As shown in FIG. 6, gMRP1a, gMRP1b, gMRP1c, and gMRP1d are identified as SEQ ID NOS: 2–5, respectively. SEQ ID NO: 1 identifies dMRP, and MRP1 is identified as SEQ ID NO: 6.

Those skilled in the art will recognize that the degenerate nature of the genetic code enables one to construct many different nucleic acid sequences that encode the amino acid sequences of SEQ ID NO: 1–5. Consequently, the constructions described below and in the accompanying examples for the preferred nucleic acid molecules, vectors, and transformants of the invention are illustrative and are not intended to limit the scope of the invention. All nucleotide and amino acid abbreviations used in this disclosure are those accepted by the United States Patent and Trademark Office as set forth in 37 C.F.R. §1.822(b) (1994).

The term "vector" refers to any autonomously replicating or integrating agent, including but not limited to plasmids, cosmids, and viruses (including phage), comprising a nucleic acid molecule to which one or more additional nucleic acid molecules can be added. Included in the definition of "vector" is the term "expression vector". Vectors are used either to amplify and/or to express deoxyribonucleic acid (DNA), either genomic or cDNA, or RNA (ribonucleic acid), which encodes dMRP or gMRP, or to amplify DNA or RNA that hybridizes with DNA or RNA encoding dMRP or gMRP.

The term "expression vector" refers to vectors, which comprise a transcriptional promoter (hereinafter "promoter"), and other regulatory sequences positioned to drive expression of a DNA segment that encodes dMRP or gMRP. Expression vectors of the present invention are replicable DNA constructs in which a DNA sequence encoding dMRP or gMRP is operably linked to suitable control sequences capable of effecting the expression of dMRP or gMRP in a suitable host. Such control sequences include a promoter, an optional operator sequence to control transcription, a sequence encoding suitable mRNA ribosomal binding sites, and sequences that control termination of transcription and translation. DNA regions are operably linked when they are functionally related to each other. For example, a promoter is operably linked to a DNA coding sequence if it controls the transcription of the sequence, or a ribosome binding site is operably linked to a coding sequence if it is positioned so as to permit translation.

The term "MRP inhibition activity" refers to the ability of a compound to inhibit the MRP activity of a host cell, thereby increasing the insecticidal activity of an insecticidal compound against said host cell.

In the present invention, dMRP or gMRP may be synthesized by host cells transformed with vectors that provide for the expression of DNA encoding dMRP or gMRP. The DNA encoding dMRP or gMRP can be the natural sequence or a synthetic sequence or a combination of both ("semi-synthetic sequence"). The in vitro or in vivo transcription and translation of these sequences results in the production of dMRP or gMRP. Synthetic and semi-synthetic sequences encoding dMRP or gMRP can be constructed by techniques well known in the art. See Brown et al. (1979) Methods in Enzymology, Academic Press, N.Y., 68:109–151. dMRP or gMRP-encoding DNA, or portions thereof, can be generated using a conventional DNA synthesizing apparatus, such as the Applied Biosystems Model 380A, 380B, 394 or 3948 DNA synthesizers (commercially available from Applied Biosystems, Inc., 850 Lincoln Center Drive, Foster City, Calif. 94404).

Owing to the natural degeneracy of the genetic code, the skilled artisan will recognize that a sizable yet definite number of nucleic acid sequences can be constructed that encode dMRP or gMRP. All such nucleic acid sequences are provided by the present invention. These sequences can be prepared by a variety of methods and, therefore, the invention is not limited to any particular preparation means. The nucleic acid sequences of the invention can be produced by a number of procedures, including DNA synthesis, cDNA cloning, genomic cloning, polymerase chain reaction (PCR) technology, or a combination of these approaches. These and other techniques are described by Maniatis, et al., *Molecular Cloning: A Laboratory Manual*, Cold Spring Harbor Press, Cold Spring Harbor Laboratory, Cold Spring Harbor, N.Y. (1989), or *Current Protocols in Molecular Biology* (F. M. Ausubel et al., 1989 and supplements). The contents of both of these references are incorporated herein by reference.

In another aspect, this invention provides the genomic DNA encoding dMRP or gMRP, which may be obtained by synthesizing nucleic acids encoding the desired portion of SEQ ID Nos. 1–5 or by following the procedure described in the Examples.

To effect the translation of dMRP or gMRP-encoding mRNA, one inserts the natural, synthetic, or semi-synthetic dMRP or gMRP-encoding DNA sequence into any of a large number of appropriate expression vectors through the use of appropriate restriction endonucleases and DNA ligases. Synthetic and semi-synthetic dMRP or gMRP-encoding DNA sequences can be designed, and natural dMRP or gMRP-encoding nucleic acid can be modified to possess restriction endonuclease cleavage sites to facilitate isolation from and integration into these vectors. Particular restriction endonucleases employed will be dictated by the restriction endonuclease cleavage pattern of the expression vector utilized. Restriction enzyme sites are chosen so as to properly orient the dMRP or gMRP-encoding DNA with the control sequences to achieve proper in-frame transcription and translation of the dMRP or gMRP molecule. The dMRP or gMRP-encoding DNA must be positioned so as to be in proper reading frame with the promoter and ribosome binding site of the expression vector, both of which are functional in the host cell in which dMRP or gMRP is to be expressed.

Expression of dMRP or gMRP can be accomplished in cells, such as *Saccharomyces cerevisiae*. Suitable promoter sequences for use with yeast hosts include the promoters for 3-phosphoglycerate kinase (found on plasmid pAP12BD (ATCC 53231) and described in U.S. Pat. No. 4,935,350, Jun. 19, 1990) or other glycolytic enzymes, such as enolase (found on plasmid pAC1 (ATCC 39532)), glyceraldehyde-3-phosphate dehydrogenase (derived from plasmid pHcGAPC1 (ATCC 57090, 57091)), hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Inducible yeast promoters have the additional advantage of transcription controlled by growth conditions. Such promoters include the promoter regions for alcohol dehydrogenase 2, isocytochrome C, acid phosphotase, degradative enzymes associated with nitrogen metabolism, metallothionein (contained on plasmid vector pCL28XhoLHBPV (ATCC 39475), U.S. Pat. No. 4,840,896), glyceraldehyde 3-phosphate dehydrogenase, and enzymes responsible for maltose and galactose utilization (GAL1 found on plasmid pRY121 (ATCC 37658) and on plasmid pPST5, described below). Suitable vectors and promoters for use in yeast expression are further described by R. Hitzeman et al., in European Patent Publication No. 73,657A. Yeast enhancers, such as the UAS Gal enhancer from *Saccharomyces cerevisiae* (found in conjunction with the CYC1 promoter on plasmid YEpsec—hI1 beta, ATCC 67024), also are advantageously used with yeast promoters.

A variety of expression vectors useful in the present invention are well known in the art. For expression in *Saccharomyces*, the plasmid YRp7, for example, (ATCC-40053, Stinchcomb et al., 1979, *Nature* 282:39; Kingsman et al., 1979, *Gene* 7:141; Tschemper et al., 1980, Gene 10:157) is commonly used. This plasmid contains the trp gene, which provides a selection marker for a mutant strain of yeast lacking the ability to grow in tryptophan, for example ATCC 44076 or PEP4-1 (Jones, 1977, Genetics 85:12).

Expression vectors useful in the expression of dMRP or gMRP can be constructed by a number of methods. For example, the cDNA sequence encoding dMRP or gMRP can be synthesized using DNA synthesis techniques, such as those described above. Such synthetic DNA can be synthesized to contain cohesive ends that allow facile cloning into an appropriately digested expression vector. For example, the cDNA encoding dMRP or gMRP can be synthesized to contain Notl cohesive ends. Such a synthetic DNA fragment can be ligated into a Notl-digested expression vector such as pYES-2 (Invitrogen Corp., San Diego Calif. 92121).

The techniques involved in the transformation of yeast cells, such as *Saccharomyces cerevisiae* cells, are well known in the art and may be found in such general references as Ausubel et al., Current Protocols in Molecular Biology (1989), John Wiley & Sons, New York, N.Y. and supplements. The precise conditions under which the transformed yeast cells are cultured is dependent upon the nature of the yeast host cell line and the vectors employed.

Nucleic acid, either RNA or DNA, which encodes dMRP or gMRP, or a portion thereof, is also useful in producing nucleic acid molecules useful in diagnostic assays for the detection of dMRP or gMRP mRNA, dMRP or gMRP cDNA, or dMRP or gMRP genomic DNA. Further, nucleic acid, either RNA or DNA, which does not encode dMRP or gMRP, but which nonetheless is capable of hybridizing with dMRP or gMRP-encoding DNA or RNA is also useful in such diagnostic assays. These nucleic acid molecules can be covalently labeled by known methods with a detectable moiety, such as a fluorescent group, a radioactive atom, or a chemiluminescent group. The labeled nucleic acid is then used in conventional hybridization assays, such as Southern or Northern hybridization assays, or polymerase chain reaction assays (PCR), to identify hybridizing DNA, cDNA, or RNA molecules. PCR assays can also be performed using unlabeled nucleic acid molecules. Such assays can be employed to identify dMRP or gMRP vectors and transformants and in in vitro diagnosis to detect dMRP or gMRP-like mRNA, cDNA, or genomic DNA from other organisms.

Compounds with demonstrated insecticidal activity can be potentiated by an MRP inhibitor such that the insecticidal activity of these compounds is extended to previously resistant species. To identify compounds useful in such combination the present invention provides an assay method for identifying compounds with *Anopheles gambiae* or *Drosophila melanogaster* MRP inhibition activity. Host cells that express dMRP or gMRP provide an excellent means for the identification of compounds useful as inhibitors of *Anopheles gambiae* or *Drosophila melanogaster* MRP activity. Generally, the assay utilizes a culture of a cell transformed with a vector that provides expression of dMRP or gMRP. The expression of dMRP or gMRP by the host cell enables the host cell to grow in the presence of an insecticidal compound to which the cell is sensitive to in the untransformed state. Thus, the transformed yeast cell culture is grown in the presence of i) an insecticidal agent to which the untransformed cell is sensitive, but to which the transformed host cell is resistant, and ii) a compound that is suspected of being an MRP inhibitor. The effect of the suspected MRP inhibitor is measured by testing for the ability of the insecticidal compound to inhibit the growth of the transformed cell. Such inhibition will occur if the suspected *Anopheles gambiae* or *Drosophila melanogaster* MRP inhibitor blocks the ability of dMRP or gMRP to prevent the insecticidal compound from acting on the cell. The *Drosophila* Schneider cell can be used for example. The *Drosophila* Schneider cell line, for example, can be used.

Oligonucleotides are provided by this invention, which are specifically hybridizable with nucleic acids encoding the dMRP and gMRP. Also provided are methods of using the oligonucleotides of the invention in methods of modulating the expression of MRP genes, inhibition of which leads to inhibition of the synthesis of dMRP and gMRP, and thereby inhibits cellular multidrug resistance. Such inhibition is desirable for preventing or modulating the development of multidrug resistance in an insect. Modified derivatives of the oligonucleotides of the invention, such as chimeras and conjugates (e.g., of an oligonucleotide and a lipophilic moiety, such as cholesterol), are also contemplated by the invention. The biological activity and cellular uptake of oligonucleotides is enhanced by such modifications.

In accordance with the present invention oligonucleotides are provided, which specifically hybridize with nucleic acids encoding an dMRP or gMRP. Certain oligonucleotides of the invention are designed to bind either directly to mRNA transcribed from, or to a selected DNA portion of, dMRP or gMRP, thereby modulating the amount of protein translated from dMRP or gMRP mRNA or the amount of mRNA transcribed from dMRP or gMRP, respectively.

Oligonucleotides can comprise nucleotide sequences sufficient in identity and number to effect specific hybridization with a particular nucleic acid. Such oligonucleotides are commonly described as "antisense." Antisense oligonucleotides can be used as research tools and diagnostic aids. MRP genes encoding dMRP or gMRP are particularly useful for this approach. Inhibition of the expression of such MRP genes leads to inhibition of the synthesis of dMRP or gMRP and thereby inhibits cellular multidrug resistance. Such inhibition is desirable for preventing or modulating the development of multidrug resistance in an insect. The specific hybridization exhibited by the oligonucleotides of the present invention can be used for assays, purifications, cellular product preparations and in other methodologies that will be appreciated by persons of ordinary skill in the art.

Methods of modulating the expression of dMRP and gMRP comprising contacting insects with oligonucleotides specifically hybridizable with an MRP gene are herein provided. These methods are useful as a consequence of the association between MRP expression and the multidrug resistance of cells. These methods are also useful as tools, for example, in the detection and determination of the role of dMRP and gMRP expression in various cell functions and physiological processes and conditions, and for the diagnosis of conditions.

The present invention employs oligonucleotides for use in antisense inhibition of the function of RNA and DNA encoding proteins. The present invention also employs oligonucleotides that are designed to be specifically hybridizable to DNA or messenger RNA (mRNA) encoding dMRP and gMRP and ultimately modulating the amount of such proteins transcribed from their respective MRP genes. Such hybridization with mRNA interferes with the normal role of mRNA and causes a modulation of its function in cells. The functions of mRNA to be interfered with include all vital functions, such as translocation of the RNA to the site for protein translation, actual translation of protein from the RNA, splicing of the RNA to yield one or more mRNA species, and possibly even independent catalytic activity which may be engaged in by the RNA. The overall effect of such interference with mRNA function is modulation of the expression of such dMRP and gMRP. In the context of this invention, "modulation" means either an increase (stimulation) or a decrease (inhibition) in the expression of a gene. In the context of the present invention, inhibition is the preferred form of modulation of gene expression.

Oligonucleotides comprise nucleotide sequences sufficient in identity and number to effect specific hybridization with a particular nucleic acid. For example, antisense oligonucleotides, which are able to inhibit gene expression with exquisite specificity, are useful for elucidating the function of particular genes, for example, to distinquish between the functions of various members of a biological pathway. This specific inhibitory effect has, therefore, been harnessed for research use.

The oligonucleotides in accordance with this invention preferably comprise from about 8 to about 30 nucleotides. It is more preferred that such oligonucleotides comprise from about 15 to 25 nucleotides.

The present invention employs oligonucleotides targeted to nucleic acids encoding dMRP and gMRP, and oligonucleotides targeted to nucleic acids encoding such proteins. Kits for detecting the presence or absence of MRP expression can also be prepared. Such kits include an oligonucleotide targeted to an MRP gene encoding a dMRP and gMRP. Such kit and assay formats are known in the art.

"Complementary," as used herein, refers to the capacity for precise pairing between two nucleotides. For example, if a nucleotide at a certain position of an oligonucleotide is capable of hydrogen bonding with a nucleotide at the same position of a DNA or RNA molecule, then the oligonucleotide and the DNA or RNA are considered to be complementary to each other at that position. The oligonucleotide and the DNA or RNA are complementary to each other when a sufficient number of corresponding positions in each molecule are occupied by nucleotides which can hydrogen bond with each other.

Thus, "specifically hybridizable" and "complementary" are terms which are used to indicate a sufficient degree of complementarity or precise pairing such that stable and specific binding occurs between the oligonucleotide and the DNA or RNA target. It is understood in the art that an oligonucleotide need not be 100% complementary to its target DNA sequence to be specifically hybridizable. An oligonucleotide is specifically hybridizable when binding of the oligonucleotide to the target DNA or RNA molecule interferes with the normal function of the target DNA or RNA to cause a loss of utility, and there is a sufficient degree of complementarity to avoid non-specific binding of the oligonucleotide to non-target sequences under conditions in which specific binding is desired, i.e., under physiological conditions in the case of in vivo assays or therapeutic treatment, or in the case of in vitro assays, under conditions in which the assays are performed.

DROSOPHILA MELOGANSTER

Materials and Methods

Genomic DNA Extraction

Adult D. melanogaster(1.5 g) were homogenized in liquid nitrogen. After addition of 7 ml of lysis buffer (100 mM Tris pH 8, 50 mM NaCl, 50 mM EDTA, 1% SDS, 0.15 mM spermine, and 0.5 mM spermidine) plus proteinase K (100 μg/ml), the homogenate was mixed slowly at 37° C. for 2 H. Following extraction with phenol (1×), with chloroform (1×) and dialysis overnight at 4° C. against TEN buffer (500 mM Tris pH 8, 10 mM EDTA, 10 mM NaCl), the DNA was treated with RNase (DNase free, 100 ng/ml) at 37° C. for 1 H. It was then extracted once with phenol/chloroform (1:1), with chloroform, and dialyzed overnight at 4° C. against TE buffer (10 mM Tris pH 8, 1 mM EDTA). The DNA was then precipitated with ⅒ volume of 3 M sodium acetate and two volumes absolute ethanol, collected, redissolved, and its final concentration was estimated on an agarose gel. DNA was prepared from larvae and pupae by the same method.

Southern Blots

DNA (10 μg) was digested with either BamHI or HindIII and the fragments were separated by electrophoresis on a 0.8% agarose gel. Following transfer to Hybond-N nylon membrane and fixation, hybridization was carried out at 65° C. (in 1% BSA, 0.25 M $NaH_2PO_4$ pH 7.2, 1 mM EDTA, 150 μg/ml salmon sperm DNA) with a PCR-derived dMRP probe covering 378 bases (forward primer: GATCCGTT-TATTTCCTTGCCGC (SEQ ID NO: 16); reverse primer: TCCAGGGCAGTGATTACCAGT (SEQ ID NO: 17)). After hybridization, the blot was washed (in 40 mM $NaH_2PO_4$ pH 7.2, 1% SDS, and 1 mM EDTA) 1× at RT and 2× at 65° C.

Reverse Transcriptase-PCR (RT-PCR)

Extraction of Total RNA and cDNA Synthesis

Total RNA was Isolated From 0–4H Eggs, 12–24H Eggs, Pupae, and Adult

D. melanogaster using Tri Reagent (Sigma) according to the manufacturer's instructions. The cDNA was synthesized in a 20 μl reaction mix containing 10 μg of total RNA, 1×AMV reverse transcriptase buffer (Promega), 10 U of AMV reverse transcriptase (Promega), 40 U of RNasin (Promega), 4 μg of random hexanucleotide primers (Genset), and 1 μM of each dNTP (Pharmacia). The reaction was incubated at 37° C. for 1 H, followed by 95° C. for 5 min.

Amplification of Exon 4

The first PCR used primers Dr2for/Dr6rev (Table 2) and 1 μl of cDNA as template. The cycling conditions were 94° C. (3 min) for 1 cycle; 94° C. (45 sec), 60° C. (30 sec) and 72° C. (90 sec) for 35 cycles; 72° C. (10 min) for 1 cycle. This amplified product was used as template (0.5 μl) for a second PCR with the same cycling conditions with primer set specific for exon 4a or 4b (Table 2).

Amplification of Exon 8

Essentially the same conditions as those described for exon 4 were used for exon 8 containing cDNA, except that the first primer set was DR17/DR18 (Table 2) and the annealing temperature was 55° C. After electrophoresis on a 1% agarose gel, the amplified DNA was excised, purified using a Jetsorb kit (Genomed) and used as template for a second PCR with the same cycling conditions but with the exon 8 primer sets designated in Table 2.

DNA Sequencing

PCR-amplified DNA was purified using the Qiaquick PCR purification kit (Qiagen) and sequenced using an ABIprism 310 automated DNA sequencer. The cDNA clone SD07655 was sequenced directly from the plasmid after amplification in *E. coli* DH5α bacteria and extraction with a Qiafilter Plasmid Midi kit (Qiagen). Kits were used according to the manufacturer's instructions.

Sequence Analysis

The BLAST searches were done using the Washington University (Gish, W., 1996–2002<<http://blast.wustl.edu>>) and the NCBI (Altschul et al., 1997) versions of BLAST. ClustalW (Higgins & Sharp, 1988) or PileUp from the Wisconsin Package programs licensed from the Genetics Computer Group (GCG) was used for sequence alignments. The TMAP and Needle programs, used for transmembrane domain search and pairwise sequence comparisons, are part of the EMBOSS software package from EMBL. The software, except for the GCG package, were accessed through the Institut Pasteur web site at <http//:bioweb.pasteur.fr>. Many common DNA and protein sequence manipulations were done with DNA Strider, a Macintosh DNA program (Marck, 1988).

Characterization of the *Drosophila* MRP

Before the release of the annotated *Drosophila* genome, the amino acid sequence of human MRP1 was compared to the available genomic sequences using the TBLASTN program through the Berkeley *Drosophila* Genome Project (BDGP) web site (http://www.fruitfly.org). The BAC clone AC005819 was identified as containing a sequence that could code for a protein having high similarity with the human MRP1. The concerned region of the clone was then scanned against the available *Drosophila* Expressed Sequence Tags (ESTs), and several cDNA sequences were detected. Clone SDO7655 was selected, obtained from Research Genetics (Huntsville, Ala., USA) and sequenced. During the preparation of this report, BDGP has independently released the SD07655 cDNA sequence, accession number AY069827, for gene FBgn0032456. The gene encoding SD07655 has been given the name CG6214 by the BDGP.

When the deduced protein sequence of SD07655 was compared to those of all predicted *Drosophila* proteins, it naturally was most similar to the predicted product of gene CG6214, the gene from which SD07655 was transcribed. The next best predicted protein, the CG14709 product, has a blastp bit score of only 747 compared to the 2,937 score for that of CG6214. Likewise, if the human MRP1 amino acid sequence is used as the query, the bit score with our deduced SD07655 amino acid sequence (1,484) is twice as high as with the next best sequence derived from gene CG14709 (770). These results argue that CG6214 is a unique gene and is the *Drosophila* homolog the most related to human MRP1. This proposal was confirmed by a Southern blot of BamHI- or HindIII-digested genomic adult fly DNA probed with a SD07655 PCR product (data not shown).

Figure 1:
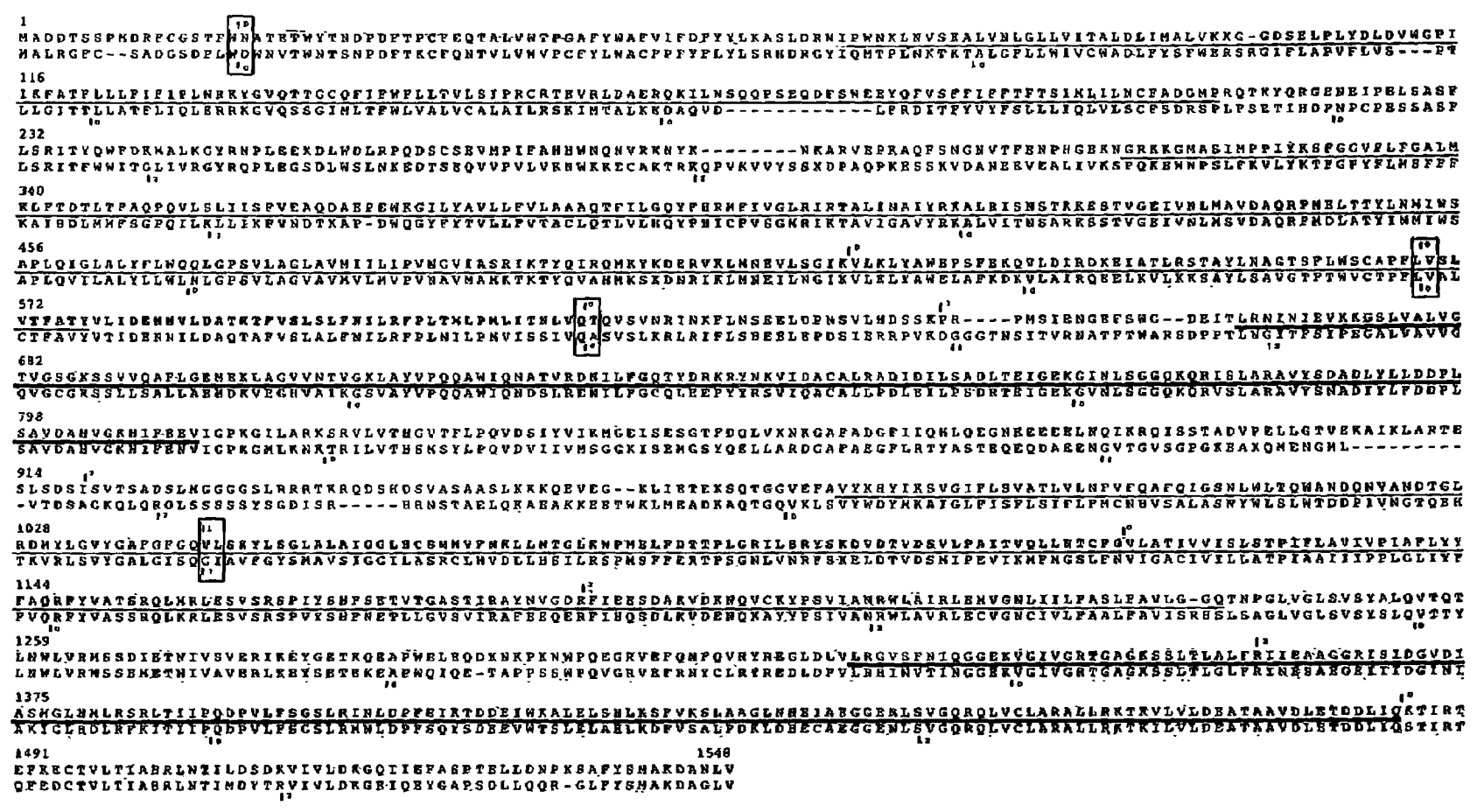

The deduced 1548 amino acid sequence generated from the SD07655 nucleotide sequence is shown in FIG. 1. The actual initiation methionine is not known, but the selected one was chosen based on a positional comparison with animal members of the MRP family, and because it was preceded by stop codons in all three ORFs, as well as having a consensus A at position −3 and a G at position +4, as discussed by Kozak (1996). The deduced amino acid sequence of this *Drosophila* cDNA produced an alignment with 48% identity and 64.5% similarity with the human MRP1 protein, and more than 44% identity and 60% similarity with several other MRPs (Table 1).

Figure 3:
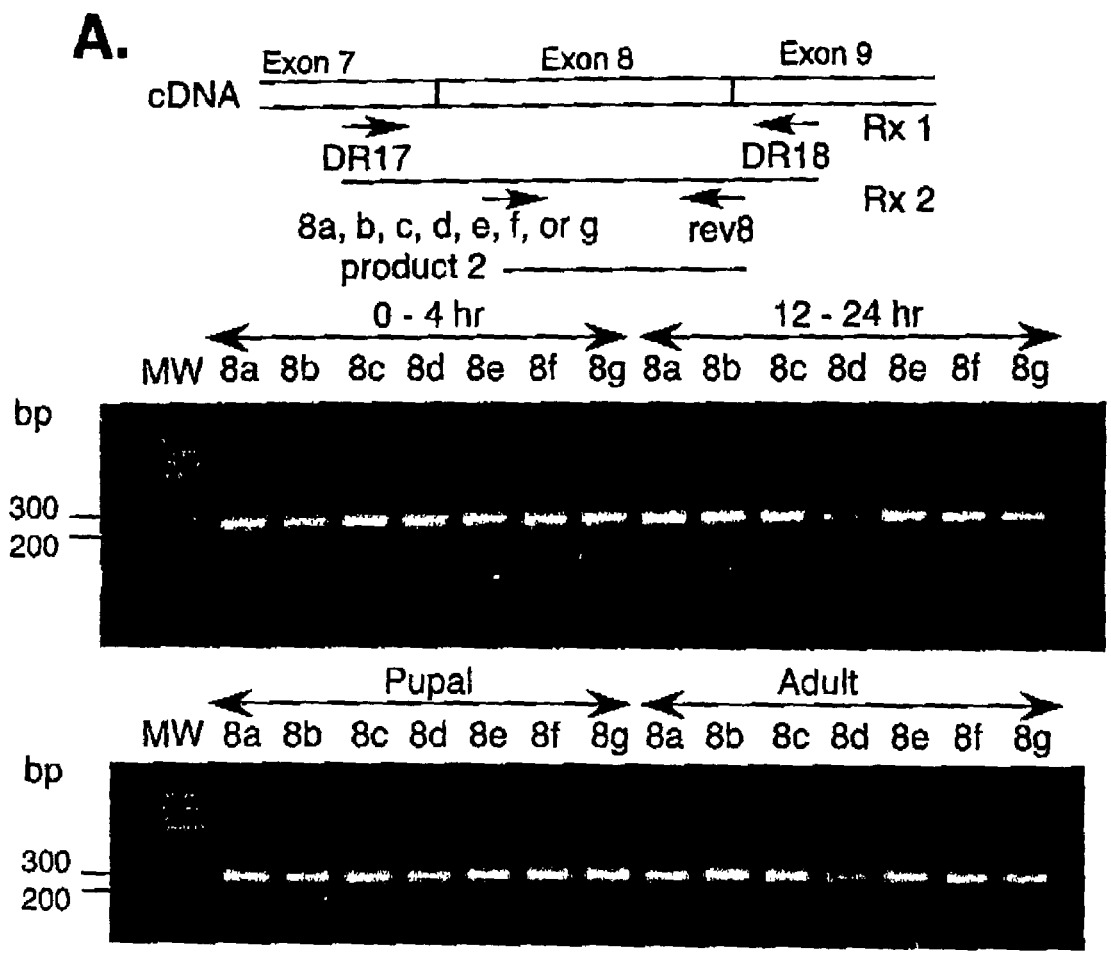
FIG. 3. Expression of exons 4 and 8 variants in cellular RNA. Total cDNA was prepared as described in Materials and Methods. A first nonspecific PCR amplification of the exon 8 (A) or 4 (B) was generated using primers in neighboring exons. The presence of cDNA from a specific exon was tested using one nonspecific primer and a second primer that represented a specific sequence in the exon being tested. All of the primer sequences and the predicted product sizes are listed in Table 2. (A) The exon 8 region of the cDNA was amplified using primers DR17/DR18. The specific amplifications used primer rev8 and the specific primer 8a-8g. (B) The MRP exon 4 region of the cDNA was amplified with primers Dr2for and Dr6rev. The exon 4 specific reactions used primer sets Dr2for/Dr4arev (lanes A, B, C) or Dr2for/Dr4brev (lanes D, E, F). The DNA targets were the product of reaction Dr2for/Dr6rev (lanes A and D), cDNA SD07655 (lanes B and E), Anopheles gambiae genomic DNA (lanes C and F). The PCR products were separated on a 1% agarose gel using the molecular weight marker (MW) SmartLadder SF (Eurogentec; Seraing, Belgium).
Figure 3:
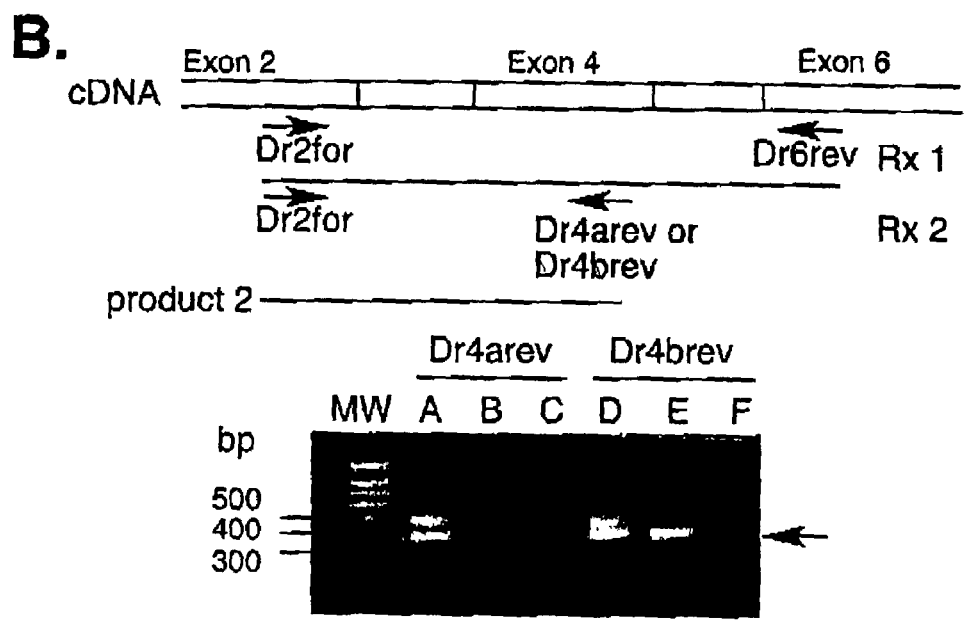

Topology predictions and comparison with other characterized MRPs point to six main regions on the mRNA, corresponding to the following parts of the protein: three MSDs (MSD 1–3), two NBDs (containing motifs A, C, B), and a linker region connecting NBD1 to MSD3 (FIGS. 1 and 3). The NH2-proximal MSD1 could span the membrane three times, while MSDs 2 and 3 may each contain four transmembrane helices, and precede NBDs 1 and 2, respectively. As seen in the alignment with the human MRP1 (FIG. 1), the similarity is especially prominent in the NBDs (706–855 and 1368–1527) and to a lesser extent in MSDs 2 and 3 (355–619 and 1020–1281). By contrast, MSD1 (110–254) and the linker region, between NBD1 and MSD3, are poorly conserved, a usual feature in MRPs. The Walker A and B boxes are easily identified in the NBDs, as well as the ABC signature. As with other MRPs, the first NBD of dMRP is 13 amino acids smaller than that of P-glycoproteins (Cole et al., 1992; Deeley & Cole, 1997).

A simple comparison of the SD07655 cDNA and the genomic sequences defined a gene that spans slightly more than 22 kbp and contains 12 exons. Closer examination showed that exons 4 and 8 are represented by two and seven similar potential exons, respectively. FIG. 2 graphically depicts the predicted relationship between the cDNA and genomic sequences. This arrangement predicts a 12 exon cDNA including one copy each of the exon 4 and 8 variants as is seen with cDNA SD07655. The only important differences between this model and the FlyBase annotation are the inclusion of two copies of exon 4 in their predicted sequence, plus the predicted use of exon 8a rather than exon 8d, present in cDNA SDO7655. Their use of exon 8a is justified by the occurrence of EST LD28149, which begins in that exon sequence.

To assess which of the predicted exon 4 and 8 variants are used in mRNA, their expression was measured by a nested RT-PCR technique (Materials and methods, section 2.3). FIG. 3 shows that all seven alternative versions of exon 8, and the two variants of exon 4 were detected at all life stages tested, suggesting that use of the different exons is not developmentally regulated. Importantly, the sizes of the PCR products are those expected if only one copy of each exon is included in the cDNA. The accuracy of the amplification was verified by purification and sequencing of the products. In the case of exon 4, each product had a band slightly larger than the main band after the second PCR, even when the first PCR product was purified. Although we can not explain this phenomenon, sequencing the total product in both directions unequivocally resulted in the predicted sequence, either 4a or 4b.

Analysis of Intron-Exon Boundaries

To determine the intron-exon borders, the cDNA and genomic sequences were compared. The sizes of the introns and exons and their locations are shown in Table 3 along with the intron-exon junction sequences. The size of the exons varies from 85 bp for exon 5 to 1,512 bp for exon 2, with an average around 340 bp. The mean size for the introns is 867 bp, the largest being introns 13 and 18 which are 4,965 bp and 4,791 bp, respectively. The shortest intron is number 17 with 59 bp. Compared to the human MRP1 organization, the Drosophila exons are larger and the introns smaller (Grant et al., 1997). The intron-exon boundaries (Table 3) are in accordance with those of other eukaryotic genes, especially those of human MRP1. The acceptor is characterized by a (t/c)ag sequence in 84% of the cases, exons 4a and 8b being the only exceptions with an aag sequence. The splice donor sequences are G/gt(g/a)a(g/t), with a G in 83%, gt(g/a) in 100%, a in 78%, and (g/t) in 83% of the cases. Of the 18 introns, 13 (72%) are class 0, 2 (11%) are class 1, and 3 (17%) are class 2. In comparison, MRP1 introns are class 0 in 63% of the cases, 10% are class 1, and 27% are class 2. This clearly demonstrates a mutual bias toward class 0 introns in these genes, though MRP1 uses more class 2 introns than dMRP. The importance of this difference is difficult to interpret, nevertheless, it is interesting to note that four splice junctions and their class are conserved between the two genes (FIG. 1). The variable exon 4, located just before the NBD1 region, has been conserved between the two genes based on both their splice junctions, conserved amino acid sequence and exon length. Also, the initial dMRP exon 8 splice junction has been conserved in human MRP1 despite the relative divergence in this region.

Comparison of the Variable Exon Encoded Sequences

Six of seven exon 8 variants encode a 74 amino acid peptide while exon 8e encodes one additional amino acid. Likewise, the two exon 4 variants are the same length and use the same splice junction types. Alignment of the amino acid sequences encoded by the different exon 4 variants with the corresponding sequences from human MRPs 1–3 and the *D. melanogaster* sulphonylurea receptor (SUR) are shown in FIG. 4A. The two dMRP peptides are nearly identical in their N-terminal third, but the 4a derived peptide varies extensively from both the 4b and the human sequences in the otherwise highly conserved middle third of the peptide. This pattern suggests that conserved amino acids 18–37 may be important in normal MRP function and that the variation in this region of 4a gives the protein new properties.

When exon 8 variation is examined (FIG. 4B), there is a highly conserved region from amino acids 30–61 with the most divergence in variant 8e. The "FF" motif at positions 36–37 in the alignment is highly conserved in all the human sequences as well as in SUR and Pfam, the Protein family database consensus sequence (Bateman et al., 2002), but is only maintained in variants 8e and 8f. On the other hand, the exon 8 variants favor a Leu or Met in place of the second Phe. The extremities of the region are relatively divergent amongst all the proteins, suggesting that sequence conservation is less important in these regions.

To clarify the level of sequence similarity between the exon 8 variants and the corresponding region of other related proteins, a dendrogram was constructed using the UPGMA method on a matrix calculated with the PUZZLE program (Strimmer & von Haeseler, 1996). The dendrogram (FIG. 4C) shows the exon 8 heterogeneity: variants 8a, 8b, 8c, and 8d group together while 8g clusters with MRP2, and 8f and 8e are separated from the others. The Figure shows that while overall the Drosophila protein is very similar to human MRP1, in the exon 8 encoded region there is a great deal of diversity. This diversity could be related to the different substrates encountered by these transporters in their respective environments.

Conclusions

While alternative splicing has previously been described in the human MRPs, those cases differ from the type of splicing described in this article since previous reports detail the deletion of a terminal exon from the major product (Fromm et al., 1999; Grant et al., 1997) or the use of alternate transcriptional start sites (Bera et al., 2001; Suzuki et al., 2000). In the case of dMRP, the variants are produced by the "choice" of one exon among several possibilities for two internal regions of the protein. This process, novel in MRPs, could enable 14 different forms of the *Drosophila* protein.

Exon duplication is a mechanism for the evolution of protein function, and in the case of the dMRP the duplication and variation of exons 4 and 8 surely provide MRP proteins with new properties. These alterations currently provide a series of isoforms with limited, defined changes in the large protein scaffold. Understanding the substrates and physiology of the different isoforms should provide new information on the role of these variable regions in MRP function in the fly, but also in human (and other organisms) for which the corresponding regions should retain attention in future structure/function studies.

The capacity to produce a range of transporters with different specificities could be important for survival of the fly, by reducing the toxicity of an enlarged number of natural products encountered during its life. A function as important as protection from environmental toxins should not be based on a single molecule, but rather on a network of interacting enzymes with different reactivities. MRPs have a preference for glutathione conjugated substrates, and in insects glutathione S (GS)-transferases have been shown to be involved in insecticide metabolism (Tang & Tu, 1994; Ranson et al., 1997; Hemingway & Ranson, 2000). Thus, MRPs could act together with the GS-transferases to confer insecticide resistance, by coupling toxin/conjugate efflux (MRP) to toxin conjugation (GST). This hypothesis is in line with the synergistic effect of an overexpression of both a GS-transferase and MRP1, leading to high-level resistance to the cytotoxic action of several drugs in a human cell line (Morrow et al., 1998a; 1998b).

*ANOPHELES GAMBIAE*

Materials and Methods

Screening of the cDNA Library and Sequencing of the cDNAs

The cDNA library from *Anopheles gambiae* G3 fourth instar larvae in λ Zap express vector (Stratagen) was kindly provided by Dr Hans-Michael Müller. 300,000 independent clones were transferred to Hybond N+ membranes (Amersham) and screened for gMRP1a–d by use of two PCR derived probes specific to gMRP1a (primer set gMRP1 for/gMRP1 rev, 645 bp) and gMRP1b–d (primer set MRP104/MRP105, 773 bp). Nucleotide sequences of the primers are shown in Table 1.

TABLE 1

Identity and similarity between dMRP and some other MRPs[a]

| | Percent identity/similarity | | | | |
|---|---|---|---|---|---|
| | MRP1 | MRP2 | MRP3 | CeMRP1 | Dsur |
| dMRP | 48/64.5 | 44.7/63.4 | 47.7/63.6 | 44.1/61.2 | 23.7/38.0 |
| MRP1 | | 48.7/67.0 | 57.1/74.1 | 46.7/64.6 | 24.5/38.3 |
| MRP2 | | | 47.2/66.3 | 42.3/61.6 | 23.4/37.8 |
| MRP3 | | | | 44.3/63.1 | 24.1/38.0 |
| CeMRP1 | | | | | 24.4/38.1 |

[a]Percent identity and similarity between the sequence pairs was calculated using the Needle program. The amino acid sequences are as follows: dMRP, *D. melanogaster*, MRP1, human (NM_004996); MRP2, human (NP_005836); MRP3, human (Y17151); CeMRP1, *C. elegans* (AB023045); Dsur, *D. melanogaster sulfonylurea* receptor (NG_000795).

The probes were $^{32}$P-labeled (ICN) by random priming, and the library was screened following the Stratagen Zap express vector kit instructions. Forty eight positive plaques were purified by two rounds of screening and identified as containing gMRP1a, b, c or d by PCR with primers specific to each sequence (gMRP1for/gMRP1 rev, gMRP2for/gMRP234rev, gMRP3for/gMRP234rev, and gMRP4for/gMRP234rev, respectively; Table 1). The size of the cDNA inserts was analysed by PCR with T7 and T3 universal primers. The cDNA inserts from seven positive clones that were longer than 5 kbp were sub-cloned into the pBK-CMV vector by in vivo excision from the recombinant λ Zap express vector following the manufacturer's instructions. Four cDNA inserts representing each of the gMRPs were then sequenced by Genome Express (Paris, France).

Sequence Analysis

The ClustalW (Higgins & Sharp, 1988) program was used for sequence alignments. Tmap and Predictprotein were used for transmembrane domain search and Needle for pairwise sequence comparisons. Tmap and Needle are part of the EMBOSS software package from EMBL. The BLAST searches were done using the Washington University version of BLAST (Altschul et al., 1997). The softwares, except for the Predictprotein server (http://dodo.bio-c.columbia.edu/pp), were accessed through the Institut Pasteur web site (http//:bioweb.pasteur.fr).

Extraction of Total RNA and cDNA Synthesis

Total RNA was isolated from adult mosquitoes using Tri Reagent (Sigma) according to the manufacturer's instructions. Total RNA from tissues (salivary glands, Malpighi tubules, digestive tract from midgut to hindgut, heads and thorax) was isolated using a protocol conceived for small tissue amounts: tissues were homogenized in liquid nitrogen before dissolution in 200 µl of RNABle (Eurobio). Twenty µl of chloroform were added and samples were incubated on ice for 15 min after vortexing. They were centrifuged 45 min at 15000 g and 4° C. Eighty µl of supernatant were recovered and mixed to two volumes of 100% EtOH. After 2 min of incubation at RT, they were centrifuged 5 min at 15000 g. Pellet was washed in 180 µl of 70% EtOH, and finally recovered in 22 µl of DEPC H$_2$O. The cDNA was synthesized in a 20 µl reaction mix containing 10 µg of total RNA, 1×AMV reverse transcriptase buffer (Promega), 10 U of AMV reverse transcriptase (Promega), 40 U of RNasin (Promega), 4 µg of random hexanucleotide primers (Genset), and 1 µM of each dNTP (Pharmacia). The reaction was incubated at 37° C. for 1 H, and stopped at 95° C. for 5 min.

Amplification on cDNA

Primers used for specific amplification of gMRP1a–d on total cDNA are shown in Table 1. The cycling conditions were 94° C. (2 min) for 1 cycle; 94° C. (1 min), 56° C. (1 min 30 sec) and 72° C. (2 min) for 35 cycles (except with the actin primers, for which only 25 cycles were processed); 72° C. (10 min) for 1 cycle.

Identification of *A. gambiae* MRPs

Before the consortium was decided on the systematic study of the *A. gambiae* genome, sequences already available at the Genoscope (Evry, France) were used in a comparison to the human MRP1 protein sequence, and the entirely sequenced BAC clone 22C14, containing four successive sequences with similarity to that of the human were so identified. This BAC had been previously mapped to chromosome arm 3R, on position 30D.

Sequencing of the cDNAs and Analysis of Intron-Exon Boundaries

In view of identifying cDNAs specific to each of the four gMRP genes, we screened a cDNA library of *Anopheles gambiae* was screened as described above. The cDNAs selected from the library were systematically sequenced for comparison with the genomic sequence available from BAC 22C14. The resulting gene structure for each gMRP is shown schematically in FIG. 1. Length of exons and introns, their location on the gene and intron-exon junctions are shown in Table 2.

TABLE 2

PCR Primers and Their Expected Product Sizes

| SEQ ID NO: | Primer name | Primer sequence | Size of PCR product expected with Dr2for (bp) | Size of PCR product expected with DR17 (bp) | Size of PCR product expected with rev8 (bp) |
|---|---|---|---|---|---|
| 18 | Dr2for | AGTGATTGCCAGTCGCATCA | | | |
| 19 | Dr6rev | GCCGTTCTCAATGCTCATTG | 493 | | |
| 20 | Dr4arev | CTCGGCTATGTCAACACTCA | 382 | | |
| 21 | Dr4brev | TTGCACCAGGTTGGTGATCA | 382 | | |
| 22 | DR17 | AACGATCAAAATGTCGCC | | | |
| 23 | DR18 | CACGAATAGTCGATGCTCC | | 500 | |
| 24 | rev8 | GGGAATTCGCGTGGACAGACTAAT | | | |
| 25 | 8a | GGGAATTCGCGACGAACTTCTTCTC | | | 269 |
| 26 | 8b | GGGAATTCTTACCTCGTACTTCTTTTG | | | 269 |
| 27 | 8c | GGGAATTCTTGTTACAGGGTATCTATC | | | 269 |
| 28 | 8d | GGGAATTCCTATCCAAATATTTATCGGGG | | | 269 |
| 29 | 8e | GGGAATTCGTTTCACGTCATTCTTTTC | | | 272 |
| 30 | 8f | GGGAATTCGTCTTTGCAATTACGGCGC | | | 269 |
| 31 | 8g | GGGAATTCGTGTGCTAGCCTACTTTGC | | | 269 |

The sizes proposed for the first exons are only putative, as they correspond to the longest cDNA found in the library, which appears consistent with a clustal W alignment of deduced amino acid sequences of several MRPS, and presents a favorable environment for the putative first methionine (Kozak, 1996).

For gMRP1b and gMRP1d, sequences could be amplified by RT-PCR upstream of the longest cDNA, and no size was proposed for the first exon in this case The longest exon is exon 4 for gMRP1a (3638 bp), exon 2 for gMRP1b (2144 bp), exon 3 for gMRP1c (1497 bp), and exon 3 as well for gMRP1d (1497 bp). The smallest seems to be exon 1 (165 bp) for gMRP1a, exon 4 for gMRP1b (382 bp), exon 4 for gMRP1c (77 bp), and exon 4 for gMRP1d (80 bp). The mean size of exons is 1151 bp, 1119 bp, 671 pb, and 726 bp for gMRP1a, gMRP1b, gMRP1c, and gMRP1d, respectively. Introns are small in all four gMRPs, with mean sizes of 170 bp, 69 bp, 70 bp, and 80 bp for gMRP1a, gMRP1b, gMRP1c, and gMRP1d, respectively.

These data contrast with those of the human MRP1 (Grant et al., 1997), for which exons are small (not greater than 311 bp), while introns are very large (from one to several kbp). Even when compared to the Drosophila structure, the gMRPs contrast by the fact that their exons are longer than their introns. Nevertheless, intron-exon boundaries share the characteristics of other eukaryotes. The acceptor sequence is characterized by a (t/c)ag motif, and the splice donor sequence is gt(g/a)ag(t/a), with a gt in 100%, (g/a) in 95%, and ag(t/a) in 74% of the cases. Introns 1 and 2 of gMRP1a are of class 0, while intron 3 is of class 2. Among the four introns in gMRP1b, two are of class 0, and 2 of class 2. Three of the six introns of gMRP1c are of class 2, two are of class 0, and one of class 1. In gMRP1d, the pattern is identical to that of gMRP1c. Interestingly, the class 2 introns are predominant in these genes, while MRP1 and dMRP have more class 0 introns. A common feature, however, is the few number of class 1 introns (only one in gMRP1c and gMRP1d, and none in gMRP1a and gMRP1b). Analysis on aligned sequences shows conservation of splice site locations and class of introns between the four gMRPs (FIG. 1), some data consistent with a common origin of these copies by duplication of an ancestor gene. Only the first splice site in gMRP1a has no equivalent in the three other gMRPs. gMRP1c and gMRP1d share exactly the same splice site, thus reinforcing the similarity between these two forms, which are also the closest at the level of their nucleotide sequence (Table 3).

TABLE 3

Intron-exon organization of the Drosophila dMRP gene

| Exon | | 3' acceptor[a] (SEQ ID NOS 32–49, respectively, in order of appearance) | exon location[b] | 5' donor SEQ ID NOS 50–67, respectively, in order of appearance | Intron | | |
|---|---|---|---|---|---|---|---|
| n° | Size (bp) | | | | n° | Phase | Size (bp) |
| 1 | 181 | | -127 · 54 | TTCTGG/gtgagt | 1 | 0 | 74 |
| 2 | 1512 | gaacag/AACGCA | 129 · 1640 | ATTAAG/gtgagt | 2 | 0 | 135 |
| 3 | 138 | acatag/GTGCTC | 1776 · 1913 | TTCCTG/gtaaga | 3 | 0 | 128 |
| 4a | 147 | acaaag/GTTTCC | 2042 · 2188 | GCCGAG/gtacag | 4 | 0 | 146 |
| 4b | 147 | ttttag/GTTTCA | 2335 · 2481 | GTGCAA/gtaagt | 5 | 0 | 800 |
| 5 | 85 | gaatag/ACGCAA | 3282 · 3366 | CTAAAC/gtaaga | 6 | 1 | 62 |
| 6 | 820 | atacag/CCCATC | 3429 · 4248 | TTCCAT/gtaagt | 7 | 2 | 67 |
| 7 | 371 | ttttag/CTCCGT | 4316 · 4686 | GCCAAG/gtaagt | 8 | 1 | 904 |
| 8a | 221 | ttctag/TCGCGA | 5591 · 5811 | TATATG/gtaatt | 9 | 0 | 336 |
| 8b | 221 | tcgaag/TTGTTA | 6148 · 6368 | TTTGCG/gtaatt | 10 | 0 | 385 |
| 8c | 221 | ttccag/TTACCT | 6754 · 6974 | TTTGCG/gtaaat | 11 | 0 | 525 |
| 8d | 221 | atgcag/TGCTAT | 7500 · 7720 | TTCGGG/gtaaag | 12 | 0 | 691 |
| 8e | 224 | tcccag/GTGTGC | 8412 · 8635 | TTTATG/gtattt | 13 | 0 | 4965 |
| 8f | 221 | agctag/GTCTTT | 13605 · 13825 | TTTCAG/gtaatc | 14 | 0 | 1141 |
| 8g | 221 | tcgcag/GTTTCA | 14967 · 15187 | TTCGAG/gtaatt | 15 | 0 | 340 |
| 9 | 218 | ggttag/GTTCTG | 15528 · 15745 | AGATCG/gtatgt | 16 | 2 | 64 |
| 10 | 507 | cttcag/CTTTAT | 15810 · 16316 | GTTCAG/gtaagc | 17 | 2 | 59 |
| 11 | 382 | atttag/AATAAT | 16376 · 16757 | ATTCAG/gtgggt | 18 | 0 | 4791 |
| 12 | 393 | ctatag/AAAACC | 21549 · 21941 | | | | |

(a) Capital letters are used for the sequence in the exon and small case letters for sequence in the intron.

(b) The numbering is based on nucleotide one being the A of the initiation codon.gMRP1b lacks two sites in comparison to them, and gMRP1a lacks three sites. But each of them also has one site at the 5' end of the sequence which is not present in gMRP1c and gMRP1d. Among all these sites, some are shared by either MRP1 or dMRP, but interestingly there is only one site (the first site in gMRP1b, which is not shared by other gMRPs), which is also common to dMRP and MRP1, while these two genes also have some common splice sites. It is noteworthy that conservation inside the anopheline species and between this one and the others involves in nearly all cases splice sites that are present in gMRP1c and gMRP1d. This indication is clearly in favor of these two forms being the most related to the common ancestor of gMRPs, with gMRP1a and gMRP1b having lost some splice sites after their divergence. Identity/similarity comparisons between MRP1 and gMRP deduced amino acid sequences also show that gMRP1a and gMRP1b are the most divergent (Table 3). gMRP1a is the gene that has the most different sequence and has lost the most splice sites in comparison to the others, an observation that suggests that it has diverged the first from the primitive sequence. The second gene to be duplicated must have been gMRP1b, but based on this data, it is not clear if it is gMRP1c or gMRP1d that gave birth to the others. These two genes have exactly the same splice sites, and their identity/similarity values with other MRPs are not significantly different, so that it cannot be determined which of these two sequences is closest to those of other species. Even if gMRP1a was the first duplicated copy in the anopheline, it is difficult to explain its high degree of divergence, that leads its deduced amino acid sequence to share no more identity with other gMRPs than with those of other species. One explanation could be that this duplicated copy was able to by-pass the selection pressure controlling the ancestral gene evolution by acquiring slightly new functions, thus allowing evolution on a new way. Characterization of the deduced amino acid sequences The predicted amino acid sequences of the four *A. gambiae* MRPs deduced from the sequencing studies are shown in FIG. 2, aligned with the *Drosophila* dMRP and human MRP1. For any of the *A. gambiae* are we sure of having entire cDNAs, so we do not know with certainty which is the initiation codon; however, based on comparison of the deduced amino acid sequences, we predict that the first methionine, for each gMRP, could be the one indicated in FIG. 2. In each case, the chosen methionine is preceded by STOP codons in all three ORFs, without other identical residue (data not shown). gMRP1c and gMRP1d also share an A nucleotide in position −3, in accordance with Kozak's observations on translation start sites (1996).

Alignment of these anopheline MRPs with those of other animal organisms clearly showed a difference between data obtained for gMRP1a and those of the three other gMRPs. gMRP1b, c, and d share more homogeneous sequences, while gMRP1a is strikingly different. Its identity and similarity values with other MRPs are low, even with the three other gMRPs (Table 3). The mean identity and similarity values between gMRP1a and the three other gMRPs are 30.1% and 48.8%, respectively, and they are of 29.5% and 46.5% with other MRPs. In contrast, gMRP1b–d are much more related to one another (82.1% mean identity, and 90.9% mean similarity) than to other MRPs (48.4% mean identity and 66.2% mean similarity). Among these, dMRP is the closest (53.2% mean identity and 71.1% similarity), while among the human MRPs, it is MRP1 (51.4% mean identity and 67.2% mean similarity). Identity between MRP1 and gMRP1b–d is even greater than between MRP1 and MRP4 or MRP5 in the human species (Borst et al., 2000). MRP3, the sequence of which is close to that of MRP1 (Borst et al., 1999) also shares great identity/similarity with the gMRP1b–d (47.9%/65.7% respective mean values). gMRP1c and gMRP1d are those which match the best with other sequences analysed here. It is then probable that one of these two sequences gave birth to the three others by gene duplication. Despite the great divergence of gMRP1a, the sequences of the gMRPs are more conserved between themselves than are those of the human MRPs integrated in this study (56.1% mean identity, and 69.8% mean similarity for the first ones versus 50.8% mean identity and 68.4% mean similarity for the second). The best matches between gMRPs and dMRP agrees with the logical hypothesis of a common ancestor gene for the two insects.

FIG. 2 highlights that the more conserved regions are the NBDs, the MSDs sharing less similarity. The less conserved regions are the first MSD and the linker region, as usual in ABC transporters (Hipfner et al., 1999). Walker A and B motifs, as well as the ABC signature are clearly identified on FIG. 2. gMRPs share the distinctive features of MRP1-like proteins, that are a structure with three MSDs in place of two for most of the ABC transporters, and the lack of 13 amino acids in the first NBD, in comparison to P-glycoprotein (Hipfner et al., 1999), which confirms their relatedness to MRP1 rather than to other structurally close proteins.

The deduced amino acid sequence of gMRP1c was compared to the sequences contained into the Sptrnrdb database using the BLASTP program, and the result showed best scores with SD07655 and CG6214 (1527 and 1507, respectively), which are sequences from the *D. melanogaster* MRP1 homologue (Grailles et al., submitted paper). The next best scores are those of the murine MRP (1338) and human MRP1 (1335). On the other hand, when the sequence was compared to the anopheline databases from TREMBL and SWISSPROT (http://konops.imbb.forth.gr/AnoDB), the highest scores observed were much lower than those cited above; they were not greater than 108 for SWISSPROT, and 67 for TREMBL. These results, in accordance with in situ hybridization, suggest that no other paralogues than those described here exist in the anopheline genome.

Comparison between the four cDNAs and the genomic sequence represented by BAC 22C14 allowed us to evaluate the length of each gene to slightly more than 5 kbp. gMRP1a–d respectively contain 2, 5, 7, and 7 exons. Contrary to the *Drosophila* gene dMRP, these ones do not possess exons represented as multiple interchangeable copies, and the introns are small (the biggest is only 603 bp), and these reasons explain the great difference observed between these genes length and that of the *Drosophila* or human homologues (22 kbp and 200 kbp, respectively).

Comparison of the Four Copy Structure and Expression

In human, the predicted structures of MRP proteins distinguishes two sub-groups: the first one contains MRP1, 2, 3, 6 and 7, which possess three MSDs, while the second group, containing MRP4 and MRP5, has a classical ABC-transporter structure with 2 MSDs (Hopper et al., 2001). The topological predictions we have realized for our gMRPs are in favor of three MSDs for these proteins, which means that they may belong to the first group. This is in accordance with their sequence similarity with the genes of this group, which is more important than with those of the second group (data not shown). The combination of secondary structure predictions and biochemical analyses have led to a topological model of MRP1 with 17 transmembrane domains, five in MSD1, and six in MSDs 2 and 3 (Kast & Gros, 1998). Also, the two NBDs have been clearly localized to the intracellular compartment by several methods (Flens et al., 1994; Bakos et al., 1996; Hiptner et al., 1996, 1997; Kast & Gros, 1998). Although we have no biochemical data on the gMRPs that could help in predicting their membrane topology, we assume, in regard to their relatedness with MRP1, that they should have a similar organization. This means that the $NH_2$ extremity of these proteins is more probably external, and the two NBDs are internal, as well as the COOH extremity. Respecting these features imposes some constraints on the organization of the transmembrane helices. It means that MSD1 must have an odd number of transmembrane domains, while MSD 2 and 3 each have an even number of these. We tried to integrate these data on the analysis of the secondary structure predictions obtained for our sequences, using the Tmap and PredictProtein softwares. Taking into account the results of these programs and known features on MRP1 structure, the first MSD of our gMRPs could contain five transmembrane helices, while MSD2 and MSD3 could each span the membrane six times. Such predictions are in accordance with the structure predicted for MRP1.

Figure 4:
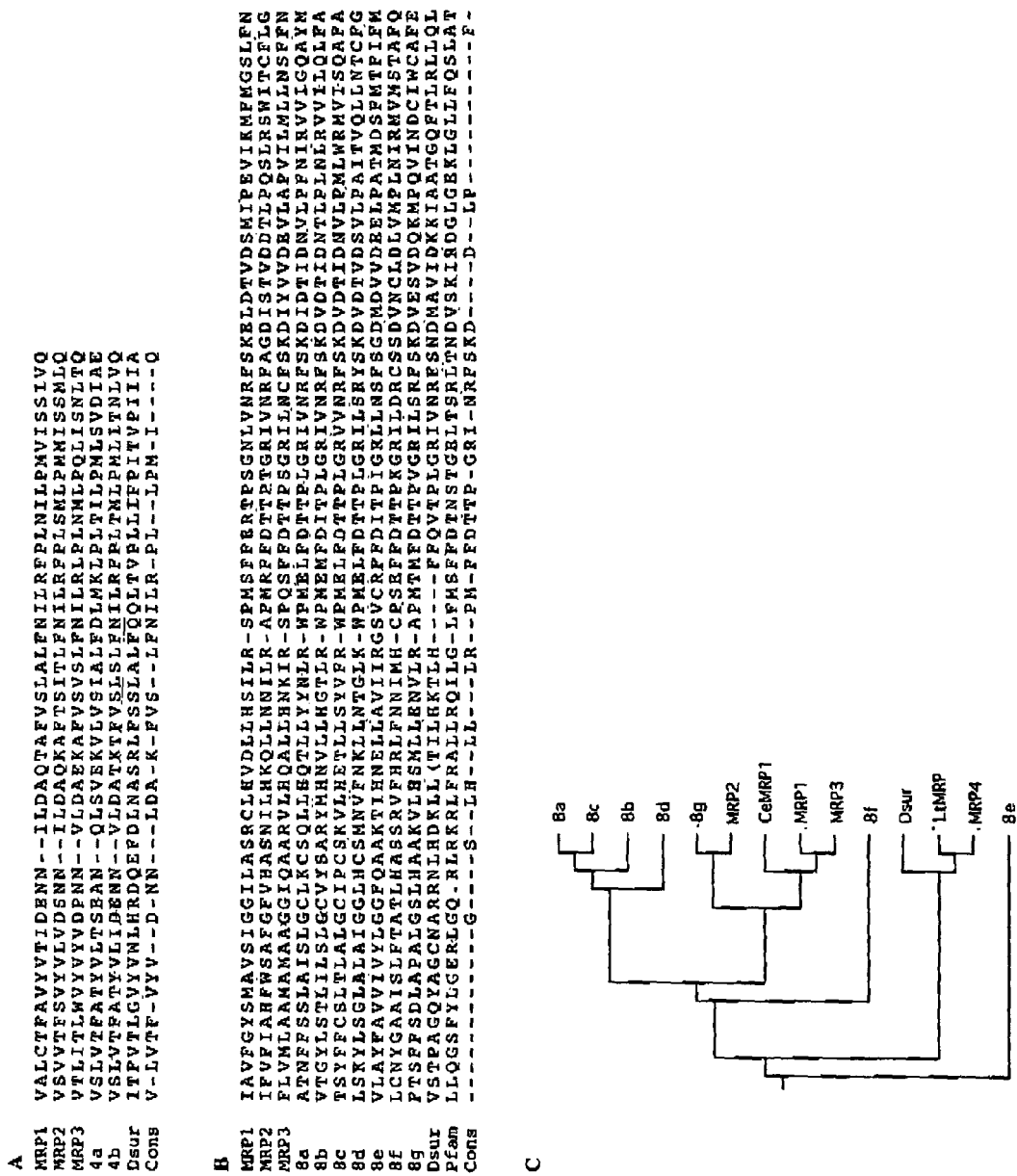
FIG. 4. Amino acid alignment of dMRP variable exon 4 (A) (SEQ ID NOS: 7 & 8) and 8 (B) (SEQ ID NOS: 9–15) encoded peptides with the cognate peptides from other organisms. The variant dMRP peptide sequence and the equivalent sequences from Drosophila sulfonylurea receptor (Dsur, NG_000795) (SEQ ID NOS: 71 & 75) and three human MRPs (MRP1, NM_004996 (SEQ ID NOS: 68 & 72); MRP2, NP_005836 (SEQ ID NOS: 69 & 73); and MRP3, Y17151 (SEQ ID NOS: 70 & 74)) were aligned using ClustalW. Pfam (SEQ ID NO: 76) refers to pfam00664, a consensus sequence for ABC transporter Membrane Spanning Domains. Gaps were introduced to maximize sequence identity and are shown by a horizontal dash. Residues that are identical in at least half of the sequences have their background shaded and those present in more than half of the sequences are listed in the consensus (Cons). (C) Dendrogram constructed with the data of part (B) of the Figure (see infra for details).
Figure 5:
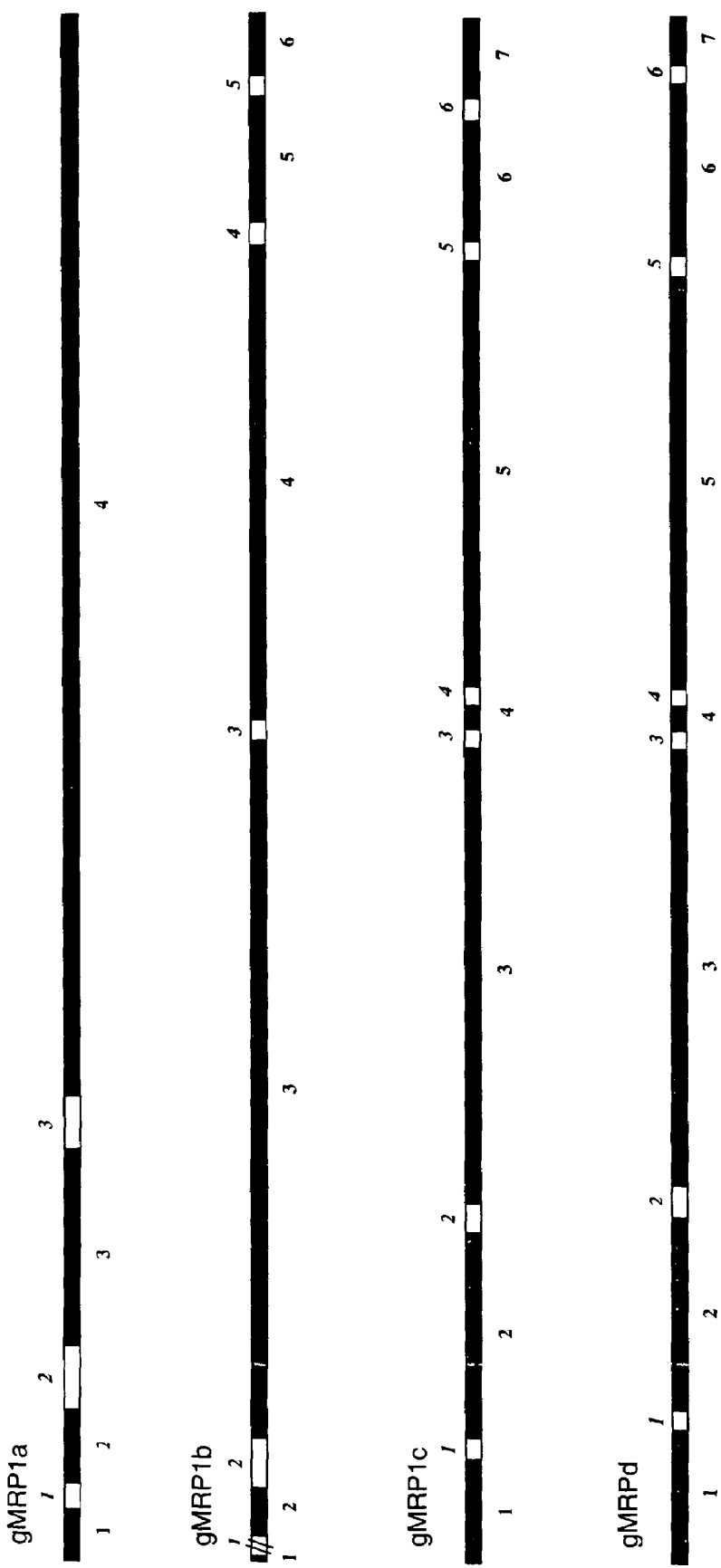
FIG. 5. Schematic representation of the four gMRP genes showing overall organization of exons and introns. Exons appear in black and are numbered under the sequence, while introns appear in white and are numbered in italic above the sequence.

In an attempt to see if each of these four genes could be related to a specific function, we compared their relative expressions between different tissues. This was performed by semi-quantitative RT-PCR, as described above. The tissues used were thorax, heads, Malpighi tubules, digestive tract, and salivary glands. After extraction of the RNAs from these tissues, reverse transcription (RT) was performed, followed by PCR with primers specific to genes gMRP1a–d. FIG. 4 shows that cDNAs corresponding to all four genes were present in these tissues. At least four experiments were conducted on each tissue. Comparison of the relative expression of the four gMRP genes in each tissue did not show differences of expression inside the salivary glands, the digestive tracts, and the thorax. However, in the Malpighi tubules we could note a stronger expression of gMRP1a, and a lesser expression of gMRP1b. At the head level, gMRP1b was always strongly expressed, while gMRP1c and gMRP1d exhibited a week expression. Our results are in favor of an ubiquitous localization of the four gMRPs, but the differences of expression observed could be related to functional specificities acquired by gene duplication evolution.

In summary, Drosophila melanogaster has a gene very similar to human MRP1 that encodes a full ABC-transporter containing three membrane-spanning domains (MSDs) and two nucleotide-binding domains (NBDs). This 19 exon insect gene, dMRP (FBgn0032456), spans slightly more than 22 kb. The cDNA SD07655 representing this gene was sequenced and found to contain sequences from 12 exons including single copies of two exons having multiple genomic copies. The gene contains two variant copies of exon 4 and seven of exon 8. While a cDNA contains only one version of each variable exon, all forms of these variable exons were detected in adult fly mRNA. These results predict that Drosophila could make 14 different MRP isoforms from a single gene by substituting different variable exons. This is the first report of any organism using differential splicing of alternative, internal exons, to produce such a large array of MRP isoforms having the same size, but with limited and defined internal variations. Defining the functional differences in the dMRP isoforms should provide clues to the structure/function relationships of the amino acids in these MRP domains, both for the insect enzyme and for those of other species.

The invention also constitutes the description of MRP homologues found in the Anopheles gambiae mosquito by computational analysis of genomic sequences. cDNAs corresponding to these genes were produced, and compared to the genomic sequences, in view of determining their structure. The particular interest of this study is the existence, in the anopheline genome, of a cluster of four genes of the same family, two of them having very close sequences. It does not seem that other copies of this gene family exist elsewhere in the genome, and the four described here, which have probably emerged by gene duplication, could be characterized by specific physiological roles, due to some differences observed in their tissue expression.

It is now clear, in regard of the increasing knowledge on human MRPs, and also on other animals, that this family of proteins is involved in a variety of biological processes, explaining the diversity of forms encountered in the organisms. In the only other insect studied for MRPs, Drosophila melanogaster, it seems that there is a unique gene, with internal variations at the exon level. In the case of the anopheline, no such variable exons have been detected, but genetic diversity was introduced by duplication. Particularly striking is the divergence observed in the gMRP1a paralogue in comparison to the three other genes. Even if it is not clear how to interpret this fact, it can be assumed than acquisition of a new function important for the mosquito could have explained a high rate of sequence divergence from the other paralogues during evolution.

RT-PCR experiments have demonstrated the transcription of each of the four forms in the adult mosquito, in the different tissues examined. Differences were noted in the level of expression of some forms on certain tissues, and also on a mosquito cell line, were it was clearly observed that gMRP1a and gMRP1b were far less expressed than the two others. These observations agree with the hypothesis that the different forms should have different physiological roles.

Logically, one can expect that the physiological function of these proteins will be similar to that of the human MRP1, because their structures are close. Even closer is the D. melanogaster dMRP, and data on that protein function will probably greatly help in the study of the anopheline forms, when they are available. It has been recently shown that dMRP could transport the well known substrate MRP1, leukotriene C4 (Roger Deeley, personal communication), which is the first functional demonstration of the relationship between the drosophila and human proteins. In D. melanogaster, the existence of variable exons has led us to suspect that these regions could play an important role in the structure and/or function of the protein (results under submission). The comparison of the sequences in this region, between the fly and human MRPs, showed that some amino acids were highly variable in some otherwise conserved regions. When we compare the alignment between gMRPs, MRP1 and dMRP in the same regions, this variability is confirmed. It seems to us that functional studies on these gene products should particularly focus on these amino acids, because they could lead to different substrate affinities. As the four forms of gMRPs were not equally expressed in all tissues one can speculate that their different specificities could involve them in different biological functions. Biochemical studies should help answer these questions in the future. The region corresponding to exon 4 of dMRP has not yet been studied functionally, but in the region corresponding to exon 8 one amino acid of the human MRP1 has been shown to be important in transport of anthracyclines, vincristine, and VP16 (Zhang et al., 2001). This residue is highly polymorphic in the gMRPs, as well as another residue, corresponding to $Thr^{1242}$ of MRP1, which is also important for the transport of several substrates in human. The variability at this level is probably related to functional specificity of the 4 gMRPs. Also, it is interesting to note that a near by amino acid, $Trp^{1246}$ of MRP1, which functional importance has been shown (Ito et al., 2001), and which is very conserved in the ABCC group (the MRPs group inside ABC transporters), is not conserved in any of the four gMRPs. Instead, gMRP1a has a Ser residue at this position, and the three others a Phe. This observation must be of physiological importance.

MRPs are transporters of organic anions, either conjugated or not to acidic ligands such as reduced glutathione (GSH), glucuronate or sulfate. Very little is currently known about the physiological function of MRPs, but the different members of the family in human have been characterized for different substrate specificities, which are most probably related to different physiological functions (Borst et al., 2000). Likewise, two homologue genes can have different substrate specificities from one species to another, which is illustrated for example by the human MRP1 and murine mrp (Stride et al., 1999). It is thus very probable that the variations observed in otherwise very conserved regions in the anopheline MRPs are related to such specificity. It is striking that, although three of the gMRPs have very similar sequences, and gene organization (especially gMRP1c and gMRP1d), the fourth, gMRP1a, is very different, in structure as well as in organization. It is too early to speculate about the implications of this observation, but is worth noting that this form exhibited different levels of expression according to the tissue or cultured cell line analysed. Probably, the different forms of anopheline MRPs act as members of a network of detoxifying proteins which clear the cell from the variety of products encountered in the environment.

One particular aspect of these protein function that has kept our attention is their strong affinity for glutathione conjugates, because it has been shown that glutathione S (GS)-transferases were involved in insecticide metabolism in the anopheline mosquito (Tang & Tu, 1994; Ranson et al., 1997; Hemingway & Ranson, 2000). It is so possible that the two proteins act together in a biological process that would couple conjugation of the toxic products to exportation of the newly formed complex. This hypothesis is supported by results on human cell lines that have shown a synergistic effect between GS-transferase and MRP1 overexpression to confer high-level resistance to several drugs (Morrow et al., 1998a; 1998b).

Gene duplication is one of the mechanisms contributing to evolution by conferring new properties to a protein, or even new function. This is more probably the case with the four gMRPs described here. Changes that have appeared in the gene sequence after the different duplications seemingly have provided functional specificity to each of the isoforms, which is relevant with the differences observed in expression at the tissue level. It now remains to be determined which are the substrates of each isoform, and how these contribute to the physiology of the mosquito; particularly interesting will be to investigate their potential role in insecticide resistance, knowing that insecticide control of vector is currently the most successful strategy against malaria (Collins et al., 2000). A better understanding of the mechanisms involved in insecticide resistance will help developing new control measures in the future.

REFERENCES

The following references are cited herein, and the disclosure of each reference is relied upon and incorporated by reference herein.

Altschul, S. F., Madden, T. L., Schaffer, A. A., Zhang, J., Zhang, Z., Miller, W., Lipman, D. J. 1997. Gapped BLAST and PSI-BLAST: a new generation of protein database search programs. Nucl. Acids Res. 25, 3389–3402.

Bateman, A., Birney, E., Cerruti, L., Durbin, R., Etwiller, L., Eddy, S. R., Griffiths-Jones, S., Howe, K. L., Marshall, M., Sonnhammer, E. L. 2002. The Pfam protein families database. Nucl. Acids Res. 30, 276–280.

Bera, T. K., Lee, S., Salvatore, G., Lee, B., Pastan, I. 2001. MRP8, a new member of ABC transporter superfamily, identified by EST database mining and gene prediction program, is highly expressed in breast cancer. Mol. Med. 7, 509–516.

Borst, P., Evers, R., Kool, M., Wijnholds, J. 2000. A family of drug transporters: the multidrug resistance-associated proteins. J. Natl. Cancer Inst. 92, 1295–1302.

Broeks, A., Gerrard, B., Allikmets, R., Dean, M., Plasterk, R. H. A 1996. Homologues of the human multidrug resistance genes MRP and MRP contribute to heavy metal resistance in the soil nematode *Caenorhabditis elegans*. Embo J. 15, 6132–6143.

Büchler, M., König, J., Brom, M., Kartenbeck, J., Spring, H., Horie, T., Keppler, D. 1996. cDNA cloning of the hepatocyte canalicular isoform of the multidrug resistance protein, cMrp, reveals a novel conjugate export pump deficient in hyperbilirubinemic mutant rats. J. Biol. Chem. 271, 15091–15098.

Cole, S. P. C., Bhardwaj, G., Gerlach, J. H., Mackie, J. E., Grant, C. E., Almquist, K. C., Stewart, A. J., Kurz, E. U., Duncan, A. M. V., Deeley R. G. 1992. Overexpression of a transporter gene in a multidrug-resistant human lung cancer cell line. Science 258, 1650–1654.

Dean, M., Rzhetsky, A., Allikmets, R. 2001. The human ATP-binding cassette (ABC) transporter superfamily. Genome Res. 11, 1156–1166.

Deeley, R. G., Cole, S. P. C. 1997. Function, evolution and structure of multidrug resistance protein (MRP). Semin. Cancer Biol. 8, 193–204.

Essodaïgui, M., Frézard, F., Moreira, E. S. A., Dagger, F., Garnier-Suillerot, A. 1999. Energy-dependent efflux from Leishmania promastigotes of substrates of the mammalian multidrug resistance pumps. Mol. Biochem. Parasitol. 100, 73–84.

Fromm, M. F., Leake, B., Roden, D. M., Wilkinson, G. R., Kim, R. B. 1999. Human MRP3 transporter: identification of the 5'-flanking region, genomic organization and alternative splice variants. Biochim. Biophys. Acta 1415, 369–374.

Grant, C. E., Kurz, E. U., Cole, S. P. C., Deeley, R. G. 1997. Analysis of the intron-exon organization of the human multidrug-resistance protein gene (MRP) and alternative splicing of its mRNA. Genomics 45, 368–378.

Hemingway, J., Ranson, H. 2000. Insecticide resistance in insect vectors of human disease. Annu. Rev. Entomol. 45, 371–391.

Higgins, D. G., Sharp, P. M. 1988. CLUSTAL: a package for performing multiple sequence alignment on a microcomputer. Gene 73, 237–244.

Hopper, E., Belinsky, M. G., Zeng, H., Tosolini, A., Testa, J. R., Kruh, G. D. 2001. Analysis of the structure and expression pattern of MRP7 (ABCC10), a new member of the MRP subfamily. Cancer Lett. 162, 181–191.

Juliano, R. L., Ling, V. 1976. A surface glycoprotein modulating drug permeability in Chinese hamster ovary cell mutants. Biochim. Biophys. Acta 455, 152–162.

Kool, M., de Haas, M., Scheffer, G. L., Scheper, R. J., van Eijk, M. J. T., Juijn, J. A., Baas, F., Borst P. 1997. Analysis of expression of cMOAT (MRP2), MRP3, MRP4, and MRP5, homologues of the multidrug resistance-associated protein gene (MRP1), in human cancer cell lines. Cancer Res. 57, 3537–3547.

Kozak M. 1996. Interpreting cDNA sequences: some insights from studies on translation. Mamm. Genome 7, 563–574.

Lu, Y. P., Li, Z. S., Rea, P. A. 1997. AtMRP1 gene of Arabidopsis encodes a glutathione S-conjugate pump: isolation and functional definition of a plant ATP-binding cassette transporter gene. Proc. Natl. Acad. Sci. U S A 94, 8243–8248.

Marck, C. 1988. 'DNA Strider': a 'C' program for the fast analysis of DNA and protein sequences on the Apple Macintosh family of computers. Nucl. Acids Res. 16, 1829-1836.

Morrow, C. S., Smitherman, P. K., Diah, S. K., Schneider, E., Townsend, A. J. 1998a. Coordinated action of glutathione S-transferases (GSTs) and multidrug resistance protein 1 (MRP1) in antineoplastic drug detoxification. J. Biol. Chem. 273, 20114–20120.

Morrow, C. S., Smitherman, P. K., Townsend, A. J. 1998b. Combined expression of multidrug resistance protein (MRP) and glutathione S-transferase P1-1 (GSTP1-1) in MCF7 cells and high level resistance to the cytotoxicities Ranson, H., Cornel, A. J., Fournier, D., Vaughan, A., Collins, F. H., Hemingway, J. 1997. Cloning and localization of a glutathione S-transferase class I gene from *Anopheles gambiae*. J. Biol. Chem. 272, 5464–5468.

Strimmer, K., von Haeseler, A. 1996. Quartet puzzling: A quartet maximum likelihood method for reconstructing tree topologies. Mol. Biol. Evol. 13, 964–969.

Suzuki, T., Sasaki, H., Kuh, H. J., Agui, M., Tatsumi, Y., Tanabe, S., Terada, M., Saijo, N., Nishio, K. 2000. Detailed structural analysis on both human MRP5 and mouse mrp5 transcripts. Gene 242, 167–173.

Szczypka, M. S., Wemmie, J. A., Moye-Rowley, W. S., Thiele, D. J. 1994. A yeast metal resistance protein similar to human cystic fibrosis transmembrane conductance regulator (CFTR) and multidrug resistance-associated protein. J. Biol. Chem. 269, 22853–22857.

Tang, A. H., Tu, C. P. 1994. Biochemical characterization of *Drosophila* glutathione S-transferases D1 and D21. J. Biol. Chem. 269, 27876–27884.

van Aubel, R. A., van Kuijck, M. A., Koenderink, J. B., Deen, P. M., van Os, C. H., Russel, F. G. M. 1998. Adenosine triphosphate-dependent transport of anionic conjugates by the rabbit multidrug resistance-associated protein Mrp2 expressed in insect cells. Mol. Pharmacol. 53, 1062–1067.

Bakos E., Hegedüs T., Holló Z., Welker E., Tusnády G. E., Zaman G. J. R., Flens M. J., Váradi A., and Balázs S. (1996). Membrane topology and glycosylation of the human multidrug resistance-associated protein. J. Biol. Chem. 271: 12322–12326.

Borst P., Evers R., Kool M., and Wijnholds J. (1999). The multidrug resistance protein family. Biochim. Biophys. Acta 1461: 347–357.

Collins F. H., Kamau L., Ranson H. A., and Vulule J. M. (2000). Molecular entomology and prospects for malaria control. Bull. World Health Organ. 78: 1412–1423.

Flens M. J., Izquierdo M. A., Scheffer G. L., Fritz J. M., Meijer C. J. L. M., Scheper R. J., and Zaman G. J. R. (1994). Immunochemical detection of the multidrug resistance-associated protein MRP in human multidrug-resistant tumor cells by monoclonal antibodies. Cancer Res. 54: 4557–4563.

Higgins, D. G., and Sharp, P. M. (1988). CLUSTAL: a package for performing multiple sequence alignment on a microcomputer. Gene 73: 237–244.

Hipfner D. R., Almquist K. C., Stride B. D., Deeley R. G., and Cole S. P. C. (1996). Location of a protease-hypersensitive region in the multidrug resistance protein (MRP) by mapping of the epitope of MRP-specific monoclonal antibody QCRL-1. Cancer Res. 56: 3307–3314.

Hipfner D. R., Almquist K. C., Leslie E. M., Gerlach J. H., Grant C. E., Deeley R., and Cole S. P. C. (1997). Membrane topology of the multidrug resistance protein (MRP). J. Biol. Chem. 272: 23623–23630.

Hipfner D. R., Deeley R. G., and Cole S. P. C. (1999). Structural, mechanistic and clinical aspects of MRP1. Biochim. Biophys. Acta 1461: 359–376.

Ito K. I., Olsen S. L., Qiu W., Deeley R. G., and Cole S. P. C. (2001). Mutation of a single conserved tryptophan in multidrug resistance protein 1 (MRP1/ABCC1) results in loss of drug resistance and selective loss of organic anion transport. J. Biol. Chem. 276: 15616–15624.

Kast C., and Gros P. (1998). Epitope insertion favors a six transmembrane domain model for the carboxy-terminal portion of the multidrug resistance-associated protein. Biochem. 37: 2305–2313.

Stride B. D., Cole S. P. C., and Deeley R. G. (1999). Localization of a substrate specificity domain in the multidrug resistance protein. J. Biol. Chem. 274: 22877–22883.

Zhang D. W., Cole S. P. C., and Deeley R. G. (2001). Identification of a nonconserved amino acid residue in multidrug resistance protein 1 important for determining substrate specificity. J. Biol. Chem. 276: 34966–34974.

---

What is claimed is:

1. A purified polynucleotide comprising a nucleotide sequence encoding SEQ ID NO: 1, or a fragment of SEQ ID NO: 1 comprising at least an ATP binding domain.

2. A purified polynucleotide that hybridizes to either strand of a denatured, double-stranded DNA encodinci SEQ ID NO: 1 under conditions of high stringency, wherein said conditions comprise hybridization at 65° C. in 1% BSA, 0.25 M $NaH_2PO_4$ pH 7.2, 1 mM EDTA, and 150 µg/ml salmon sperm DNA, and further comprise washing at 65° C. in 40 mM $NaH_2PO_4$, pH 7.2, 1% SDS, and 1 mM EDTA.

3. The polynucleotide of claim 1 or claim 2 which is labeled with a detectable moiety.

4. An expression vector comprising the polynucleotide of claim 1 or claim 2.

5. A vector comprising the nucleotide of claim 1 or claim 2.

6. An isolated host cell containing the vector of claim 5.

7. A method for expressing SEQ ID NO: 1 in a transformed host cell, said method comprising culturing said transformed host cell of claim 6 under conditions suitable for gene expression.

8. A method for constructing a transformed host cell capable of expressing SEQ ID NO: 1, said method comprising transforming a host cell with a recombinant DNA vector that comprises the polynucleotide of claim 1.

* * * * *

UNITED STATES PATENT AND TRADEMARK OFFICE
CERTIFICATE OF CORRECTION

| | | |
|---|---|---|
| PATENT NO. | : 7,067,259 B2 | Page 1 of 1 |
| APPLICATION NO. | : 10/667891 | |
| DATED | : June 27, 2006 | |
| INVENTOR(S) | : Charles W. Roth et al. | |

It is certified that error appears in the above-identified patent and that said Letters Patent is hereby corrected as shown below:

column 95, line 6, "encodinci" should read --encoding--.

Signed and Sealed this

Fifth Day of September, 2006

JON W. DUDAS
*Director of the United States Patent and Trademark Office*

SEQUENCE LISTING

```
<160> NUMBER OF SEQ ID NOS: 76

<210> SEQ ID NO 1
<211> LENGTH: 1548
<212> TYPE: PRT
<213> ORGANISM: Drosophila melanogaster

<400> SEQUENCE: 1

Met Ala Asp Asp Thr Ser Ser Pro Met Asp Arg Phe Cys Gly Ser Thr
 1               5                  10                  15

Phe Trp Asn Ala Thr Glu Thr Trp Tyr Thr Asn Asp Pro Asp Phe Thr
            20                  25                  30

Pro Cys Phe Glu Gln Thr Ala Leu Val Trp Thr Pro Cys Ala Phe Tyr
        35                  40                  45

Trp Ala Phe Val Ile Phe Asp Phe Tyr Tyr Leu Lys Ala Ser Leu Asp
    50                  55                  60

Arg Asn Ile Pro Trp Asn Lys Leu Asn Val Ser Lys Ala Leu Val Asn
65                  70                  75                  80

Leu Gly Leu Leu Val Ile Thr Ala Leu Asp Leu Ile Met Ala Leu Val
```

-continued

```
                    85                  90                  95
Lys Lys Gly Gly Asp Ser Glu Leu Pro Leu Tyr Asp Leu Asp Val Trp
                100                 105                 110
Gly Pro Ile Ile Lys Phe Ala Thr Phe Leu Leu Leu Phe Ile Phe Ile
            115                 120                 125
Pro Leu Asn Arg Lys Tyr Gly Val Gln Thr Thr Gly Cys Gln Phe Ile
        130                 135                 140
Phe Trp Phe Leu Leu Thr Val Leu Ser Ile Pro Arg Cys Arg Thr Glu
145                 150                 155                 160
Val Arg Leu Asp Ala Glu Arg Gln Lys Ile Leu Asn Ser Gln Gln Pro
                165                 170                 175
Ser Glu Gln Asp Phe Ser Trp Glu Glu Tyr Gln Phe Val Ser Phe Phe
                180                 185                 190
Ile Phe Phe Thr Phe Thr Ser Ile Met Leu Ile Leu Asn Cys Phe Ala
            195                 200                 205
Asp Gly Met Pro Arg Gln Thr Lys Tyr Gln Arg Gly Glu Asn Glu Ile
        210                 215                 220
Pro Glu Leu Ser Ala Ser Phe Leu Ser Arg Ile Thr Tyr Gln Trp Phe
225                 230                 235                 240
Asp Lys Met Ala Leu Lys Gly Tyr Arg Asn Pro Leu Glu Glu Lys Asp
                245                 250                 255
Leu Trp Asp Leu Arg Pro Gln Asp Ser Cys Ser Glu Val Met Pro Ile
                260                 265                 270
Phe Ala His His Trp Asn Gln Asn Val Arg Lys Asn Tyr Lys Asn Lys
            275                 280                 285
Ala Arg Val Glu Pro Lys Ala Gln Phe Ser Asn Gly Asn Val Thr Phe
        290                 295                 300
Glu Asn Pro His Gly Glu Lys Asn Gly Arg Lys Lys Gly Met Ala Ser
305                 310                 315                 320
Ile Met Pro Pro Ile Tyr Lys Ser Phe Gly Val Phe Leu Phe Gly
                325                 330                 335
Ala Leu Met Lys Leu Phe Thr Asp Thr Leu Thr Phe Ala Gln Pro Gln
            340                 345                 350
Val Leu Ser Leu Ile Ile Ser Phe Val Glu Ala Gln Asp Ala Glu Pro
        355                 360                 365
Glu Trp Lys Gly Ile Leu Tyr Ala Val Leu Leu Phe Val Leu Ala Ala
370                 375                 380
Ala Gln Thr Phe Ile Leu Gly Gln Tyr Phe His Arg Met Phe Ile Val
385                 390                 395                 400
Gly Leu Arg Ile Arg Thr Ala Leu Ile Asn Ala Ile Tyr Arg Lys Ala
                405                 410                 415
Leu Arg Ile Ser Asn Ser Thr Lys Lys Glu Ser Thr Val Gly Glu Ile
            420                 425                 430
Val Asn Leu Met Ala Val Asp Ala Gln Arg Phe Met Glu Leu Thr Thr
        435                 440                 445
Tyr Leu Asn Met Ile Trp Ser Ala Pro Leu Gln Ile Gly Leu Ala Leu
    450                 455                 460
Tyr Phe Leu Trp Gln Gln Leu Gly Pro Ser Val Leu Ala Gly Leu Ala
465                 470                 475                 480
Val Met Ile Ile Leu Ile Pro Val Asn Gly Val Ile Ala Ser Arg Ile
                485                 490                 495
Lys Thr Tyr Gln Ile Arg Gln Met Lys Tyr Lys Asp Glu Arg Val Lys
            500                 505                 510
```

```
Leu Met Asn Glu Val Leu Ser Gly Ile Lys Val Leu Lys Leu Tyr Ala
        515                 520                 525
Trp Glu Pro Ser Phe Glu Lys Gln Val Leu Asp Ile Arg Asp Lys Glu
530                 535                 540
Ile Ala Thr Leu Arg Ser Thr Ala Tyr Leu Asn Ala Gly Thr Ser Phe
545                 550                 555                 560
Leu Trp Ser Cys Ala Pro Phe Leu Val Ser Leu Val Thr Phe Ala Thr
                565                 570                 575
Tyr Val Leu Ile Asp Glu Asn Asn Val Leu Asp Ala Thr Lys Thr Phe
                580                 585                 590
Val Ser Leu Ser Leu Phe Asn Ile Leu Arg Phe Pro Leu Thr Met Leu
        595                 600                 605
Pro Met Leu Ile Thr Asn Leu Val Gln Thr Gln Val Ser Val Asn Arg
        610                 615                 620
Ile Asn Lys Phe Leu Asn Ser Glu Glu Leu Asp Pro Asn Ser Val Leu
625                 630                 635                 640
His Asp Ser Ser Lys Pro His Pro Met Ser Ile Glu Asn Gly Glu Phe
                645                 650                 655
Ser Trp Gly Asp Glu Ile Thr Leu Arg Asn Ile Asn Ile Glu Val Lys
                660                 665                 670
Lys Gly Ser Leu Val Ala Leu Val Gly Thr Val Gly Ser Gly Lys Ser
        675                 680                 685
Ser Val Val Gln Ala Phe Leu Gly Glu Met Glu Lys Leu Ala Gly Val
        690                 695                 700
Val Asn Thr Val Gly Lys Leu Ala Tyr Val Pro Gln Gln Ala Trp Ile
705                 710                 715                 720
Gln Asn Ala Thr Val Arg Asp Asn Ile Leu Phe Gly Gln Thr Tyr Asp
                725                 730                 735
Arg Lys Arg Tyr Asn Lys Val Ile Asp Ala Cys Ala Leu Arg Ala Asp
                740                 745                 750
Ile Asp Ile Leu Ser Ala Gly Asp Leu Thr Glu Ile Gly Glu Lys Gly
        755                 760                 765
Ile Asn Leu Ser Gly Gly Gln Lys Gln Arg Ile Ser Leu Ala Arg Ala
        770                 775                 780
Val Tyr Ser Asp Ala Asp Leu Tyr Leu Leu Asp Asp Pro Leu Ser Ala
785                 790                 795                 800
Val Asp Ala His Val Gly Lys His Ile Phe Glu Glu Val Ile Gly Pro
                805                 810                 815
Lys Gly Ile Leu Ala Arg Lys Ser Arg Val Leu Val Thr His Gly Val
                820                 825                 830
Thr Phe Leu Pro Gln Val Asp Ser Ile Tyr Val Ile Lys Met Gly Glu
        835                 840                 845
Ile Ser Glu Ser Gly Thr Phe Asp Gln Leu Val Lys Asn Lys Gly Ala
        850                 855                 860
Phe Ala Asp Phe Ile Ile Gln His Leu Gln Glu Gly Asn Glu Glu Glu
865                 870                 875                 880
Glu Glu Leu Asn Gln Ile Lys Arg Gln Ile Ser Ser Thr Ala Asp Val
                885                 890                 895
Pro Glu Leu Leu Gly Thr Val Glu Lys Ala Ile Lys Leu Ala Arg Thr
                900                 905                 910
Glu Ser Leu Ser Asp Ser Ile Ser Val Thr Ser Ala Asp Ser Leu Met
        915                 920                 925
```

```
Gly Gly Gly Gly Ser Leu Arg Arg Thr Lys Arg Gln Asp Ser His
        930                 935                 940

Asp Ser Val Ala Ser Ala Ala Ser Leu Lys Lys Lys Gln Glu Val Glu
945                 950                 955                 960

Gly Lys Leu Ile Glu Thr Glu Lys Ser Gln Thr Gly Gly Val Glu Phe
                965                 970                 975

Ala Val Tyr Lys His Tyr Ile Lys Ser Val Gly Ile Phe Leu Ser Val
            980                 985                 990

Ala Thr Leu Val Leu Asn Phe Val Phe Gln Ala Phe Gln Ile Gly Ser
        995                 1000                1005

Asn Leu Trp Leu Thr Gln Trp Ala Asn Asp Gln Asn Val Ala Asn Asp
1010                1015                1020

Thr Gly Leu Arg Asp Met Tyr Leu Gly Val Tyr Gly Ala Phe Gly Phe
1025                1030                1035                1040

Gly Gln Val Leu Ser Lys Tyr Leu Ser Gly Leu Ala Leu Ala Ile Gly
                1045                1050                1055

Gly Leu His Cys Ser Met Asn Val Phe Asn Lys Leu Leu Asn Thr Gly
                1060                1065                1070

Leu Lys Trp Pro Met Glu Leu Phe Asp Thr Thr Pro Leu Gly Arg Ile
            1075                1080                1085

Leu Ser Arg Tyr Ser Lys Asp Val Asp Thr Val Asp Ser Val Leu Pro
1090                1095                1100

Ala Ile Thr Val Gln Leu Leu Asn Thr Cys Phe Gly Val Leu Ala Thr
1105                1110                1115                1120

Ile Val Val Ile Ser Leu Ser Thr Pro Ile Phe Leu Ala Val Ile Val
                1125                1130                1135

Pro Ile Ala Phe Leu Tyr Tyr Phe Ala Gln Arg Phe Tyr Val Ala Thr
            1140                1145                1150

Ser Arg Gln Leu Met Arg Leu Glu Ser Val Ser Arg Ser Pro Ile Tyr
        1155                1160                1165

Ser His Phe Ser Glu Thr Val Thr Gly Ala Ser Thr Ile Arg Ala Tyr
    1170                1175                1180

Asn Val Gly Asp Arg Phe Ile Glu Glu Ser Asp Ala Lys Val Asp Lys
1185                1190                1195                1200

Asn Gln Val Cys Lys Tyr Pro Ser Val Ile Ala Asn Arg Trp Leu Ala
                1205                1210                1215

Ile Arg Leu Glu Met Val Gly Asn Leu Ile Ile Leu Phe Ala Ser Leu
            1220                1225                1230

Phe Ala Val Leu Gly Gly Gln Thr Asn Pro Gly Leu Val Gly Leu Ser
        1235                1240                1245

Val Ser Tyr Ala Leu Gln Val Thr Gln Thr Leu Asn Trp Leu Val Arg
    1250                1255                1260

Met Ser Ser Asp Ile Glu Thr Asn Ile Val Ser Val Glu Arg Ile Lys
1265                1270                1275                1280

Glu Tyr Gly Glu Thr Lys Gln Glu Ala Pro Trp Glu Leu Glu Gln Asp
                1285                1290                1295

Lys Asn Lys Pro Lys Asn Trp Pro Gln Glu Gly Arg Val Glu Phe Gln
            1300                1305                1310

Asn Phe Gln Val Arg Tyr Arg Glu Gly Leu Asp Leu Val Leu Arg Gly
        1315                1320                1325

Val Ser Phe Asn Ile Gln Gly Gly Glu Lys Val Gly Ile Val Gly Arg
    1330                1335                1340

Thr Gly Ala Gly Lys Ser Ser Leu Thr Leu Ala Leu Phe Arg Ile Ile
```

-continued

```
                1345                1350                1355                1360
Glu Ala Gly Gly Arg Ile Ser Ile Asp Gly Val Asp Ile Ala Ser
            1365                1370                1375
Met Gly Leu His Met Leu Arg Ser Arg Leu Thr Ile Ile Pro Gln Asp
        1380                1385                1390
Pro Val Leu Phe Ser Gly Ser Leu Arg Ile Asn Leu Asp Pro Phe Glu
        1395                1400                1405
Ile Lys Thr Asp Asp Glu Ile Trp Lys Ala Leu Glu Leu Ser His Leu
    1410                1415                1420
Lys Ser Phe Val Lys Ser Leu Ala Ala Gly Leu Asn His Glu Ile Ala
1425                1430                1435                1440
Glu Gly Gly Glu Asn Leu Ser Val Gly Gln Arg Gln Leu Val Cys Leu
            1445                1450                1455
Ala Arg Ala Leu Leu Arg Lys Thr Lys Val Leu Val Leu Asp Glu Ala
        1460                1465                1470
Thr Ala Ala Val Asp Leu Glu Thr Asp Asp Leu Ile Gln Lys Thr Ile
    1475                1480                1485
Arg Thr Glu Phe Lys Glu Cys Thr Val Leu Thr Ile Ala His Arg Leu
    1490                1495                1500
Asn Thr Ile Leu Asp Ser Asp Lys Val Ile Val Leu Asp Lys Gly Gln
1505                1510                1515                1520
Ile Ile Glu Phe Ala Ser Pro Thr Glu Leu Leu Asp Asn Pro Lys Ser
            1525                1530                1535
Ala Phe Tyr Ser Met Ala Lys Asp Ala Asn Leu Val
        1540                1545

<210> SEQ ID NO 2
<211> LENGTH: 1414
<212> TYPE: PRT
<213> ORGANISM: Anopheles gambiae

<400> SEQUENCE: 2

Met Val Glu Pro Val Ser Leu Pro Leu Val Asp His Leu Val Val Tyr
 1               5                  10                  15
Gly Phe Gln Tyr Leu Leu Val Cys Leu Phe Phe Leu Ser Glu Leu Ser
             20                  25                  30
Tyr Val Lys Gln Asp Val Pro Val Gln Thr Ser Arg Arg Thr Val His
         35                  40                  45
Ser Ile Phe Ser Ala Phe Leu Val Leu Val Thr Leu Ala Gly Val Val
     50                  55                  60
Val Ala Ala Phe Arg Leu Val Asp Asp Ser Val Ala Val Trp Arg Asp
 65                  70                  75                  80
Gly Ile Glu Ala Ile Ser Leu Val Gly Ile Leu Phe Leu Gln Ile Tyr
                 85                  90                  95
Ser Ile Arg Arg Asn Val Asp His Ile Tyr Leu Phe Thr Phe Trp Thr
            100                 105                 110
Leu Arg Thr Leu Ala Leu Ser Met Asp Val Ala Phe Asp Arg Thr Glu
        115                 120                 125
Trp Tyr Asp Phe Met His Leu Met Leu Ala Phe Ala Trp Leu Cys Ala
    130                 135                 140
Cys Gly Ile Arg Ser Tyr Ser Gly Gly His Asp Ser Ser Thr Gly
145                 150                 155                 160
Ser Asn Thr Pro Arg Lys Pro Asn Phe Ile Arg Gly Leu Phe Phe Ser
                165                 170                 175
```

```
Trp Met Asp Ser Thr Tyr Arg Glu Ala His Arg Gly Ser Val Ala Phe
        180                 185                 190

Tyr Gln Gly Thr Leu Phe Gln Gly Thr Leu Pro Glu Asp Arg Arg Cys
        195                 200                 205

Glu Gln Leu Leu Glu Leu Tyr Glu Lys Ala Asn Ala Arg Arg Gly Tyr
        210                 215                 220

Thr Ala Val Asp Asp Gly Ser Gly Arg Met Glu Ser Glu Leu Cys Arg
225                 230                 235                 240

Phe Thr Ile Gly Lys Leu Leu Ser Pro Phe Arg Gly Glu Ile Ile Leu
                245                 250                 255

Ala Gly Leu Asn Arg Phe Val Leu Ile Ser Leu Phe Phe Leu Cys Pro
                260                 265                 270

Tyr Leu Leu Arg Leu Leu Leu Glu Glu Asn Gln Pro Arg Met Tyr Gln
            275                 280                 285

Lys Trp Ile Val Thr Ala Leu Phe Asp Ala Ser Thr Ile Ile Ala Ile
        290                 295                 300

Leu Asn Thr His Tyr Gln His Thr Gln Asp Ile Gly Leu Arg Ile
305                 310                 315             320

Arg Ser Ile Leu Met Gly Ala Ile Tyr Arg Ser Ile Leu His Asp Gly
                325                 330                 335

Ile Thr Ser Asn Ala Ser Ser Asp Thr Leu Thr Ser Asp Thr Ala Leu
                340                 345                 350

Phe Val Pro Phe Ile Gln Asn Leu His Met Met Trp Ser Ala Pro Leu
                355                 360                 365

Ile Ile Leu Ile Thr Phe Val Ala Leu Trp Val Gly Val Leu Gly Pro
        370                 375                 380

Ile Gly Thr Val Gly Leu Ala Ile Ile Val Ala Val Ile Ala Ile Thr
385                 390                 395                 400

Arg Lys Leu Ala Lys Lys Ile Ala Ala Gln Glu Lys His Ile Thr Ala
                405                 410                 415

His Ser Asn Asp Arg Val Arg Leu Thr Thr Ala Ser Ile Glu Gln Met
                420                 425                 430

Gln Gln Ile Lys Ser Asp Leu Met Glu Pro Phe Phe Glu Gln Arg Ile
            435                 440                 445

Gly Glu His Arg Arg Ala Glu Leu Ser His Met Cys Thr Tyr Ile Leu
        450                 455                 460

Tyr Asp Ala Leu Lys Tyr Leu Leu Ser Ile Ala Thr Pro Met Ile Val
465                 470                 475                 480

Ala Cys Gly Thr Phe Leu Phe Met Tyr Val Val Gly Ser Gly Ala Leu
                485                 490                 495

Leu Thr Val Gln Ser Met Phe Val Ala Ile Ala Leu Phe Gly Leu Thr
            500                 505                 510

Arg Tyr Pro Leu Ser Glu Leu Pro Asn Leu Met Ala Asn Trp Gly Thr
        515                 520                 525

Ile Asn Val Lys Leu Gln Val Ile Asn Glu Val Val Cys Ser Gly Lys
        530                 535                 540

Gln Arg Lys Ser Ser Gly Lys Met Pro Gln Asn Gly Ser Ser Thr Gly
545                 550                 555                 560

Gly Ala Gly Arg Gly Ser Phe Glu Lys Met Gln Glu Val Val His Thr
                565                 570                 575

Phe Val Asp Gln Leu Glu Asp Ser Ile Ala Asp Thr Ser Arg Ala Glu
                580                 585                 590

Val Leu Arg Ile Glu Arg Ala Lys Phe Ser Thr Glu Lys Asn Thr Ile
```

```
                    595                 600                 605
Leu Arg Gly Ile Asn Leu Thr Leu Arg Glu Gly Thr Phe Ile Gly Val
    610                 615                 620
Ser Gly Thr His Gly Ser Gly Lys Thr Ser Leu Leu Arg Ala Met Ile
625                 630                 635                 640
Gly Arg Leu Gln Arg Thr Gly Gly Thr Ser Thr Ile Ala Trp Asn Arg
                645                 650                 655
Val Ala Tyr Cys Pro Gln Thr Pro Trp Ile His Ser Gly Thr Ile Arg
                660                 665                 670
Ser Asn Ile Leu Phe Gly Gln Glu Tyr Glu Lys Ser Arg Tyr Glu Glu
                675                 680                 685
Val Leu Arg Ala Cys Cys Leu Glu Glu Asp Leu Lys Thr Phe Pro Asp
    690                 695                 700
Tyr Asp Glu Arg Val Val Ser Glu Gly Gly His Ser Leu Ser Gly Gly
705                 710                 715                 720
Gln Ala Arg Arg Val Ser Leu Ala Arg Ala Val Tyr Arg His Ala Asp
                725                 730                 735
Val Tyr Leu Leu Asp Asp Pro Leu Arg Ser Leu Asp Pro Asn Val Ala
            740                 745                 750
Arg Lys Val Phe Glu Gly Val Phe His Arg Gln His Gly Leu Leu Ala
            755                 760                 765
Gly Cys Thr Cys Val Phe Ile Ser His Asp Pro Glu His Leu Ser Ile
770                 775                 780
Ala Asp Lys Val Leu Val Met Ala Gly Gly Thr Ile Glu Lys Val Leu
785                 790                 795                 800
Lys Pro Ala Glu Val Ser Val Glu Leu Leu Gly Gln Leu Asn Gly Ala
                805                 810                 815
Glu Asp Glu Pro Glu Gln Glu Glu Lys Ala Pro Lys Ala Asp Gln Gln
            820                 825                 830
Asn Lys Lys Arg Ala Arg Lys Ala Gln Pro Lys Gly Thr Asp His Gly
            835                 840                 845
Glu Gly Asn Val Ser Leu Gly Leu Tyr Val Thr Phe Ala Arg Met Leu
850                 855                 860
Lys Arg Arg Tyr Cys Val Gly Ala Leu Cys Phe Glu Ser Thr Val Thr
865                 870                 875                 880
Ala Leu Asp Ile Val Ile Thr Leu Leu Ala Gln Trp Ala Ala Ser
                885                 890                 895
Asp Lys Gln Thr Ser Gly Ala Leu Leu His Thr Thr Trp Ile Leu Cys
            900                 905                 910
Val Trp Val Leu Leu Ile Phe Leu Lys Thr Ala Ile Ile His Trp Ala
            915                 920                 925
Gly Leu Ser Leu Ser Lys Arg Val His Ser Gln Met Leu Ala Thr Ile
    930                 935                 940
Leu Arg Gln Pro Met Glu Phe Phe Asp Leu Asn Asp Ser Gly Val Ile
945                 950                 955                 960
Val Asn Arg Phe Ser Asn Asp Leu Lys Val Val Asp Lys Thr Ile Ile
                965                 970                 975
Thr Ser Val Arg Ser Val Leu Ser Ala Ser Phe Ser Val Leu Gly Thr
            980                 985                 990
Leu Met Leu Phe Val Tyr Lys Leu His Ser Lys Leu Leu Phe Val
        995                 1000                1005
Leu Ala Phe Thr Ala Ala Leu Met Leu Val Cys Gly Leu Lys Arg Leu
    1010                1015                1020
```

Leu Ser Tyr His Leu Gln Val Ala Arg Thr Leu Lys Arg Phe Glu Ala
1025                1030                1035                1040

Ser Ser Arg Ser Pro Ile Ile Leu Gln Tyr Asn Glu Thr Ile Gln Gly
            1045                1050                1055

Ile Asp Thr Ile Lys Ala Tyr Glu Ala Glu Asp Arg Leu Leu Arg Gln
        1060                1065                1070

Phe Phe Glu Arg Val Asp Thr His Gln Asn Tyr Ile Tyr His Asn Arg
    1075                1080                1085

Phe Ala Asn Arg Trp Ile Gly Ile Arg Leu Glu Phe Ile Gly Ala Ile
1090                1095                1100

Val Ile Tyr Tyr Val Ala Leu Leu Thr Val Ser Asn Gln Ser Met Val
1105                1110                1115                1120

Gly Phe Ala Phe Val Gly Ile Ile Val Ser Tyr Val Leu Arg Leu Ile
            1125                1130                1135

Pro Ser Leu Asn Ser Leu Leu Ala Leu Gly Ala Leu Glu Glu Asn
        1140                1145                1150

Ile Ile Ser Phe Glu Arg Val Ala Gln Tyr Leu Asp Leu Gln Arg Glu
    1155                1160                1165

Thr Asn Asp Asp Thr Gly Val Asp Tyr Pro Thr Ser Gly Met Asp Lys
1170                1175                1180

His Pro Val Leu Gly Pro Ile Ile Tyr Arg Asp Phe Ser Leu Thr His
1185                1190                1195                1200

Ala Asp Gly Ser Thr Val Leu His Asn Val Thr Leu Thr Ile Ala Ala
            1205                1210                1215

Gly Glu Lys Leu Gly Ile Val Gly Arg Thr Gly Ser Gly Lys Ser Ser
        1220                1225                1230

Phe Ile Gly Thr Leu Phe Arg Phe Tyr Pro Lys His Thr Thr Gly Tyr
    1235                1240                1245

Ile Ser Ile Ala His Val Glu Leu Gly Arg Ile Ser Leu Gln Lys Leu
1250                1255                1260

Arg Gly Glu Leu Thr Leu Val Pro Gln Ser Thr Ser Leu Phe Ser Gly
1265                1270                1275                1280

Val Val Gln Asn Phe Ile Asp Pro Arg Asn Gly His Thr Asp Glu Glu
            1285                1290                1295

Leu Ile Arg Cys Leu Arg Glu Cys Gly Leu Gly Asn Val His Leu Ala
        1300                1305                1310

Thr Pro Leu Glu Asn Leu Ser Val Gly Gln Cys Gln Leu Leu Cys Leu
    1315                1320                1325

Val Arg Gly Phe Leu Arg Lys Lys Pro Ile Ile Ile Leu Asp Glu Ala
1330                1335                1340

Thr Ser Ala Leu Asp Glu Ala Thr Glu Asp Leu Ile Leu Lys Val Leu
1345                1350                1355                1360

Asp Lys Gln Phe His Gly Arg Thr Val Leu Met Ile Ala His His Leu
        1365                1370                1375

Asn Thr Leu Arg Asn Cys His Arg Val Leu Trp Leu Gln Glu Gly Arg
    1380                1385                1390

Val Arg Lys Ile Ala Pro Leu Gln Asp Tyr Thr Val Glu Glu Arg Ala
1395                1400                1405

Glu Leu Gly Phe Arg Asp
    1410

<210> SEQ ID NO 3
<211> LENGTH: 1499

-continued

```
<212> TYPE: PRT
<213> ORGANISM: Anopheles gambiae

<400> SEQUENCE: 3

Met Thr Phe Glu Glu Phe Cys Gly Gly Pro Phe Trp Asp Asp Leu
 1               5                  10                  15

Thr Trp Arg Glu Glu Asp Pro Asp Leu Thr Phe Cys Phe Gln Arg Val
            20                  25                  30

Ile Leu Gln Trp Thr Pro Cys Phe Leu Phe Val Phe Ser Met Tyr
        35                  40                  45

Glu Val Leu Arg Ile Val Thr Ser Arg Tyr Arg Asp Ile Pro Trp Asn
50                  55                  60

Trp Phe Asn Ile Thr Lys Met Ile Phe Thr Phe Ala Leu Met Val Met
65                  70                  75                  80

Ser Trp Val Asp Leu Gly Val Gly Leu Ala Asn Asp Trp Ile Glu Ser
                85                  90                  95

Leu Leu Ser Met Leu Pro Ser Leu Pro Phe Gln Ile Met Ala Met Ala
                100                 105                 110

Leu Tyr Phe Phe Tyr Arg Lys Tyr Gly Ile Arg Ser Thr Gly Thr Met
            115                 120                 125

Phe Ile Phe Trp Phe Leu Lys Ala Phe Phe Gly Ile Ile Gln Met Arg
130                 135                 140

Thr Glu Ala Met Leu His Asp Val Arg Gly Ser Gly Thr Gly Asp Phe
145                 150                 155                 160

Ala Glu Phe Gln Phe Val Ser Tyr Thr Ile Gln Tyr Thr Phe Val Cys
                165                 170                 175

Cys Val Leu Leu Leu Glu Leu Phe Pro Asp Lys Glu Pro Arg Tyr Ser
            180                 185                 190

Glu Trp Ala Lys Leu Lys Asn Pro Asn Pro Glu Leu Arg Ser Ser Phe
        195                 200                 205

Phe Ser Arg Leu Phe Tyr Leu Tyr Phe Asp Ser Tyr Ala Trp Arg Gly
210                 215                 220

Phe Arg Lys Pro Leu Thr Asp Asp Met Tyr Asp Leu Asn Pro Glu
225                 230                 235                 240

Asp Thr Ser Arg Ala Leu Val Pro Pro Phe Asp Lys Tyr Trp Tyr Glu
                245                 250                 255

Ser Val Glu Lys Gly Arg Arg Lys Gln Ile Ala Ala Asp Lys Lys Ala
            260                 265                 270

Gly Lys Thr Asn Leu Val Tyr Lys Pro Asn Ala Ala Thr Asn Gly Ser
        275                 280                 285

Val Leu Pro Ala Met Val Lys Ala Tyr Gly Gly Pro Phe Trp Phe Ala
290                 295                 300

Gly Met Leu Gln Phe Ala Ile Ser Gly Leu Gln Phe Ala Ser Pro Tyr
305                 310                 315                 320

Leu Met Gln Glu Ile Met Ala Val Ile Ala Leu Asp Gly Pro Phe Trp
                325                 330                 335

Lys Gly Met Ile Ile Thr Leu Gly Leu Phe Leu Thr Ser Leu Leu Ile
            340                 345                 350

Ala Leu Phe Asn Gly Gln Tyr Phe His Arg Thr Phe Leu Val Gly Phe
        355                 360                 365

Arg Ile Arg Thr Gly Leu Ile Ser Ala Ile Tyr Arg Lys Ala Leu Arg
370                 375                 380

Ile Ser Ser Phe Ala Lys Lys Asp Thr Thr Val Gly Glu Ile Val Asn
385                 390                 395                 400
```

-continued

```
Leu Met Ala Val Asp Ala Gln Arg Phe Phe Glu Leu Thr Ser Tyr Leu
                405                 410                 415
His Val Leu Trp Ser Ala Pro Leu Ile Ile Ala Leu Cys Ile Tyr Leu
                420                 425                 430
Leu Tyr Glu Leu Leu Gly Pro Ala Val Phe Ala Gly Leu Gly Val Met
                435                 440                 445
Val Ile Met Ile Pro Ile Thr Gly Phe Ile Ala Thr Arg Met Arg Asp
            450                 455                 460
Leu Gln Val Glu Gln Met Lys Ile Lys Asp Glu Arg Val Lys Lys Met
465                 470                 475                 480
Asn Glu Ile Leu Gly Gly Ile Lys Val Leu Lys Leu Tyr Ala Trp Glu
                    485                 490                 495
Pro Ser Phe Gln Asp Thr Val Val Thr Val Arg Asn Glu Glu Leu Asp
                500                 505                 510
Val Leu Lys Ser Ala Ala Tyr Tyr Gly Ala Gly Thr Tyr Phe Val Trp
                515                 520                 525
Thr Met Ala Pro Phe Leu Val Thr Leu Ala Ser Phe Ala Val Tyr Val
            530                 535                 540
Met Ile Asp Glu Glu Asn Val Leu Asp Pro Gln Thr Ala Phe Val Ala
545                 550                 555                 560
Leu Ala Leu Phe Asn Ile Leu Arg Phe Pro Leu Ala Met Phe Pro Met
                    565                 570                 575
Met Ile Thr Phe Ala Met Gln Ala Trp Val Ser Ile Lys Arg Ile Asp
                580                 585                 590
Lys Phe Met Asn Ser Glu Glu Leu Asp Pro Asn Asn Val Thr His Asn
                595                 600                 605
Lys Ser Glu Asn Ala Leu Glu Val Lys Asp Gly Thr Phe Ser Trp Gly
                610                 615                 620
Asp Asp Ala Pro Thr Leu Lys Asn Ile Asn Leu Ala Leu Arg Arg Gly
625                 630                 635                 640
Lys Leu Ser Ala Val Val Gly Gly Val Gly Thr Gly Lys Ser Ser Leu
                    645                 650                 655
Ile Ser Ala Leu Leu Gly Glu Met Glu Lys Met Lys Gly Ser Val Asn
                660                 665                 670
Thr Asp Gly Ser Ile Ala Tyr Val Pro Gln Gln Ala Trp Ile Gln Asn
                675                 680                 685
Ala Thr Leu Arg Asp Asn Ile Leu Phe Gly Arg Pro Phe Asp Gln Ala
            690                 695                 700
Lys Tyr Asp Lys Val Ile Glu Cys Cys Ala Leu Arg Pro Asp Leu Glu
705                 710                 715                 720
Met Leu Pro Gly Gly Asp Thr Thr Glu Ile Gly Glu Lys Gly Ile Asn
                    725                 730                 735
Leu Ser Gly Gly Gln Lys Gln Arg Val Ala Leu Ala Arg Ala Val Tyr
                740                 745                 750
Ala Asp Ser Glu Val Tyr Leu Phe Asp Asp Pro Leu Ser Ala Val Asp
                755                 760                 765
Ala His Val Gly Lys His Ile Phe Glu Lys Val Ile Gly Pro Ser Gly
            770                 775                 780
Met Leu Val Gly Arg Ser Arg Leu Leu Val Thr His Gly Ile Ser Phe
785                 790                 795                 800
Leu Pro Phe Val Glu Glu Ile Phe Val Met Lys Asp Gly Glu Val Ser
                    805                 810                 815
```

-continued

```
Glu Ser Gly Ser Tyr Gln Glu Leu Leu Asp Gln Lys Gly Ala Phe Ala
            820                 825                 830
Glu Phe Leu Thr Gln His Ile Gln Glu Met Asp Asp Glu Asp Glu Asp
        835                 840                 845
Glu Leu Lys Leu Ile Gln Glu Ala Leu Lys Asp Gly Glu Ala Lys Lys
    850                 855                 860
Ile Val Gln Arg Ala Met Ser Thr Arg Ser Gln Arg Ser Gly Ser Ser
865                 870                 875                 880
Asn Gly Ser Val Arg Lys Lys Val Ser Arg Ala Glu Ser Arg Asn
                885                 890                 895
Ser Asn Lys Pro Arg Ala Val Glu Gln Thr Val Ala Gln Gln Ser Ser
            900                 905                 910
Ala Thr Leu Ile Glu Lys Glu Ser Ala Thr Gly Ala Val Gly Tyr
        915                 920                 925
Val Val Tyr Ile Lys Tyr Phe Lys Gly Ile Gly Leu Trp Leu Gly Phe
    930                 935                 940
Trp Ser Ile Phe Phe Ser Val Ile Asn Gln Gly Ala Ser Ile Tyr Ala
945                 950                 955                 960
Asn Ile Trp Leu Thr Asp Trp Ser Glu Asp Pro Glu Ala Ala Thr Asp
                965                 970                 975
Pro Ser Val Arg Asp Met Tyr Leu Gly Val Tyr Gly Gly Leu Gly Gly
            980                 985                 990
Ala Gln Ser Ile Ala Leu Leu Ile Ala Ser Val Thr Leu Ala Leu Gly
        995                1000                1005
Cys Ile Lys Ala Ala Arg Glu Leu His Asn Asn Leu Leu Glu Ser Ser
    1010                1015                1020
Met Arg Met Pro Met Ser Phe Phe Asp Thr Thr Pro Leu Gly Arg Ile
1025                1030                1035                1040
Met Asn Arg Phe Ser Lys Asp Val Asp Val Val Asp Asn Ile Leu Pro
                1045                1050                1055
Gln Ser Ile Arg Ala Trp Leu Leu Met Phe Phe Asn Val Ile Gly Val
            1060                1065                1070
Phe Val Val Ile Gly Ile Ser Thr Pro Ile Phe Leu Ala Val Val Pro
        1075                1080                1085
Ala Phe Leu Val Ile Tyr Tyr Leu Ile Gln Lys Phe Tyr Ile Ala Thr
    1090                1095                1100
Ser Arg Gln Leu Lys Arg Leu Glu Ser Val Thr Arg Ser Pro Ile Tyr
1105                1110                1115                1120
Ser His Phe Gly Glu Ser Ile Thr Gly Gln Ser Thr Ile Arg Ala Tyr
                1125                1130                1135
Gly Gln Gln Asp Arg Phe Met Asn Glu Ser Glu Gln Arg Val Asp Tyr
            1140                1145                1150
Asn Gln Leu Thr Ser Tyr Pro Ser Ile Ile Ala Asn Arg Trp Leu Ala
        1155                1160                1165
Val Arg Leu Glu Leu Val Gly Ala Leu Val Val Phe Ala Ala Leu
    1170                1175                1180
Phe Ala Met Val Ala Arg Asp Thr Ile Gly Gln Ala Thr Val Gly Leu
1185                1190                1195                1200
Ser Ile Ser Tyr Ala Leu Gln Ile Ser Ala Thr Leu Ser Phe Leu Val
                1205                1210                1215
Arg Met Thr Ala Glu Val Glu Thr Asn Ile Val Ala Ile Glu Arg Leu
            1220                1225                1230
Glu Glu Tyr Thr Val Leu Pro Arg Glu Ala Glu Trp Gln Leu Gly His
```

-continued

```
                1235                1240                1245
Val Asp Lys Ala Trp Pro Val Glu Gly Lys Val Glu Phe Lys Asp Tyr
        1250                1255                1260
Gln Ile Arg Tyr Arg Glu Gly Leu Asp Leu Val Ile Arg Gly Ile Ser
1265                1270                1275                1280
Leu Asn Val Arg Gly Gly Glu Lys Ile Gly Ile Val Gly Arg Thr Gly
            1285                1290                1295
Ala Gly Lys Ser Ser Leu Thr Leu Gly Leu Phe Arg Ile Val Glu Ala
        1300                1305                1310
Ala Gly Gly Gln Ile Ile Ile Asp Gly Leu Asp Ile Ser Lys Met Gly
        1315                1320                1325
Leu His Gln Leu Arg Gly Arg Leu Thr Ile Ile Pro Gln Asp Pro Val
        1330                1335                1340
Leu Phe Ser Gly Thr Leu Arg Ala Asn Val Asp Pro Phe Lys Ser Tyr
1345                1350                1355                1360
Ser Asp Asp Leu Val Trp Lys Ala Leu Glu Leu Ser His Leu Lys Thr
            1365                1370                1375
Phe Val Lys Gly Leu Ala Ala Gly Leu Asp His Glu Ile Ala Glu Asn
        1380                1385                1390
Gly Glu Asn Leu Ser Val Gly Gln Arg Gln Leu Ile Cys Leu Ala Arg
        1395                1400                1405
Ala Val Leu Arg Lys Thr Lys Val Leu Ile Leu Asp Glu Ala Thr Ala
        1410                1415                1420
Ala Val Asp Leu Glu Thr Asp Asp Leu Ile Gln Lys Thr Ile Arg Thr
1425                1430                1435                1440
Glu Phe Ala Asp Cys Thr Ile Leu Thr Ile Ala His Arg Leu Asn Thr
            1445                1450                1455
Ile Leu Asp Ser Asp Arg Val Leu Val Leu Asp Lys Gly Leu Val Ala
            1460                1465                1470
Glu Cys Asp Ser Pro Gln Asn Leu Leu Ala Asn Arg Glu Ser Ile Phe
        1475                1480                1485
Phe Gly Met Ala Lys Asn Ala Gly Ile Val Ser
    1490                1495

<210> SEQ ID NO 4
<211> LENGTH: 1505
<212> TYPE: PRT
<213> ORGANISM: Anopheles gambiae

<400> SEQUENCE: 4

Met Thr Phe Glu Asp Phe Cys Gly Gly Pro Phe Trp Asp Gly Glu Phe
1               5                   10                  15
Val Trp Asp Val Asp Asn Pro Asn Leu Thr Phe Cys Phe Gln Arg Val
            20                  25                  30
Ile Leu Gln Trp Val Pro Cys Leu Phe Leu Phe Val Phe Ser Ile Tyr
        35                  40                  45
Asp Ile Phe Lys Ile Thr Glu Ser Lys Tyr Arg Asp Ile Pro Trp Asn
    50                  55                  60
Trp Tyr Asn Leu Ser Lys Met Leu Val Ile Phe Leu Leu Met Cys Met
65                  70                  75                  80
Cys Trp Ile Asp Leu Gly Met Val Val Gly Tyr Gln Asp Glu Gln Gly
                85                  90                  95
Leu Tyr Asp Val Gln Ile Leu Thr Ala Val Phe Asn Ala Leu Ala Tyr
            100                 105                 110
```

```
Ile Asp Leu Leu Val Leu Leu Phe Phe Met Arg Lys Tyr Gly Val Arg
    115                 120                 125

Thr Ser Gly Thr Met Phe Met Phe Trp Phe Leu Arg Met Phe Phe Gly
    130                 135                 140

Ile Ile Gln Leu Arg Thr Glu Val Met Glu Asn Asp Lys Arg Pro Asn
145                 150                 155                 160

Ala Ile Gly Ser Gly Asp Thr Val Asp Phe Trp Glu Tyr Gln Tyr Val
                165                 170                 175

Ser Tyr Ile Leu Gln Tyr Ser Leu Ile Cys Leu Met Leu Val Leu Glu
            180                 185                 190

Leu Phe Pro Asp Lys Glu Pro Ser Phe Ser Tyr Tyr Pro Lys Ala Ala
        195                 200                 205

Lys Pro Asn Pro Glu Leu Arg Ser Ser Phe Phe Ser Lys Leu Leu Phe
210                 215                 220

Leu His Phe Asp Ala Phe Ala Trp Lys Gly Phe Arg Asn Pro Leu Thr
225                 230                 235                 240

Met Asn Asp Met Tyr Asp Ile Asn Pro Gln Asp Ser Ala Arg Glu Leu
                245                 250                 255

Val Pro Pro Phe Asp Lys Tyr Trp Lys Ile Ser Val Glu Lys Gly Arg
            260                 265                 270

Lys Gln Gln Met Ala Ser Asp Arg Lys Ala Gly Lys Pro Asp Ile Asp
        275                 280                 285

Tyr Lys Pro His Ser Pro Ser Asn Gly Ser Val Leu Tyr Thr Met Ile
    290                 295                 300

Arg Ala Tyr Gly Gly Pro Phe Trp Phe Ala Gly Met Leu Gln Leu Ala
305                 310                 315                 320

Ile Ser Gly Leu Gln Phe Ala Ser Pro Tyr Leu Met Gln Glu Leu Met
                325                 330                 335

Ala Val Ile Ala Phe Asp Gly Pro Leu Trp Lys Gly Phe Leu Leu Thr
            340                 345                 350

Phe Gly Leu Phe Gly Ala Ser Leu Leu Gly Leu Phe Asn Gly Gln
        355                 360                 365

Tyr Leu Phe Tyr Thr Phe Leu Ser Gly Phe Arg Ile Arg Thr Gly Leu
    370                 375                 380

Ile Ser Ala Ile Tyr Arg Lys Ala Leu Arg Ile Ser Ala Ala Lys
385                 390                 395                 400

Lys Asp Thr Thr Val Gly Glu Ile Val Asn Leu Met Ala Val Asp Ala
                405                 410                 415

Gln Lys Phe Phe Glu Leu Thr Ser Tyr Leu His Ile Leu Trp Ser Ala
            420                 425                 430

Leu Leu Ile Ile Gly Leu Cys Val Phe Leu Leu Tyr Asp Ile Leu Gly
        435                 440                 445

Pro Ala Val Phe Ala Gly Leu Gly Val Met Ile Leu Met Thr Pro Val
450                 455                 460

Ser Gly Val Val Ala Ala Lys Leu Lys Thr His Gln Val Ala Gln Met
465                 470                 475                 480

Lys Leu Lys Asp Glu Arg Val Lys Lys Met Asn Glu Ile Leu Gly Gly
                485                 490                 495

Ile Lys Val Leu Lys Leu Tyr Ala Trp Glu Pro Ser Phe Gln Asp Ser
            500                 505                 510

Ile Leu Asn Val Arg Asp Glu Glu Val Gly Ile Leu Lys Lys Met Ala
        515                 520                 525

Tyr Tyr Gly Ala Gly Ile Phe Phe Thr Phe Thr Ile Ala Pro Phe Leu
```

```
                  530                 535                 540
Val Thr Leu Val Ser Phe Ala Val Tyr Val Leu Ile Asp Glu Asn Asn
545                 550                 555                 560

Val Leu Asp Pro Gln Thr Ala Phe Val Ser Leu Ala Leu Phe Asn Ile
                  565                 570                 575

Met Arg Phe Pro Leu Gly Met Phe Pro Met Val Val Thr Phe Ser Met
                  580                 585                 590

Gln Ala Trp Val Ser Ile Lys Arg Ile Asp Lys Phe Leu Asn Ser Ala
                  595                 600                 605

Glu Leu Asp Pro Asn Asn Val Thr His Asn Lys Ser Asp Glu Ala Leu
610                 615                 620

Thr Ile Lys Asp Gly Thr Phe Ser Trp Gly Asp Glu Thr Pro Thr Leu
625                 630                 635                 640

Lys Asn Ile Asn Leu Ser Leu Arg Lys Gly Gln Leu Ser Ala Ile Val
                  645                 650                 655

Gly Thr Val Gly Thr Gly Lys Ser Ser Leu Ile Ser Ala Leu Leu Gly
                  660                 665                 670

Glu Met Glu Lys Ile Ser Gly His Val Asn Thr Asp Gly Ser Ile Ala
                  675                 680                 685

Tyr Val Pro Gln Gln Ala Trp Ile Gln Asn Ala Thr Leu Arg Asp Asn
                  690                 695                 700

Ile Leu Phe Gly Lys Ala Phe Asp Gln Arg Lys Tyr Asp Asn Val Ile
705                 710                 715                 720

Glu Cys Cys Ala Leu Arg Pro Asp Leu Glu Met Leu Pro Gly Gly Asp
                  725                 730                 735

Ser Thr Glu Ile Gly Glu Lys Gly Ile Asn Leu Ser Gly Gly Gln Lys
                  740                 745                 750

Gln Arg Val Ala Leu Ala Arg Ala Val Tyr Ala Asp Ala Glu Val Tyr
                  755                 760                 765

Leu Phe Asp Asp Pro Leu Ser Ala Val Asp Ala His Val Gly Lys His
                  770                 775                 780

Ile Phe Glu Lys Val Ile Gly Pro Ser Gly Met Leu Val Gly Lys Ser
785                 790                 795                 800

Arg Leu Leu Val Thr His Gly Ile Ser Phe Leu Pro Phe Val Glu Asn
                  805                 810                 815

Ile Leu Val Leu Lys Asp Gly Glu Ile Ser Glu Ser Gly Thr Tyr Gln
                  820                 825                 830

Glu Leu Ile Asp Gln Lys Gly Ala Phe Ala Glu Phe Leu Ser Gln His
                  835                 840                 845

Ile Gln Glu Leu Asp Asp Glu Asp Glu Glu Ile Ser Leu Ile Gln Glu
850                 855                 860

Thr Leu Asn Asp Gly Val Val Asn Asn Val Ile Gln Arg Ala Leu Ser
865                 870                 875                 880

Val Arg Ser Asn Arg Ser Asn Gly Ser Asp Gly Ser Thr Arg Lys Lys
                  885                 890                 895

Pro Ile Ser Arg Gln Val Ser Lys Gln Ser Val His Ser Lys Thr Val
                  900                 905                 910

Thr Thr Val Pro Gly Arg Ala Asn Leu Ile Gly Val Glu Glu Ser Ala
                  915                 920                 925

Thr Gly Ala Val Thr Trp Leu Val Tyr Lys Lys Tyr Ile Gln Ser Ile
                  930                 935                 940

Gly Phe Lys Phe Gly Phe Gly Ser Val Leu Phe Thr Ala Ile Asn Gln
945                 950                 955                 960
```

Gly Ser Gly Ile Phe Ser Asn Leu Trp Leu Thr Asp Trp Ser Glu Asp
            965                 970                 975

Pro Asp Ala Ala Thr Asp Pro Ser Val Arg Asp Lys Tyr Leu Gly Val
            980                 985                 990

Tyr Gly Ala Leu Gly Gly Ala Gln Ser Ile Ala Leu Phe Val Ala Ala
            995                1000                1005

Leu Leu Ile Ser Leu Gly Cys Leu Lys Ala Ala Lys Glu Ser His Asn
           1010                1015                1020

Lys Leu Leu Glu Ser Cys Leu Arg Met Pro Met Ser Phe Phe Asp Thr
1025                1030                1035                1040

Thr Pro Leu Gly Arg Ile Ile Asn Arg Phe Ser Lys Asp Val Asp Val
           1045                1050                1055

Val Asp Asn Val Leu Pro Val Thr Ile Arg Ala Trp Leu Leu Phe Leu
           1060                1065                1070

Phe Asn Val Phe Gly Val Phe Ile Val Ile Gly Thr Ser Thr Pro Ile
           1075                1080                1085

Phe Leu Ala Val Val Pro Pro Leu Met Val Ile Tyr Tyr Phe Val Gln
           1090                1095                1100

Arg Phe Tyr Ile Asp Thr Ser Arg Gln Leu Lys Arg Leu Glu Ser Val
1105                1110                1115                1120

Thr Arg Ser Pro Ile Tyr Ser His Phe Gly Glu Ser Ile Gly Gly Gln
           1125                1130                1135

Ser Thr Ile Arg Ala Tyr Gly Gln Gln Asp Arg Phe Thr Gln Glu Ser
           1140                1145                1150

Glu Arg Arg Val Asp Tyr Asn Gln Leu Val Ser Tyr Pro Thr Ile Val
           1155                1160                1165

Ala Asn Arg Trp Leu Ala Val Arg Leu Glu Leu Ile Gly Ser Cys Val
           1170                1175                1180

Ile Leu Phe Ala Ala Leu Phe Ala Ile Leu Ala Arg Asp Thr Ile Gly
1185                1190                1195                1200

Gln Ala Thr Val Gly Val Ser Ile Ser Tyr Ala Leu Gln Ile Ser His
           1205                1210                1215

Tyr Leu Ser Phe Leu Val Arg Met Thr Ser Glu Val Glu Thr Asn Ile
           1220                1225                1230

Val Ala Val Glu Arg Leu Glu Glu Tyr Thr Val Leu Pro Arg Glu Ala
           1235                1240                1245

Glu Trp Gln Lys Gly Thr Val Asp Lys Ala Trp Pro Val Glu Gly Lys
           1250                1255                1260

Val Glu Phe Lys Asp Tyr Gln Ile Arg Tyr Arg Glu Gly Leu Asp Leu
1265                1270                1275                1280

Val Ile Arg Gly Ile Ser Leu Asn Val Arg Gly Gly Glu Lys Ile Gly
           1285                1290                1295

Ile Val Gly Arg Thr Gly Ala Gly Lys Ser Ser Leu Thr Leu Gly Leu
           1300                1305                1310

Phe Arg Ile Val Glu Ala Ala Gly Gly Gln Ile Ile Ile Asp Gly Leu
           1315                1320                1325

Asp Ile Ser Lys Met Gly Leu His Gln Leu Arg Gly Arg Leu Thr Ile
           1330                1335                1340

Ile Pro Gln Asp Pro Val Leu Phe Ser Gly Thr Leu Arg Ala Asn Val
1345                1350                1355                1360

Asp Pro Phe Lys Ser Tyr Ser Asp Asp Gln Val Trp Lys Ala Leu Glu
           1365                1370                1375

```
Leu Ser His Leu Lys Thr Phe Val Lys Gly Leu Ser Ala Gly Leu Asp
        1380                1385                1390

His Glu Ile Ala Glu Asn Gly Glu Asn Leu Ser Val Gly Gln Arg Gln
    1395                1400                1405

Leu Ile Cys Leu Ala Arg Ala Val Leu Arg Lys Thr Lys Val Leu Ile
    1410                1415                1420

Leu Asp Glu Ala Thr Ala Ala Val Asp Leu Glu Thr Asp Asp Leu Ile
1425                1430                1435                1440

Gln Lys Thr Ile Arg Thr Glu Phe Ala Asp Cys Thr Ile Leu Thr Ile
            1445                1450                1455

Ala His Arg Leu Asn Thr Ile Leu Asp Ser Asp Arg Val Leu Val Leu
        1460                1465                1470

Asp Lys Gly Leu Val Ala Glu Cys Asp Ser Pro Gln Asn Leu Leu Ala
    1475                1480                1485

Asn Arg Glu Ser Ile Phe Tyr Gly Met Ala Lys Asn Ala Gly Ile Val
    1490                1495                1500

Ser
1505

<210> SEQ ID NO 5
<211> LENGTH: 1507
<212> TYPE: PRT
<213> ORGANISM: Anopheles gambiae

<400> SEQUENCE: 5

Met Thr Phe Glu Asp Phe Cys Gly Gly Pro Phe Trp Asp Asp Glu Phe
1               5                   10                  15

Val Trp Asp Val Asp Asn Pro Asn Leu Thr Phe Cys Phe Gln Arg Val
            20                  25                  30

Ile Leu Gln Trp Val Pro Cys Leu Phe Leu Phe Val Phe Ser Ile Tyr
        35                  40                  45

Asp Ile Phe Lys Ile Thr Glu Ser Lys Tyr Arg Asp Ile Pro Trp Asn
    50                  55                  60

Trp Tyr Asn Leu Ser Lys Met Leu Val Ile Phe Leu Leu Met Cys Met
65                  70                  75                  80

Cys Trp Ile Asp Leu Gly Met Val Val Gly Tyr Gln Asp Glu Gln Gly
                85                  90                  95

Leu Tyr Asp Val Gln Ile Leu Thr Ala Val Phe Asn Ala Leu Ala Tyr
            100                 105                 110

Ile Asp Leu Leu Val Leu Leu Phe Phe Met Arg Lys Tyr Gly Val Arg
        115                 120                 125

Thr Ser Gly Thr Met Phe Met Phe Trp Phe Leu Arg Met Phe Phe Gly
    130                 135                 140

Ile Ile Gln Leu Arg Thr Glu Val Met Glu Asn Asp Lys Arg Pro Asn
145                 150                 155                 160

Ala Ile Gly Ser Gly Asp Thr Val Asp Phe Trp Glu Tyr Gln Tyr Val
                165                 170                 175

Ser Tyr Ile Leu Gln Tyr Ser Leu Ile Cys Leu Met Leu Val Leu Glu
            180                 185                 190

Leu Phe Pro Asp Lys Glu Pro Thr Phe Ser Tyr Tyr Pro Lys Ser Lys
        195                 200                 205

Asn Pro Asn Pro Glu Leu Lys Ser Ser Phe Ala Lys Leu Leu Phe
    210                 215                 220

Leu Tyr Phe Asp Thr Phe Ala Trp Lys Gly Phe Arg Lys Pro Leu Thr
225                 230                 235                 240
```

```
Met Glu Glu Met Tyr Asp Ile Asn Pro Gln Asp Thr Ser Arg Glu Leu
            245                 250                 255

Val Pro Pro Phe Asp Lys Tyr Trp Asp Met Ser Val Ala Asn Gly Arg
        260                 265                 270

Lys Lys Gln Ile Ala Ala Asp Lys Ala Gly Lys Thr Asn Ile Glu
        275                 280                 285

Tyr Lys Pro His Ser Glu Thr Asn Gly Ser Ser Leu Tyr Ala Met Val
        290                 295                 300

Arg Ala Tyr Gly Ala Pro Phe Trp Phe Ala Gly Met Leu Gln Leu Ala
305                 310                 315                 320

Ile Ser Gly Leu Gln Phe Ala Ser Pro Tyr Leu Met Gln Glu Met Met
                325                 330                 335

Ala Val Ile Ala Leu Asp Gly Pro Val Trp Lys Gly Leu Leu Leu Thr
            340                 345                 350

Phe Ala Leu Phe Ala Ala Ser Leu Leu Leu Ala Leu Leu Asn Gly Gln
        355                 360                 365

Tyr Tyr Tyr Asn Thr Phe Leu Ser Gly Phe Arg Ile Arg Thr Gly Leu
        370                 375                 380

Val Ser Ala Ile Tyr Arg Lys Ala Leu Arg Ile Ser Ser Ala Ala Lys
385                 390                 395                 400

Lys Asp Thr Thr Val Gly Glu Ile Val Asn Leu Met Ala Val Asp Ala
            405                 410                 415

Gln Arg Phe Phe Glu Leu Thr Ser Tyr Met His Ile Leu Trp Ser Gly
        420                 425                 430

Val Leu Ile Ile Ala Leu Cys Val Tyr Leu Leu Tyr Asp Ile Leu Gly
        435                 440                 445

Ala Ala Val Phe Ala Gly Leu Gly Val Met Ile Leu Ile Thr Pro Val
        450                 455                 460

Ser Gly Val Ile Ala Thr Lys Met Arg Asp Ala Gln Val Ala Gln Met
465                 470                 475                 480

Lys Ile Lys Asp Asp Arg Val Lys Lys Met Asn Glu Ile Leu Gly Gly
            485                 490                 495

Ile Lys Val Leu Lys Leu Tyr Ala Trp Glu Pro Ser Phe Gln Asp Asn
        500                 505                 510

Ile Leu Thr Val Arg Lys Glu Glu Ile Gly Ile Leu Lys Arg Met Ala
        515                 520                 525

Tyr Tyr Gly Ala Gly Ile Tyr Phe Thr Phe Thr Ile Ala Pro Phe Leu
        530                 535                 540

Val Thr Leu Val Ser Phe Ala Val Tyr Val Leu Met Asp Glu Glu Asn
545                 550                 555                 560

Ile Leu Asp Pro Gln Thr Ala Phe Val Ser Leu Ala Leu Phe Asn Ile
            565                 570                 575

Leu Arg Phe Pro Leu Gly Met Leu Pro Met Met Val Thr Phe Ser Met
        580                 585                 590

Gln Ala Trp Val Ser Val Lys Arg Ile Asp Lys Phe Leu Asn Ser Ala
        595                 600                 605

Glu Leu Asp Pro Ser Asn Val Ser Asn Lys Ser Asp Glu Ala Leu
        610                 615                 620

Thr Ile Lys Asp Gly Thr Phe Ser Trp Gly Asp Glu Thr Pro Thr Leu
625                 630                 635                 640

Lys Asn Ile Asn Leu Ser Leu Arg Lys Gly Gln Leu Ser Ala Ile Val
            645                 650                 655
```

```
Gly Thr Val Gly Thr Gly Lys Ser Ser Leu Ile Ser Ala Leu Leu Gly
            660                 665                 670

Glu Met Glu Lys Ile Ser Gly His Val Asn Thr Asp Gly Ser Ile Ala
            675                 680                 685

Tyr Val Pro Gln Gln Ala Trp Ile Gln Asn Ala Thr Leu Arg Asp Asn
            690                 695                 700

Ile Leu Phe Gly Lys Ala Phe Asp Gln Arg Lys Tyr Asp Asn Val Ile
705                 710                 715                 720

Glu Cys Cys Ala Leu Arg Pro Asp Leu Glu Met Leu Pro Gly Gly Asp
                    725                 730                 735

Ser Thr Glu Ile Gly Glu Lys Gly Ile Asn Leu Ser Gly Gly Gln Lys
                740                 745                 750

Gln Arg Val Ala Leu Ala Arg Ala Val Tyr Ala Asp Ala Glu Val Tyr
            755                 760                 765

Leu Phe Asp Asp Pro Leu Ser Ala Val Asp Ala His Val Gly Lys His
            770                 775                 780

Ile Phe Glu Lys Val Ile Gly Pro Ser Gly Met Leu Val Gly Lys Ser
785                 790                 795                 800

Arg Leu Leu Val Thr His Gly Ile Ser Tyr Leu Pro Phe Val Glu Asn
                    805                 810                 815

Ile Phe Val Val Lys Asp Gly Glu Ile Ser Glu Ser Gly Ser Tyr Gln
                820                 825                 830

Gln Leu Leu Asp Gln Lys Gly Ala Phe Ala Glu Phe Leu Thr Gln His
            835                 840                 845

Ile Gln Glu Leu Asp Glu Ala Asp Glu Asp Glu Ile Lys Leu Ile Gln
            850                 855                 860

Glu Thr Leu Lys Asp Glu Thr Ala Gln Arg Ile Val Glu Arg Ser Leu
865                 870                 875                 880

Ser Val Arg Ser Gly Arg Ser Gly Gly Ser Asn Ser Ser Ile Arg Lys
                    885                 890                 895

Lys Arg Ile Ser Arg Gln Glu Ser Lys Ala Ser Ala Lys Lys Glu Asp
                900                 905                 910

Pro Ile Ile Gln Asn Leu Asp Lys Ala Thr Leu Ile Glu Lys Glu Glu
            915                 920                 925

Ser Ala Thr Gly Ala Val Thr Trp Ala Val Tyr Lys Lys Tyr Val Thr
            930                 935                 940

Ala Ile Gly Phe Gln Phe Gly Phe Trp Ser Val Phe Ser Ala Ile
945                 950                 955                 960

Asn Gln Gly Ser Gly Ile Tyr Ser Ser Met Trp Leu Thr Asp Trp Ser
                    965                 970                 975

Glu Asp Pro Glu Ala Ile Thr Asp Thr Ser Val Arg Asp Met Tyr Leu
                980                 985                 990

Gly Val Tyr Gly Ala Leu Gly Gly Val Gln Ser Ile Ala Leu Phe Ile
            995                 1000                1005

Gly Ser Val Leu Leu Ala Leu Gly Cys Leu Lys Ala Ala Glu Glu Ser
    1010                1015                1020

His Asn Lys Leu Leu Glu Ser Ser Met His Met Pro Met Ser Phe Phe
1025                1030                1035                1040

Asp Thr Thr Pro Leu Gly Arg Ile Ile Asn Arg Phe Ser Lys Asp Val
                    1045                1050                1055

Asp Val Val Asp Asn Ile Leu Pro Ala Thr Ile Arg Ala Trp Leu Leu
            1060                1065                1070

Met Leu Phe Ser Val Ile Gly Val Phe Val Val Ile Gly Ile Ser Thr
```

```
                      -continued
            1075                1080                1085

Pro Ile Phe Leu Ala Ile Val Pro Pro Leu Met Ile Ile Tyr Tyr Phe
        1090                1095                1100

Val Gln Arg Phe Tyr Ile Glu Thr Ser Arg Gln Leu Lys Arg Leu Glu
1105                1110                1115                1120

Ser Val Thr Arg Ser Pro Ile Tyr Ser His Phe Gly Glu Ser Ile Gly
            1125                1130                1135

Gly Gln Ser Thr Ile Arg Ala Tyr Ala Gln Gln Glu Arg Phe Ile Arg
        1140                1145                1150

Glu Ser Glu His Arg Val Asp Tyr Asn Gln Leu Val Thr Tyr Pro Thr
    1155                1160                1165

Ile Leu Ala Asn Arg Trp Leu Gly Val Arg Leu Glu Ile Ile Gly Ser
1170                1175                1180

Leu Val Ile Leu Phe Ala Ala Leu Phe Ala Ile Leu Ala Arg Asp Thr
1185                1190                1195                1200

Ile Gly Gln Ala Thr Val Gly Leu Ser Ile Ser Tyr Ala Leu Gln Ile
            1205                1210                1215

Ser Asn Val Leu Ser Phe Leu Val Arg Met Thr Ala Glu Val Glu Thr
        1220                1225                1230

Asn Ile Val Ala Ile Glu Arg Leu Glu Glu Tyr Thr Val Leu Pro Arg
1235                1240                1245

Glu Ala Glu Trp Gln Lys Gly Thr Val Asp Lys Ala Trp Pro Val Glu
1250                1255                1260

Gly Lys Val Glu Phe Lys Asp Tyr Gln Ile Arg Tyr Arg Glu Gly Leu
1265                1270                1275                1280

Asp Leu Val Ile Arg Gly Ile Ser Leu Asn Val Arg Gly Gly Glu Lys
            1285                1290                1295

Ile Gly Ile Val Gly Arg Thr Gly Ala Gly Lys Ser Ser Leu Thr Leu
        1300                1305                1310

Gly Leu Phe Arg Ile Val Glu Ala Ala Gly Gly Gln Ile Ile Ile Asp
    1315                1320                1325

Gly Leu Asp Ile Ser Lys Met Gly Leu His Gln Leu Arg Ser Arg Leu
1330                1335                1340

Thr Ile Ile Pro Gln Asp Pro Val Leu Phe Ser Gly Thr Leu Arg Ala
1345                1350                1355                1360

Asn Val Asp Pro Phe Lys Ser Tyr Ser Asp Asp Gln Val Trp Lys Ala
            1365                1370                1375

Leu Glu Leu Ser His Leu Lys Thr Phe Val Lys Gly Leu Thr Ala Gly
        1380                1385                1390

Leu Asp His Glu Ile Ala Glu Asn Gly Glu Asn Leu Ser Val Gly Gln
    1395                1400                1405

Arg Gln Leu Val Cys Leu Ala Arg Ala Ile Leu Arg Lys Thr Lys Val
1410                1415                1420

Leu Ile Leu Asp Glu Ala Thr Ala Ala Val Asp Leu Glu Thr Asp Asp
1425                1430                1435                1440

Leu Ile Gln Lys Thr Ile Arg Thr Glu Phe Ala Asp Cys Thr Ile Leu
            1445                1450                1455

Thr Ile Ala His Arg Leu Asn Thr Ile Leu Asp Ser Asp Arg Val Leu
        1460                1465                1470

Val Leu Asp Lys Gly Leu Val Ala Glu Cys Asp Ser Pro Gln Asn Leu
    1475                1480                1485

Leu Ala Asn Arg Asp Ser Ile Phe His Ser Met Ala Lys Asn Ala Gly
1490                1495                1500
```

Ile Val Ser
1505

<210> SEQ ID NO 6
<211> LENGTH: 1531
<212> TYPE: PRT
<213> ORGANISM: Homo sapiens

<400> SEQUENCE: 6

```
Met Ala Leu Arg Gly Phe Cys Ser Ala Asp Gly Ser Asp Pro Leu Trp
 1               5                  10                  15

Asp Trp Asn Val Thr Trp Asn Thr Ser Asn Pro Asp Phe Thr Lys Cys
                20                  25                  30

Phe Gln Asn Thr Val Leu Val Trp Val Pro Cys Phe Tyr Leu Trp Ala
            35                  40                  45

Cys Phe Pro Phe Tyr Phe Leu Tyr Leu Ser Arg His Asp Arg Gly Tyr
        50                  55                  60

Ile Gln Met Thr Pro Leu Asn Lys Thr Lys Thr Ala Leu Gly Phe Leu
65                  70                  75                  80

Leu Trp Ile Val Cys Trp Ala Asp Leu Phe Tyr Ser Phe Trp Glu Arg
                85                  90                  95

Ser Arg Gly Ile Phe Leu Ala Pro Val Phe Leu Val Ser Pro Thr Leu
                100                 105                 110

Leu Gly Ile Thr Thr Leu Leu Ala Thr Phe Leu Ile Gln Leu Glu Arg
            115                 120                 125

Arg Lys Gly Val Gln Ser Ser Gly Ile Met Leu Thr Phe Trp Leu Val
130                 135                 140

Ala Leu Val Cys Ala Leu Ala Ile Leu Arg Ser Lys Ile Met Thr Ala
145                 150                 155                 160

Leu Lys Glu Asp Ala Gln Val Asp Leu Phe Arg Asp Ile Thr Phe Tyr
                165                 170                 175

Val Tyr Phe Ser Leu Leu Leu Ile Gln Leu Val Leu Ser Cys Phe Ser
            180                 185                 190

Asp Arg Ser Pro Leu Phe Ser Glu Thr Ile His Asp Pro Asn Pro Cys
        195                 200                 205

Pro Glu Ser Ser Ala Ser Phe Leu Ser Arg Ile Thr Phe Trp Trp Ile
    210                 215                 220

Thr Gly Leu Ile Val Arg Gly Tyr Arg Gln Pro Leu Glu Gly Ser Asp
225                 230                 235                 240

Leu Trp Ser Leu Asn Lys Glu Asp Thr Ser Glu Gln Val Val Pro Val
                245                 250                 255

Leu Val Lys Asn Trp Lys Lys Glu Cys Ala Lys Thr Arg Lys Gln Pro
            260                 265                 270

Val Lys Val Val Tyr Ser Ser Lys Asp Pro Ala Gln Pro Lys Glu Ser
        275                 280                 285

Ser Lys Val Asp Ala Asn Glu Glu Val Glu Ala Leu Ile Val Lys Ser
    290                 295                 300

Pro Gln Lys Glu Trp Asn Pro Ser Leu Phe Lys Val Leu Tyr Lys Thr
305                 310                 315                 320

Phe Gly Pro Tyr Phe Leu Met Ser Phe Phe Lys Ala Ile His Asp
                325                 330                 335

Leu Met Met Phe Ser Gly Pro Gln Ile Leu Lys Leu Leu Ile Lys Phe
            340                 345                 350

Val Asn Asp Thr Lys Ala Pro Asp Trp Gln Gly Tyr Phe Tyr Thr Val
```

-continued

```
            355                 360                 365
Leu Leu Phe Val Thr Ala Cys Leu Gln Thr Leu Val Leu His Gln Tyr
        370                 375                 380
Phe His Ile Cys Phe Val Ser Gly Met Arg Ile Lys Thr Ala Val Ile
385                 390                 395                 400
Gly Ala Val Tyr Arg Lys Ala Leu Val Ile Thr Asn Ser Ala Arg Lys
                405                 410                 415
Ser Ser Thr Val Gly Glu Ile Val Asn Leu Met Ser Val Asp Ala Gln
                420                 425                 430
Arg Phe Met Asp Leu Ala Thr Tyr Ile Asn Met Ile Trp Ser Ala Pro
        435                 440                 445
Leu Gln Val Ile Leu Ala Leu Tyr Leu Leu Trp Leu Asn Leu Gly Pro
        450                 455                 460
Ser Val Leu Ala Gly Val Ala Val Met Val Leu Met Val Pro Val Asn
465                 470                 475                 480
Ala Val Met Ala Met Lys Thr Lys Thr Tyr Gln Val Ala His Met Lys
                485                 490                 495
Ser Lys Asp Asn Arg Ile Lys Leu Met Asn Glu Ile Leu Asn Gly Ile
                500                 505                 510
Lys Val Leu Lys Leu Tyr Ala Trp Glu Leu Ala Phe Lys Asp Lys Val
        515                 520                 525
Leu Ala Ile Arg Gln Glu Glu Leu Lys Val Leu Lys Lys Ser Ala Tyr
        530                 535                 540
Leu Ser Ala Val Gly Thr Phe Thr Trp Val Cys Thr Pro Phe Leu Val
545                 550                 555                 560
Ala Leu Cys Thr Phe Ala Val Tyr Val Thr Ile Asp Glu Asn Asn Ile
                565                 570                 575
Leu Asp Ala Gln Thr Ala Phe Val Ser Leu Ala Leu Phe Asn Ile Leu
                580                 585                 590
Arg Phe Pro Leu Asn Ile Leu Pro Met Val Ile Ser Ser Ile Val Gln
        595                 600                 605
Ala Ser Val Ser Leu Lys Arg Leu Arg Ile Phe Leu Ser His Glu Glu
        610                 615                 620
Leu Glu Pro Asp Ser Ile Glu Arg Arg Pro Val Lys Asp Gly Gly Gly
625                 630                 635                 640
Thr Asn Ser Ile Thr Val Arg Asn Ala Thr Phe Thr Trp Ala Arg Ser
                645                 650                 655
Asp Pro Pro Thr Leu Asn Gly Ile Thr Phe Ser Ile Pro Glu Gly Ala
                660                 665                 670
Leu Val Ala Val Val Gly Gln Val Gly Cys Gly Lys Ser Ser Leu Leu
        675                 680                 685
Ser Ala Leu Leu Ala Glu Met Asp Lys Val Glu Gly His Val Ala Ile
        690                 695                 700
Lys Gly Ser Val Ala Tyr Val Pro Gln Gln Ala Trp Ile Gln Asn Asp
705                 710                 715                 720
Ser Leu Arg Glu Asn Ile Leu Phe Gly Cys Gln Leu Glu Glu Pro Tyr
                725                 730                 735
Tyr Arg Ser Val Ile Gln Ala Cys Ala Leu Leu Pro Asp Leu Glu Ile
                740                 745                 750
Leu Pro Ser Gly Asp Arg Thr Glu Ile Gly Glu Lys Gly Val Asn Leu
        755                 760                 765
Ser Gly Gly Gln Lys Gln Arg Val Ser Leu Ala Arg Ala Val Tyr Ser
        770                 775                 780
```

-continued

```
Asn Ala Asp Ile Tyr Leu Phe Asp Asp Pro Leu Ser Ala Val Asp Ala
785                 790                 795                 800

His Val Gly Lys His Ile Phe Glu Asn Val Ile Gly Pro Lys Gly Met
            805                 810                 815

Leu Lys Asn Lys Thr Arg Ile Leu Val Thr His Ser Met Ser Tyr Leu
        820                 825                 830

Pro Gln Val Asp Val Ile Ile Val Met Ser Gly Gly Lys Ile Ser Glu
    835                 840                 845

Met Gly Ser Tyr Gln Glu Leu Leu Ala Arg Asp Gly Ala Phe Ala Glu
850                 855                 860

Phe Leu Arg Thr Tyr Ala Ser Thr Glu Gln Glu Gln Asp Ala Glu Glu
865                 870                 875                 880

Asn Gly Val Thr Gly Val Ser Gly Pro Gly Lys Glu Ala Lys Gln Met
            885                 890                 895

Glu Asn Gly Met Leu Val Thr Asp Ser Ala Gly Lys Gln Leu Gln Arg
        900                 905                 910

Gln Leu Ser Ser Ser Ser Tyr Ser Gly Asp Ile Ser Arg His His
    915                 920                 925

Asn Ser Thr Ala Glu Leu Gln Lys Ala Glu Ala Lys Lys Glu Glu Thr
930                 935                 940

Trp Lys Leu Met Glu Ala Asp Lys Ala Gln Thr Gly Gln Val Lys Leu
945                 950                 955                 960

Ser Val Tyr Trp Asp Tyr Met Lys Ala Ile Gly Leu Phe Ile Ser Phe
            965                 970                 975

Leu Ser Ile Phe Leu Phe Met Cys Asn His Val Ser Ala Leu Ala Ser
        980                 985                 990

Asn Tyr Trp Leu Ser Leu Trp Thr Asp Asp Pro Ile Val Asn Gly Thr
    995                 1000                1005

Gln Glu His Thr Lys Val Arg Leu Ser Val Tyr Gly Ala Leu Gly Ile
    1010                1015                1020

Ser Gln Gly Ile Ala Val Phe Gly Tyr Ser Met Ala Val Ser Ile Gly
1025                1030                1035                1040

Gly Ile Leu Ala Ser Arg Cys Leu His Val Asp Leu Leu His Ser Ile
            1045                1050                1055

Leu Arg Ser Pro Met Ser Phe Phe Glu Arg Thr Pro Ser Gly Asn Leu
        1060                1065                1070

Val Asn Arg Phe Ser Lys Glu Leu Asp Thr Val Asp Ser Met Ile Pro
    1075                1080                1085

Glu Val Ile Lys Met Phe Met Gly Ser Leu Phe Asn Val Ile Gly Ala
    1090                1095                1100

Cys Ile Val Ile Leu Leu Ala Thr Pro Ile Ala Ala Ile Ile Ile Pro
1105                1110                1115                1120

Pro Leu Gly Leu Ile Tyr Phe Phe Val Gln Arg Phe Tyr Val Ala Ser
            1125                1130                1135

Ser Arg Gln Leu Lys Arg Leu Glu Ser Val Ser Arg Ser Pro Val Tyr
        1140                1145                1150

Ser His Phe Asn Glu Thr Leu Leu Gly Val Ser Val Ile Arg Ala Phe
    1155                1160                1165

Glu Glu Gln Glu Arg Phe Ile His Gln Ser Asp Leu Lys Val Asp Glu
    1170                1175                1180

Asn Gln Lys Ala Tyr Tyr Pro Ser Ile Val Ala Asn Arg Trp Leu Ala
1185                1190                1195                1200
```

```
Val Arg Leu Glu Cys Val Gly Asn Cys Ile Val Leu Phe Ala Ala Leu
            1205                1210                1215

Phe Ala Val Ile Ser Arg His Ser Leu Ser Ala Gly Leu Val Gly Leu
        1220                1225                1230

Ser Val Ser Tyr Ser Leu Gln Val Thr Thr Tyr Leu Asn Trp Leu Val
    1235                1240                1245

Arg Met Ser Ser Glu Met Glu Thr Asn Ile Val Ala Val Glu Arg Leu
1250                1255                1260

Lys Glu Tyr Ser Glu Thr Glu Lys Glu Ala Pro Trp Gln Ile Gln Glu
1265                1270                1275                1280

Thr Ala Pro Pro Ser Ser Trp Pro Gln Val Gly Arg Val Glu Phe Arg
            1285                1290                1295

Asn Tyr Cys Leu Arg Tyr Arg Glu Asp Leu Asp Phe Val Leu Arg His
        1300                1305                1310

Ile Asn Val Thr Ile Asn Gly Gly Glu Lys Val Gly Ile Val Gly Arg
    1315                1320                1325

Thr Gly Ala Gly Lys Ser Ser Leu Thr Leu Gly Leu Phe Arg Ile Asn
1330                1335                1340

Glu Ser Ala Glu Gly Glu Ile Ile Ile Asp Gly Ile Asn Ile Ala Lys
1345                1350                1355                1360

Ile Gly Leu His Asp Leu Arg Phe Lys Ile Thr Ile Ile Pro Gln Asp
            1365                1370                1375

Pro Val Leu Phe Ser Gly Ser Leu Arg Met Asn Leu Asp Pro Phe Ser
        1380                1385                1390

Gln Tyr Ser Asp Glu Glu Val Trp Thr Ser Leu Glu Leu Ala His Leu
    1395                1400                1405

Lys Asp Phe Val Ser Ala Leu Pro Asp Lys Leu Asp His Glu Cys Ala
1410                1415                1420

Glu Gly Gly Glu Asn Leu Ser Val Gly Gln Arg Gln Leu Val Cys Leu
1425                1430                1435                1440

Ala Arg Ala Leu Leu Arg Lys Thr Lys Ile Leu Val Leu Asp Glu Ala
            1445                1450                1455

Thr Ala Ala Val Asp Leu Glu Thr Asp Asp Leu Ile Gln Ser Thr Ile
        1460                1465                1470

Arg Thr Gln Phe Glu Asp Cys Thr Val Leu Thr Ile Ala His Arg Leu
    1475                1480                1485

Asn Thr Ile Met Asp Tyr Thr Arg Val Ile Val Leu Asp Lys Gly Glu
1490                1495                1500

Ile Gln Glu Tyr Gly Ala Pro Ser Asp Leu Leu Gln Gln Arg Gly Leu
1505                1510                1515                1520

Phe Tyr Ser Met Ala Lys Asp Ala Gly Leu Val
            1525                1530

<210> SEQ ID NO 7
<211> LENGTH: 49
<212> TYPE: PRT
<213> ORGANISM: Drosophila melanogaster

<400> SEQUENCE: 7

Val Ser Leu Val Thr Phe Ala Thr Tyr Val Leu Thr Ser Glu Ala Asn
  1               5                  10                  15

Gln Leu Ser Val Glu Lys Val Leu Val Ser Ile Ala Leu Phe Asp Leu
             20                  25                  30

Met Lys Leu Pro Leu Thr Ile Leu Pro Met Leu Ser Val Asp Ile Ala
         35                  40                  45
```

Glu

<210> SEQ ID NO 8
<211> LENGTH: 49
<212> TYPE: PRT
<213> ORGANISM: Drosophila melanogaster

<400> SEQUENCE: 8

Val Ser Leu Val Thr Phe Ala Thr Tyr Val Leu Ile Asp Glu Asn Asn
 1               5                  10                  15

Val Leu Asp Ala Thr Lys Thr Phe Val Ser Leu Ser Leu Phe Asn Ile
            20                  25                  30

Leu Arg Phe Pro Leu Thr Met Leu Pro Met Leu Ile Thr Asn Leu Val
        35                  40                  45

Gln

<210> SEQ ID NO 9
<211> LENGTH: 73
<212> TYPE: PRT
<213> ORGANISM: Drosophila melanogaster

<400> SEQUENCE: 9

Ala Thr Asn Phe Phe Ser Ser Leu Ala Ile Ser Leu Gly Cys Leu Lys
 1               5                  10                  15

Cys Ser Gln Leu Leu His Gln Thr Leu Leu Tyr Tyr Asn Leu Arg Trp
            20                  25                  30

Pro Met Glu Leu Phe Asp Thr Thr Pro Leu Gly Arg Ile Val Asn Arg
        35                  40                  45

Phe Ser Lys Asp Ile Asp Thr Ile Asp Asn Val Leu Pro Phe Asn Ile
    50                  55                  60

Arg Val Val Ile Gly Gln Ala Tyr Met
65                  70

<210> SEQ ID NO 10
<211> LENGTH: 73
<212> TYPE: PRT
<213> ORGANISM: Drosophila melanogaster

<400> SEQUENCE: 10

Val Thr Gly Tyr Leu Ser Thr Leu Ile Leu Ser Leu Gly Cys Val Tyr
 1               5                  10                  15

Ser Ala Arg Tyr Met His Asn Val Leu Leu His Gly Thr Leu Arg Trp
            20                  25                  30

Pro Met Glu Met Phe Asp Ile Thr Pro Leu Gly Arg Ile Val Asn Arg
        35                  40                  45

Phe Ser Lys Asp Val Asp Thr Ile Asp Asn Thr Leu Pro Leu Asn Leu
    50                  55                  60

Arg Val Val Ile Leu Gln Leu Phe Ala
65                  70

<210> SEQ ID NO 11
<211> LENGTH: 73
<212> TYPE: PRT
<213> ORGANISM: Drosophila melanogaster

<400> SEQUENCE: 11

Thr Ser Tyr Phe Phe Cys Ser Leu Thr Leu Ala Leu Gly Cys Ile Pro
 1               5                  10                  15

```
Cys Ser Lys Val Leu His Glu Thr Leu Leu Ser Tyr Val Phe Arg Trp
             20                  25                  30

Pro Met Glu Leu Phe Asp Thr Thr Pro Leu Gly Arg Val Val Asn Arg
             35                  40                  45

Phe Ser Lys Asp Val Asp Thr Ile Asp Asn Val Leu Pro Met Leu Trp
 50                  55                  60

Arg Met Val Ile Ser Gln Ala Phe Ala
 65                  70
```

<210> SEQ ID NO 12
<211> LENGTH: 73
<212> TYPE: PRT
<213> ORGANISM: Drosophila melanogaster

<400> SEQUENCE: 12

```
Leu Ser Lys Tyr Leu Ser Gly Leu Ala Leu Ala Ile Gly Gly Leu His
  1               5                  10                  15

Cys Ser Met Asn Val Phe Asn Lys Leu Leu Asn Thr Gly Leu Lys Trp
             20                  25                  30

Pro Met Glu Leu Phe Asp Thr Thr Pro Leu Gly Arg Ile Leu Ser Arg
             35                  40                  45

Tyr Ser Lys Asp Val Asp Thr Val Asp Ser Val Leu Pro Ala Ile Thr
 50                  55                  60

Val Gln Leu Leu Asn Thr Cys Phe Gly
 65                  70
```

<210> SEQ ID NO 13
<211> LENGTH: 74
<212> TYPE: PRT
<213> ORGANISM: Drosophila melanogaster

<400> SEQUENCE: 13

```
Val Leu Ala Tyr Phe Ala Val Val Ile Val Tyr Leu Gly Gly Phe Gln
  1               5                  10                  15

Ala Ala Lys Thr Ile His Asn Glu Leu Leu Ala Val Ile Ile Arg Gly
             20                  25                  30

Ser Val Cys Arg Phe Phe Asp Ile Thr Pro Ile Gly Arg Leu Leu Asn
             35                  40                  45

Ser Phe Ser Gly Asp Met Asp Val Val Asp Glu Glu Leu Pro Ala Thr
 50                  55                  60

Met Asp Ser Phe Met Thr Phe Ile Phe Met
 65                  70
```

<210> SEQ ID NO 14
<211> LENGTH: 73
<212> TYPE: PRT
<213> ORGANISM: Drosophila melanogaster

<400> SEQUENCE: 14

```
Leu Cys Asn Tyr Gly Ala Ala Ile Ser Leu Phe Thr Ala Thr Leu His
  1               5                  10                  15

Ala Ser Ser Arg Val Phe His Arg Leu Phe Asn Asn Ile Met His Cys
             20                  25                  30

Pro Ser Glu Phe Phe Asp Thr Thr Pro Lys Gly Arg Ile Leu Asp Arg
             35                  40                  45

Cys Ser Ser Asp Val Asn Cys Leu Asp Leu Val Met Pro Leu Asn Ile
 50                  55                  60

Arg Met Val Met Ser Thr Ala Phe Gln
 65                  70
```

<210> SEQ ID NO 15
<211> LENGTH: 73
<212> TYPE: PRT
<213> ORGANISM: Drosophila melanogaster

<400> SEQUENCE: 15

Phe Thr Ser Phe Phe Ser Asp Leu Ala Pro Ala Leu Gly Ser Leu His
 1               5                  10                  15

Ala Ala Lys Val Leu His Ser Met Leu Leu Glu Asn Val Leu Arg Ala
            20                  25                  30

Pro Met Thr Met Phe Asp Thr Thr Pro Val Gly Arg Ile Leu Ser Arg
        35                  40                  45

Phe Ser Lys Asp Val Glu Ser Val Asp Gln Lys Met Pro Gln Val Ile
    50                  55                  60

Asn Asp Cys Ile Trp Cys Ala Phe Glu
65                  70

<210> SEQ ID NO 16
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
gatccgttta tttccttgcc gc                                           22

<210> SEQ ID NO 17
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
tccagggcag tgattaccag t                                            21

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
agtgattgcc agtcgcatca                                              20

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
gccgttctca atgctcattg                                              20

<210> SEQ ID NO 20

<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 20
ctcggctatg tcaacactca                                              20

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 21
ttgcaccagg ttggtgatca                                              20

<210> SEQ ID NO 22
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 22
aacgatcaaa atgtcgcc                                                18

<210> SEQ ID NO 23
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 23
cacgaatagt cgatgctcc                                               19

<210> SEQ ID NO 24
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 24
gggaattcgc gtggacagac taat                                         24

<210> SEQ ID NO 25
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 25
gggaattcgc gacgaacttc ttctc                                        25

<210> SEQ ID NO 26
<211> LENGTH: 27

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
gggaattctt acctcgtact tcttttg                                          27

<210> SEQ ID NO 27
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
gggaattctt gttacagggt atctatc                                          27

<210> SEQ ID NO 28
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
gggaattcct atccaaatat ttatcgggg                                        29

<210> SEQ ID NO 29
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
gggaattcgt ttcacgtcat tcttttc                                          27

<210> SEQ ID NO 30
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
gggaattcgt ctttgcaatt acggcgc                                          27

<210> SEQ ID NO 31
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
gggaattcgt gtgctagcct actttgc                                          27

<210> SEQ ID NO 32
<211> LENGTH: 12
<212> TYPE: DNA
```

-continued

<213> ORGANISM: Drosophila melanogaster

<400> SEQUENCE: 32
gaacagaacg ca                                                        12

<210> SEQ ID NO 33
<211> LENGTH: 12
<212> TYPE: DNA
<213> ORGANISM: Drosophila melanogaster

<400> SEQUENCE: 33
acataggtgc tc                                                        12

<210> SEQ ID NO 34
<211> LENGTH: 12
<212> TYPE: DNA
<213> ORGANISM: Drosophila melanogaster

<400> SEQUENCE: 34
acaaaggttt cc                                                        12

<210> SEQ ID NO 35
<211> LENGTH: 12
<212> TYPE: DNA
<213> ORGANISM: Drosophila melanogaster

<400> SEQUENCE: 35
ttttaggttt ca                                                        12

<210> SEQ ID NO 36
<211> LENGTH: 12
<212> TYPE: DNA
<213> ORGANISM: Drosophila melanogaster

<400> SEQUENCE: 36
gaatagacgc aa                                                        12

<210> SEQ ID NO 37
<211> LENGTH: 12
<212> TYPE: DNA
<213> ORGANISM: Drosophila melanogaster

<400> SEQUENCE: 37
atacagccca tc                                                        12

<210> SEQ ID NO 38
<211> LENGTH: 12
<212> TYPE: DNA
<213> ORGANISM: Drosophila melanogaster

<400> SEQUENCE: 38
ttttagctcc gt                                                        12

<210> SEQ ID NO 39
<211> LENGTH: 12
<212> TYPE: DNA
<213> ORGANISM: Drosophila melanogaster

<400> SEQUENCE: 39
ttctagtcgc ga                                                        12

<210> SEQ ID NO 40
<211> LENGTH: 12

<212> TYPE: DNA
<213> ORGANISM: Drosophila melanogaster

<400> SEQUENCE: 40
tcgaagttgt ta                                                            12

<210> SEQ ID NO 41
<211> LENGTH: 12
<212> TYPE: DNA
<213> ORGANISM: Drosophila melanogaster

<400> SEQUENCE: 41
ttccagttac ct                                                            12

<210> SEQ ID NO 42
<211> LENGTH: 12
<212> TYPE: DNA
<213> ORGANISM: Drosophila melanogaster

<400> SEQUENCE: 42
atgcagtgct at                                                            12

<210> SEQ ID NO 43
<211> LENGTH: 12
<212> TYPE: DNA
<213> ORGANISM: Drosophila melanogaster

<400> SEQUENCE: 43
tcccaggtgt gc                                                            12

<210> SEQ ID NO 44
<211> LENGTH: 12
<212> TYPE: DNA
<213> ORGANISM: Drosophila melanogaster

<400> SEQUENCE: 44
agctaggtct tt                                                            12

<210> SEQ ID NO 45
<211> LENGTH: 12
<212> TYPE: DNA
<213> ORGANISM: Drosophila melanogaster

<400> SEQUENCE: 45
tcgcaggttt ca                                                            12

<210> SEQ ID NO 46
<211> LENGTH: 12
<212> TYPE: DNA
<213> ORGANISM: Drosophila melanogaster

<400> SEQUENCE: 46
ggttaggttc tg                                                            12

<210> SEQ ID NO 47
<211> LENGTH: 12
<212> TYPE: DNA
<213> ORGANISM: Drosophila melanogaster

<400> SEQUENCE: 47
cttcagcttt at                                                            12

<210> SEQ ID NO 48

-continued

```
<211> LENGTH: 12
<212> TYPE: DNA
<213> ORGANISM: Drosophila melanogaster

<400> SEQUENCE: 48
atttagaata at                                                          12

<210> SEQ ID NO 49
<211> LENGTH: 12
<212> TYPE: DNA
<213> ORGANISM: Drosophila melanogaster

<400> SEQUENCE: 49
ctatagaaaa cc                                                          12

<210> SEQ ID NO 50
<211> LENGTH: 12
<212> TYPE: DNA
<213> ORGANISM: Drosophila melanogaster

<400> SEQUENCE: 50
ttctgggtga gt                                                          12

<210> SEQ ID NO 51
<211> LENGTH: 12
<212> TYPE: DNA
<213> ORGANISM: Drosophila melanogaster

<400> SEQUENCE: 51
attaaggtga gt                                                          12

<210> SEQ ID NO 52
<211> LENGTH: 12
<212> TYPE: DNA
<213> ORGANISM: Drosophila melanogaster

<400> SEQUENCE: 52
ttcctggtaa ga                                                          12

<210> SEQ ID NO 53
<211> LENGTH: 12
<212> TYPE: DNA
<213> ORGANISM: Drosophila melanogaster

<400> SEQUENCE: 53
gccgaggtac ag                                                          12

<210> SEQ ID NO 54
<211> LENGTH: 12
<212> TYPE: DNA
<213> ORGANISM: Drosophila melanogaster

<400> SEQUENCE: 54
gtgcaagtaa gt                                                          12

<210> SEQ ID NO 55
<211> LENGTH: 12
<212> TYPE: DNA
<213> ORGANISM: Drosophila melanogaster

<400> SEQUENCE: 55
ctaaacgtaa ga                                                          12
```

<210> SEQ ID NO 56
<211> LENGTH: 12
<212> TYPE: DNA
<213> ORGANISM: Drosophila melanogaster

<400> SEQUENCE: 56
ttccatgtaa gt                                          12

<210> SEQ ID NO 57
<211> LENGTH: 12
<212> TYPE: DNA
<213> ORGANISM: Drosophila melanogaster

<400> SEQUENCE: 57
gccaaggtaa gt                                          12

<210> SEQ ID NO 58
<211> LENGTH: 12
<212> TYPE: DNA
<213> ORGANISM: Drosophila melanogaster

<400> SEQUENCE: 58
tatatggtaa tt                                          12

<210> SEQ ID NO 59
<211> LENGTH: 12
<212> TYPE: DNA
<213> ORGANISM: Drosophila melanogaster

<400> SEQUENCE: 59
tttgcggtaa tt                                          12

<210> SEQ ID NO 60
<211> LENGTH: 12
<212> TYPE: DNA
<213> ORGANISM: Drosophila melanogaster

<400> SEQUENCE: 60
tttgcggtaa at                                          12

<210> SEQ ID NO 61
<211> LENGTH: 12
<212> TYPE: DNA
<213> ORGANISM: Drosophila melanogaster

<400> SEQUENCE: 61
ttcggggtaa ag                                          12

<210> SEQ ID NO 62
<211> LENGTH: 12
<212> TYPE: DNA
<213> ORGANISM: Drosophila melanogaster

<400> SEQUENCE: 62
tttatggtat tt                                          12

<210> SEQ ID NO 63
<211> LENGTH: 12
<212> TYPE: DNA
<213> ORGANISM: Drosophila melanogaster

<400> SEQUENCE: 63
tttcaggtaa tc                                          12

```
<210> SEQ ID NO 64
<211> LENGTH: 12
<212> TYPE: DNA
<213> ORGANISM: Drosophila melanogaster

<400> SEQUENCE: 64
ttcgaggtaa tt                                                          12

<210> SEQ ID NO 65
<211> LENGTH: 12
<212> TYPE: DNA
<213> ORGANISM: Drosophila melanogaster

<400> SEQUENCE: 65
agatcggtat gt                                                          12

<210> SEQ ID NO 66
<211> LENGTH: 12
<212> TYPE: DNA
<213> ORGANISM: Drosophila melanogaster

<400> SEQUENCE: 66
gttcaggtaa gc                                                          12

<210> SEQ ID NO 67
<211> LENGTH: 12
<212> TYPE: DNA
<213> ORGANISM: Drosophila melanogaster

<400> SEQUENCE: 67
attcaggtgg gt                                                          12

<210> SEQ ID NO 68
<211> LENGTH: 49
<212> TYPE: PRT
<213> ORGANISM: Homo sapiens

<400> SEQUENCE: 68

Val Ala Leu Cys Thr Phe Ala Val Tyr Val Thr Ile Asp Glu Asn Asn
 1               5                  10                  15
Ile Leu Asp Ala Gln Thr Ala Phe Val Ser Leu Ala Leu Phe Asn Ile
             20                  25                  30
Leu Arg Phe Pro Leu Asn Ile Leu Pro Met Val Ile Ser Ser Leu Val
         35                  40                  45
Gln

<210> SEQ ID NO 69
<211> LENGTH: 49
<212> TYPE: PRT
<213> ORGANISM: Homo sapiens

<400> SEQUENCE: 69

Val Ser Val Val Thr Phe Ser Val Tyr Val Leu Val Asp Ser Asn Asn
 1               5                  10                  15
Ile Leu Asp Ala Gln Lys Ala Phe Thr Ser Ile Thr Leu Phe Asn Ile
             20                  25                  30
Leu Arg Phe Pro Leu Ser Met Leu Pro Met Met Ile Ser Ser Met Leu
         35                  40                  45
Gln
```

```
<210> SEQ ID NO 70
<211> LENGTH: 49
<212> TYPE: PRT
<213> ORGANISM: Homo sapiens

<400> SEQUENCE: 70

Val Thr Leu Ile Thr Leu Trp Val Tyr Val Tyr Val Asp Pro Asn Asn
 1               5                  10                  15

Val Leu Asp Ala Glu Lys Ala Phe Val Ser Val Ser Leu Phe Asn Ile
                20                  25                  30

Leu Arg Leu Pro Leu Asn Met Leu Pro Gln Leu Ile Ser Asn Leu Thr
            35                  40                  45

Gln

<210> SEQ ID NO 71
<211> LENGTH: 51
<212> TYPE: PRT
<213> ORGANISM: Drosophila melanogaster

<400> SEQUENCE: 71

Ile Thr Phe Val Thr Leu Gly Val Tyr Val Trp Leu His Arg Asp Gln
 1               5                  10                  15

Glu Phe Asp Leu Asn Ala Ser Arg Leu Phe Ser Ser Leu Ala Leu Phe
                20                  25                  30

Gln Gln Leu Thr Val Pro Leu Leu Ile Phe Pro Ile Thr Val Pro Ile
            35                  40                  45

Ile Ile Ala
        50

<210> SEQ ID NO 72
<211> LENGTH: 73
<212> TYPE: PRT
<213> ORGANISM: Homo sapiens

<400> SEQUENCE: 72

Ile Ala Val Phe Gly Tyr Ser Met Ala Val Ser Ile Gly Gly Ile Leu
 1               5                  10                  15

Ala Ser Arg Cys Leu His Val Asp Leu Leu His Ser Ile Leu Arg Ser
                20                  25                  30

Pro Met Ser Phe Glu Arg Thr Pro Ser Gly Asn Leu Val Asn Arg
            35                  40                  45

Phe Ser Lys Glu Leu Asp Thr Val Asp Ser Met Ile Pro Glu Val Ile
        50                  55                  60

Lys Met Phe Met Gly Ser Leu Phe Asn
 65                 70

<210> SEQ ID NO 73
<211> LENGTH: 73
<212> TYPE: PRT
<213> ORGANISM: Homo sapiens

<400> SEQUENCE: 73

Ile Phe Val Phe Ile Ala His Phe Trp Ser Ala Phe Gly Phe Val His
 1               5                  10                  15

Ala Ser Asn Ile Leu His Lys Gln Leu Leu Asn Asn Ile Leu Arg Ala
                20                  25                  30

Pro Met Arg Phe Phe Asp Thr Thr Pro Thr Gly Arg Ile Val Asn Arg
            35                  40                  45

Phe Ala Gly Asp Ile Ser Thr Val Asp Asp Thr Leu Pro Gln Ser Leu
```

-continued

```
                50                  55                  60
Arg Ser Trp Ile Thr Cys Phe Leu Gly
 65                  70

<210> SEQ ID NO 74
<211> LENGTH: 73
<212> TYPE: PRT
<213> ORGANISM: Homo sapiens

<400> SEQUENCE: 74

Phe Leu Val Met Leu Ala Ala Met Ala Met Ala Ala Gly Gly Ile Gln
 1               5                  10                  15

Ala Ala Arg Val Leu His Gln Ala Leu Leu His Asn Lys Ile Arg Ser
                20                  25                  30

Pro Gln Ser Phe Phe Asp Thr Thr Pro Ser Gly Arg Ile Leu Asn Cys
            35                  40                  45

Phe Ser Lys Asp Ile Tyr Val Val Asp Glu Val Leu Ala Pro Val Ile
        50                  55                  60

Leu Met Leu Leu Asn Ser Phe Phe Asn
 65                  70

<210> SEQ ID NO 75
<211> LENGTH: 69
<212> TYPE: PRT
<213> ORGANISM: Drosophila melanogaster

<400> SEQUENCE: 75

Val Ser Thr Pro Ala Gly Gln Tyr Ala Gly Cys Asn Ala Arg Arg Asn
 1               5                  10                  15

Leu His Asp Lys Leu Leu Gln Thr Ile Leu His Lys Thr Leu His Phe
                20                  25                  30

Phe Gln Val Thr Pro Leu Gly Arg Ile Val Asn Arg Phe Ser Asn Asp
            35                  40                  45

Met Ala Val Ile Asp Lys Lys Ile Ala Ala Thr Gly Gln Phe Thr Leu
        50                  55                  60

Arg Leu Leu Gln Leu
 65

<210> SEQ ID NO 76
<211> LENGTH: 72
<212> TYPE: PRT
<213> ORGANISM: Artificial Sequence
<220> FEATURE:
<223> OTHER INFORMATION: Description of Artificial Sequence: Consensus
      sequence for ABC transporter membrane spanning
      domain

<400> SEQUENCE: 76

Leu Leu Gln Gly Ser Phe Tyr Leu Gly Glu Arg Leu Gly Gln Arg Leu
 1               5                  10                  15

Arg Lys Arg Leu Phe Arg Ala Leu Leu Arg Gln Ile Leu Gly Leu Phe
                20                  25                  30

Met Ser Phe Phe Asp Thr Asn Ser Thr Gly Glu Leu Thr Ser Arg Leu
            35                  40                  45

Thr Asn Asp Val Ser Lys Ile Arg Asp Gly Leu Gly Glu Lys Leu Gly
        50                  55                  60

Leu Leu Phe Gln Ser Leu Ala Thr
 65                  70
```